United States Patent
Schulte et al.

(10) Patent No.: US 10,772,936 B2
(45) Date of Patent: Sep. 15, 2020

(54) METHODS FOR PREPARING MODIFIED VON WILLEBRAND FACTOR

(71) Applicant: CSL Behring Lengnau AG, Lengnau (CH)

(72) Inventors: Stefan Schulte, Marburg (DE); Hans-Wilhelm Beltz, Biedenkopf (DE); Sabine Pestel, Marburg (DE); Thomas Weimer, Gladenbach (DE); Matthias Pelzing, Thomastown (AU)

(73) Assignee: CSL BEHRING LENGNAU AG, Lengnau (CH)

( * ) Notice: Subject to any disclaimer, the term of this patent is extended or adjusted under 35 U.S.C. 154(b) by 0 days.

(21) Appl. No.: 15/576,061

(22) PCT Filed: May 20, 2016

(86) PCT No.: PCT/EP2016/061440
§ 371 (c)(1),
(2) Date: Nov. 21, 2017

(87) PCT Pub. No.: WO2016/188905
PCT Pub. Date: Dec. 1, 2016

(65) Prior Publication Data
US 2018/0153968 A1    Jun. 7, 2018

(30) Foreign Application Priority Data

May 22, 2015 (EP) .................................. 15168934

(51) Int. Cl.
| | | |
|---|---|---|
| A61K 38/00 | (2006.01) | |
| A61K 38/37 | (2006.01) | |
| C07K 14/755 | (2006.01) | |
| A61P 7/04 | (2006.01) | |
| A61K 38/17 | (2006.01) | |
| C07K 14/47 | (2006.01) | |
| G01N 30/96 | (2006.01) | |

(52) U.S. Cl.
CPC .......... *A61K 38/37* (2013.01); *A61K 38/1741* (2013.01); *A61P 7/04* (2018.01); *C07K 14/473* (2013.01); *C07K 14/755* (2013.01); *G01N 30/96* (2013.01); *C07K 2319/02* (2013.01); *C07K 2319/31* (2013.01)

(58) Field of Classification Search
None
See application file for complete search history.

(56) References Cited

U.S. PATENT DOCUMENTS

| | | |
|---|---|---|
| 4,399,216 A | 8/1983 | Axel et al. |
| 4,970,300 A | 11/1990 | Fulton et al. |
| 6,403,077 B1 | 6/2002 | Strom et al. |
| 7,256,253 B2 | 8/2007 | Bridon et al. |
| 2004/0087778 A1 | 5/2004 | Feige et al. |
| 2014/0072561 A1 | 3/2014 | Weimer et al. |

FOREIGN PATENT DOCUMENTS

| | | |
|---|---|---|
| EP | 0 117 058 | 8/1984 |
| EP | 0 117 060 | 8/1984 |
| WO | WO 1994/015625 A1 | 7/1994 |
| WO | WO 1997/003193 A1 | 1/1997 |
| WO | WO 1997/011957 A1 | 4/1997 |
| WO | WO 1997/040145 A1 | 10/1997 |
| WO | WO 98/31826 | 7/1998 |
| WO | WO 1999/055306 A1 | 11/1999 |
| WO | WO 2002/060951 A2 | 8/2002 |
| WO | WO 2002/103024 A2 | 12/2002 |
| WO | WO 2003/076567 A2 | 9/2003 |
| WO | WO 2003/087355 A1 | 10/2003 |
| WO | WO 2003/093313 A2 | 11/2003 |
| WO | WO 2004/058800 A2 | 7/2004 |
| WO | WO 2004/067566 A1 | 8/2004 |
| WO | WO 2004/075923 A2 | 9/2004 |
| WO | WO 2004/101740 A2 | 11/2004 |
| WO | WO 2005/000892 A2 | 1/2005 |
| WO | WO 2005/001025 A2 | 6/2005 |
| WO | WO 2005/063808 A1 | 7/2005 |
| WO | WO 2006/000448 A2 | 1/2006 |
| WO | WO 2006/053299 A2 | 5/2006 |
| WO | WO 2006/071801 A2 | 7/2006 |
| WO | WO 2006/108590 A1 | 10/2006 |
| WO | WO 2007/090584 A1 | 8/2007 |
| WO | WO 2007/126808 A1 | 11/2007 |
| WO | WO 2007/144173 A1 | 12/2007 |
| WO | WO 2008/008360 A1 | 1/2008 |
| WO | WO 2008/077616 A1 | 7/2008 |
| WO | WO 2009/086309 A2 | 7/2009 |
| WO | WO 2009/156137 A1 | 12/2009 |
| WO | WO 2011/060242 A2 | 5/2011 |
| WO | WO 2011/134919 A2 | 11/2011 |
| WO | WO 2013/083858 A1 | 6/2013 |

(Continued)

OTHER PUBLICATIONS

Pousset et al. Cancer Research 57. 4249-4256. Oct. 1, 1997.*
Lodish H. F., "Recognition of Complex Oligosaccharides by the Multi-Subunit Asialoglycoprotein Receptor," Trends in Biochemical Sciences (TIBS), 1991, 16:374-377.
Denis C. V. et al., "Clearance of von Willebrand Factor," Journal of Thrombosis and Haemostasis, 2008, 99(2):271-278.
Shiltagh N. et al., "Solution Structure of the Major Factor VIII Binding Region on von Willebrand Factor," Blood Journal, 2014, 123(26):4143-4151.
D'Souza A. A. et al., "Asialoglycoprotein Receptor Mediated Hepatocyte Targeting—Strategies and Applications," Journal of Controlled Release, 2015, 203:126-139.
Stamper et al., "Crystal structure of the B7-1/CTLA-4 complex that inhibits human immune responses," Nature, 2001, 410(6828):608-611.

(Continued)

*Primary Examiner* — Jeanette M Lieb
(74) *Attorney, Agent, or Firm* — Finnegan, Henderson, Farabow, Garrett & Dunner, LLP

(57) ABSTRACT

The present invention provides modified von Willebrand Factor molecules, methods for their preparation and uses thereof. The invention further provides pharmaceutical compositions for treating coagulation disorders.

13 Claims, 25 Drawing Sheets

Specification includes a Sequence Listing.

(56) References Cited

FOREIGN PATENT DOCUMENTS

| WO | WO 2013/093760 A2 | 6/2013 |
| WO | WO 2013/106787 A1 | 7/2013 |
| WO | WO 2013/120939 A1 | 8/2013 |
| WO | WO 2014/198699 A2 | 12/2014 |
| WO | WO201498699 A2 * | 12/2014 |

OTHER PUBLICATIONS

International search report issued in corresponding International Application No. PCT/EP2016/061440, dated Dec. 1, 2016, 6 pages.

International preliminary report on patentability issued in corresponding International Application No. PCT/EP2016/061440, dated Nov. 28, 2017, 13 pages.

Written opinion of the international searching authority issued in corresponding International Application No. PCT/EP2016/061440, dated Dec. 1, 2016, 11 pages.

Collins, C. J., et al., "Molecular cloning of the human gene for von Willebrand factor and identification of the transcription initiation site," Proc. Natl. Acad. Sci., vol. 84, pp. 4393-4397 (1987).

Fischer, B., et al., "Structural analysis of recombinant von Willebrand factor: identification of hetero- and homo-dimers," FEBS Letters, vol. 351, pp. 345-348 (1994).

Kaufman, R. J., et al., "Effect of von Willebrand factor coexpression on the synthesis and secretion of factor VIII in chinese hamster ovary cells," Molecular and Cellular Biology, vol. 9, No. 3, pp. 1233-1242 (1989).

Yee, A., et al., "A von Willebrand factor fragment containing the D'D3 domains is sufficient to stabilize coagulation factor VIII in mice," Blood, 124(3):445-452 (2014).

Trummer, E., et al., "Process parameter shifting: part I. effect of DOT, pH, and temperature on the performance of Epo-Fc expressing CHO cells cultivated in controlled batch bioreactors," Biotech. Bioeng., vol. 94, No. 6, pp. 1033-1044 (2006).

Ahn, W. S., et al., "Effect of culture temperature on erythropoietin production and glycosylation in a perfusion culture of recombinant CHO cells," Biotech. Bioeng., vol. 101, No. 6, pp. 1234-1244 (2008).

Varki, A., "Diversity in the sialic acids," Glycobiology, vol. 2, No. 1, pp. 25-40 (1992).

Stokmaier, D., et al., "Design, synthesis and evaluation of monovalent ligands for the asialoglycoprotein receptor (ASGP-R)," Biorganic & Medical Chemistry, vol. 17, pp. 7254-7264 (2009).

Zhou, Y. F., et al., "Sequence and structure relationships within von Willebrand factor," Blood, vol. 120, No. 2, pp. 449-458 (2012).

Schellenberger, V., et al., "A recombinant polypeptide extens the in vivo half-life of peptides and proteins in a tunable manner," Nature Biotechnology, vol. 27, No. 12, pp. 1186-1190 (2009).

Dumont, J. A., et al., "Monomeric Fc fusions—impact on pharmacokinetic and biological activity of protein therapeutics," Biodrugs, Vo. 20(3), pp. 151-160 (2006).

Graham, F. L., et al., "Characteristics of a human cell line transformed by DNA from human adenovirus type 5," J. Gen. Virol., vol. 36, pp. 59-74 (1977).

Urlaub, G., et al., "Isolation of Chinese hamster cell mutants deficient in dihydrofolate reductase activity," Proc. Natl. Acad. Sci., vol. 77, No. 7, pp. 4216-4220 (1980).

Mather, J. P., "Establishment and characterization of two distinct mouse testicular epithelial cell lines," Biology of Reproduction, vol. 23, pp. 243-252 (1980).

Mather, J. P., "Culture of testicular cells in hormone-supplemented serum-free medium," Annaly NY Acad. Sci., vol. 383, No. 1, pp. 44-68 (1982).

Gething, M. J., et al., "Cell-surface expression of influenza haemagglutinin from a cloned DNA copy of the RNA gene," Nature, vol. 293, No. 293, pp. 620-625 (1981).

Mantei, N., et al., "Rabbit β-globin mRNA production in mouse L cells transformed with cloned rabbit 13-globin chromosomal DNA," Nature, vol. 281, pp. 40-46 (1979).

Graham, F. L., et al., "A new technique for the assay of infectivity of human adenovirus 5 DNA," Virology, vol. 52, pp. 456-467 (1973).

Hawley-Nelson, P., et al., "Lipofectamine™ reagent: a new, higher efficiency polycationic liposome transfection reagent," Focus, vol. 15, No. 3, pp. 73-79 (1973).

Keown, W. A., et al., "Methods for introducing DNA into mammalian cells," Methods in Enzymology, vol. 185, pp. 527-537 (1990).

Mansour, S. L., et al., "Disruption of the proto-oncogene int-2 in mouse embryo-derived stem cells: a general strategy for targeting mutations to non-selectable genes," Nature, vol. 336, No. 24, pp. 348-352 (1988).

Lee, L. M., et al., "An effect of predilution on potency assays of factor VIII concentrates," Thrombosis Research, vol. 30, pp. 511-519 (1983).

* cited by examiner

Figure 5
Legend to the glycostructures shown in figures 6 to 25
 Gal      galactose
 Man      mannose
 GlcNAc      N-acetyl glucoseamine
 Neu5Ac      N-acetyl neuraminic acid
 Neu5Gc      N-glycolyl neuraminic acid
 Fuc      fucose
 $SO_4$      sulfated
 Glycostructures with two or three non-sialylated terminal galactose residues

B-140526

| | area (total) | % area | area (≥2Gal) | area (≥2Gal) % | area | area % |
|---|---|---|---|---|---|---|
| neutrals | 94589264 | 58.8% | 51343311 | 31.9% | 11123382 | 6.9% |
| mono-sialo | 47772996 | 29.7% | 9817280 | 6.1% | | |
| di-sialo | 14774933 | 9.2% | 1058467 | 0.7% | | |
| tri-sialo | 3067249 | 1.9% | 0 | | | |
| tetra-sialo | 663241 | 0.4% | 0 | | | |
| sum | 160867683 | 100.0% | | 38.7% | | |

B-140616KS

| | area (total) | % area | area (≥2Gal) | area (≥2Gal) % | area | area % |
|---|---|---|---|---|---|---|
| neutrals | 17287446 | 16.9% | 13545655 | 13.3% | 2292351 | 2.2% |
| mono-sialo | 35233768 | 34.5% | 5659923 | 5.5% | | |
| di-sialo | 28897880 | 28.3% | 2458332 | 2.4% | | |
| tri-sialo | 14757994 | 14.5% | 0 | | | |
| tetra-sialo | 5838511 | 5.7% | 0 | | | |
| sum | 102015599 | 100.0% | | 21.2% | | |

B-140825

| | area (total) | % area | area (≥2Gal) | area (≥2Gal) % | area | area % |
|---|---|---|---|---|---|---|
| neutrals | 31785272 | 12.5% | 20701501 | 8.1% | 4753422 | 1.9% |
| mono-sialo | 105332368 | 41.3% | 11614275 | 4.6% | | |
| di-sialo | 83837480 | 32.9% | 13042209 | 5.1% | | |
| tri-sialo | 27314364 | 10.7% | 0 | | | |
| tetra-sialo | 6648490 | 2.6% | 0 | | | |
| sum | 254917974 | 100.0% | | 17.8% | | |

B-140623KS

| | area (total) | % area | area (≥2Gal) | area (≥2Gal) % | area | area % |
|---|---|---|---|---|---|---|
| neutrals | 745636 | 10.3% | 400734 | 5.5% | 81888 | 1.1% |
| mono-sialo | 2700827 | 37.3% | 225251 | 3.1% | | |
| di-sialo | 2325044 | 32.1% | 60686 | 0.8% | | |
| tri-sialo | 994698 | 13.8% | 0 | | | |
| tetra-sialo | 466100 | 6.4% | 0 | | | |
| sum | 7232305 | 100.0% | | 9.5% | | |

SEQUENCE LISTING

```
<160> NUMBER OF SEQ ID NOS: 12

<210> SEQ ID NO 1
<211> LENGTH: 5616
<212> TYPE: DNA
<213> ORGANISM: Artificial Sequence
<220> FEATURE:
<223> OTHER INFORMATION: DNA encoding construct VWF fragment - G/S
      linker - albumin
<220> FEATURE:
<221> NAME/KEY: misc_feature
<222> LOCATION: (1)..(6)
<223> OTHER INFORMATION: EcoRI restriction enzyme cleavage site
<220> FEATURE:
<221> NAME/KEY: misc_feature
<222> LOCATION: (32)..(3757)
<223> OTHER INFORMATION: coding sequence for VWF amino acids 1 to 1242
<220> FEATURE:
<221> NAME/KEY: misc_feature
<222> LOCATION: (3758)..(3850)
<223> OTHER INFORMATION: coding sequence for glycine/serine linker
<220> FEATURE:
<221> NAME/KEY: misc_feature
<222> LOCATION: (3851)..(5608)
<223> OTHER INFORMATION: coding sequence for human albumin
<220> FEATURE:
<221> NAME/KEY: misc_feature
<222> LOCATION: (5609)..(5616)
<223> OTHER INFORMATION: NotI restriction enzyme cleavage site

<400> SEQUENCE: 1
gaattcccgc agccctcatt tgcaggggaa gatgattcct gccagatttg ccggggtgct      60
gcttgctctg gccctcattt tgccagggac cctttgtgca gaaggaactc gcggcaggtc     120
atccacggcc cgatgcagcc ttttcggaag tgacttcgtc aacacctttg atgggagcat     180
gtacagcttt gcgggatact gcagttacct cctggcaggg ggctgccaga aacgctcctt     240
ctcgattatt gggacttcc agaatggcaa gagagtgagc ctctccgtgt atcttgggga     300
attttttgac atccatttgt ttgtcaatgg taccgtgaca caggggacc aaagagtctc     360 catgccctat gcctccaaag ggctgtatct agaaactgag gctgggtact acaagctgtc     420
cggtgaggcc tatggctttg tggccaggat cgatggcagc ggcaactttc aagtcctgct     480
gtcagacaga tacttcaaca agacctgcgg gctgtgtggc aactttaaca tctttgctga     540
agatgacttt atgacccaag aagggacctt gacctcggac ccttatgact tgccaactc      600 atgggctctg agcagtggag aacagtggtg tgaacggca tctcctccca gcagctcatg     660
caacatctcc tctggggaaa tgcagaaggg cctgtgggag cagtgccagc ttctgaagag     720
cacctcggtg tttgcccgct gccaccctct ggtggacccc gagccttttg tggccctgtg     780
tgagaagact tgtgtgagt gtgctggggg gctggagtgc gcctgccctg ccctcctgga     840
gtacgcccgg acctgtgccc aggagggaat ggtgctgtac ggctggaccg accacagcgc     900
gtgcagccca gtgcccctg ctggtatgga gtataggcag tgtgtgtccc cttgcgccag     960
gacctgccag agcctgcaca tcaatgaaat gtgtcaggag cgatgcgtgg atggctgcag    1020
```

```
ctgccctgag ggacagctcc tggatgaagg cctctgcgtg gagagcaccg agtgtccctg    1080
cgtgcattcc ggaaagcgct accctcccgg cacctccctc tctcgagact gcaacacctg    1140
catttgccga aacagccagt ggatctgcag caatgaagaa tgtccagggg agtgccttgt    1200
cacaggtcaa tcacacttca agagctttga caacagatac ttcaccttca gtgggatctg    1260
ccagtacctg ctggcccggg attgccagga ccactccttc tccattgtca ttgagactgt    1320
ccagtgtgct gatgaccgcg acgctgtgtg cacccgctcc gtcaccgtcc ggctgcctgg    1380
cctgcacaac agccttgtga aactgaagca tggggcagga gttgccatgg atggccagga    1440
cgtccagctc cccctcctga aggtgacct ccgcatccag catacagtga cggcctccgt    1500
gcgcctcagc tacggggagg acctgcagat ggactgggat ggccgcggga ggctgctggt    1560
gaagctgtcc cccgtctatg ccgggaagac ctgcggcctg tgtgggaatt acaatggcaa    1620
ccagggcgac gacttcctta cccccctctgg gctggcggag ccccgggtgg aggacttcgg    1680
gaacgcctgg aagctgcacg gggactgcca ggacctgcag aagcagcaca gcgatccctg    1740
cgccctcaac ccgcgcatga ccaggttctc cgaggaggcg tgcgcggtcc tgacgtcccc    1800
cacattcgag gcctgccatc gtgccgtcag cccgctgccc tacctgcgga actgccgcta    1860
cgacgtgtgc tcctgctcgg acggccgcga gtgcctgtgc ggcgccctgg ccagctatgc    1920
cgcggcctgc gcggggagag gcgtgcgcgt cgcgtggcgc gagccaggcc gctgtgagct    1980
gaactgcccg aaaggccagg tgtacctgca gtgcgggacc ccctgcaacc tgacctgccg    2040
ctctctctct tacccggatg aggaatgcaa tgaggcctgc ctggagggct gcttctgccc    2100
cccagggctc tacatggatg agagggggga ctgcgtgccc aaggcccagt gccctgttta    2160
ctatgacggt gagatcttcc agccagaaga catcttctca gaccatcaca ccatgtgcta    2220
ctgtgaggat ggcttcatgc actgtaccat gagtggagtc cccggaagct tgctgcctga    2280
cgctgtcctc agcagtcccc tgtctcatcg cagcaaaagg agcctatcct gtcggccccc    2340
catggtcaag ctggtgtgtc ccgctgacaa cctgcgggct gaagggctcg agtgtaccaa    2400
aacgtgccag aactatgacc tggagtgcat gagcatgggc tgtgtctctg gctgcctctg    2460
ccccccgggc atggtccggc atgagaacag atgtgtggcc ctggaaaggt gtccctgctt    2520
ccatcagggc aaggagtatg cccctggaga acagtgaag attggctgca acacttgtgt    2580
ctgtcgggac cggaagtgga actgcacaga ccatgtgtgt gatgccacgt gctccacgat    2640
cggcatggcc cactacctca ccttcgacgg gctcaaatac ctgttccccg gggagtgcca    2700
gtacgttctg gtgcaggatt actgcggcag taaccctggg acctttcgga tcctagtggg    2760
gaataaggga tgcagccacc cctcagtgaa atgcaagaaa cgggtcacca tcctggtgga    2820
gggaggagag attgagctgt ttgacgggga ggtgaatgtg aagaggccca tgaaggatga    2880
gactcacttt gaggtggtgg agtctggccg gtacatcatt ctgctgctgg gcaaagccct    2940
ctccgtggtc tgggaccgcc acctgagcat tccgtggtc ctgaagcaga cataccagga    3000
gaaagtgtgt ggcctgtgtg ggaattttga tggcatccag aacaatgacc tcaccagcag    3060
caacctccaa gtggaggaag accctgtgga ctttgggaac tcctggaaag tgagctcgca    3120
gtgtgctgac accagaaaag tgcctctgga ctcatcccct gccacctgcc ataacaacat    3180
catgaagcag acgatggtgg attcctcctg tagaatcctt accagtgacg tcttccagga    3240
ctgcaacaag ctggtggacc ccgagccata tctggatgtc tgcatttacg acacctgctc    3300
ctgtgagtcc attggggact gcgcctgctt ctgcgacacc attgctgcct atgcccacgt    3360
```

```
gtgtgcccag catggcaagg tggtgacctg gaggacggcc acattgtgcc cccagagctg    3420
cgaggagagg aatctccggg agaacgggta tgagtgtgag tggcgctata acagctgtgc    3480
acctgcctgt caagtcacgt gtcagcaccc tgagccactg gcctgccctg tgcagtgtgt    3540
ggagggctgc catgcccact gccctccagg gaaaatcctg gatgagcttt tgcagacctg    3600
cgttgaccct gaagactgtc cagtgtgtga ggtggctggc cggcgttttg cctcaggaaa    3660
gaaagtcacc ttgaatccca gtgaccctga gcactgccag atttgccact gtgatgttgt    3720
caacctcacc tgtgaagcct gccaggagcc gggaggctcg agcggggat ctggcgggtc     3780 tggaggctct ggagggtcgg gaggctctgg aggctctggg ggatctggcg ggtctggagg    3840
gtcgggatcc gatgcacaca agagtgaggt tgctcatcgg tttaaagatt tgggagaaga    3900
aaatttcaaa gccttggtgt tgattgcctt tgctcagtat cttcagcagt gtccatttga    3960
agatcatgta aaattagtga atgaagtaac tgaatttgca aaaacatgtg ttgctgatga    4020
gtcagctgaa aattgtgaca atcacttca taccctttttt ggagacaaat tatgcacagt    4080
tgcaactctt cgtgaaacct atggtgaaat ggctgactgc tgtgcaaaac aagaacctga    4140
gagaaatgaa tgcttcttgc aacacaaaga tgacaaccca aacctccccc gattggtgag    4200
accagaggtt gatgtgatgt gcactgcttt tcatgacaat gaagagacat ttttgaaaaa    4260
atacttatat gaaattgcca gaagacatcc ttacttttat gccccggaac tccttttctt    4320
tgctaaaagg tataaagctg cttttacaga atgttgccaa gctgctgata agctgcctg     4380 cctgttgcca aagctcgatg aacttcggga tgaagggaag gcttcgtctg ccaaacagag    4440
actcaagtgt gccagtctcc aaaaatttgg agaaagagct ttcaaagcat gggcagtagc    4500
tcgcctgagc cagagatttc ccaaagctga gtttgcagaa gtttccaagt tagtgacaga    4560
tcttaccaaa gtccacacgg aatgctgcca tggagatctg cttgaatgtg ctgatgacag    4620
ggcggacctt gccaagtata tctgtgaaaa tcaagattcg atctccagta aactgaagga    4680
atgctgtgaa aaacctctgt tggaaaaatc ccactgcatt gccgaagtgg aaaatgatga    4740
gatgcctgct gacttgcctt cattagctgc tgattttgtt gaaagtaagg atgtttgcaa    4800
aaactatgct gaggcaaagg atgtcttcct gggcatgttt ttgtatgaat atgcaagaag    4860
gcatcctgat tactctgtcg tgctgctgct gagacttgcc aagacatatg aaaccactct    4920
agagaagtgc tgtgccgctg cagatcctca tgaatgctat gccaaagtgt tcgatgaatt    4980
taaacctctt gtggaagagc tcagaatttt aatcaaacaa aattgtgagc tttttgagca    5040
gcttggagag tacaaattcc agaatgcgct attagttcgt tacaccaaga aagtacccca    5100
agtgtcaact ccaactcttg tagaggtctc aagaaaccta ggaaaagtgg gcagcaaatg    5160
ttgtaaacat cctgaagcaa aaagaatgcc ctgtgcagaa gactatctat ccgtggtcct    5220
gaaccagtta tgtgtgttgc atgagaaaac gccagtaagt gacagagtca ccaaatgctg    5280
cacagaatcc ttggtgaaca ggcgaccatg ctttttcagct ctggaagtcg atgaaacata   5340
cgttcccaaa gagtttaatg ctgaaacatt caccttccat gcagatatat gcacactttc    5400
tgagaaggag agacaaatca agaaacaaac tgcacttgtt gagctcgtga acacaagcc    5460 caaggcaaca aaagagcaac tgaaagctgt tatggatgat ttcgcagctt ttgtagagaa    5520
gtgctgcaag gctgacgata aggagacctg ctttgccgag gagggtaaaa aacttgttgc    5580
tgcaagtcaa gctgccttag gcttataggc ggccgc                              5616
```

<210> SEQ ID NO 2
<211> LENGTH: 1095

```
<212> TYPE: PRT
<213> ORGANISM: Artificial Sequence
<220> FEATURE:
<223> OTHER INFORMATION: polypeptide encoded by SEQ ID NO:1
<220> FEATURE:
<221> NAME/KEY: MISC_FEATURE
<222> LOCATION: (1)..(479)
<223> OTHER INFORMATION: VWF D'D3 region (VWF amino acids 764 - 1242)
<220> FEATURE:
<221> NAME/KEY: MISC_FEATURE
<222> LOCATION: (480)..(510)
<223> OTHER INFORMATION: glycine/serine linker
<220> FEATURE:
<221> NAME/KEY: MISC_FEATURE
<222> LOCATION: (511)..(1195)
<223> OTHER INFORMATION: human albumin

<400> SEQUENCE: 2

Ser Leu Ser Cys Arg Pro Pro Met Val Lys Leu Val Cys Pro Ala Asp
1               5                   10                  15

Asn Leu Arg Ala Glu Gly Leu Glu Cys Thr Lys Thr Cys Gln Asn Tyr
            20                  25                  30

Asp Leu Glu Cys Met Ser Met Gly Cys Val Ser Gly Cys Leu Cys Pro
        35                  40                  45

Pro Gly Met Val Arg His Glu Asn Arg Cys Val Ala Leu Glu Arg Cys
    50                  55                  60

Pro Cys Phe His Gln Gly Lys Glu Tyr Ala Pro Gly Glu Thr Val Lys
65                  70                  75                  80

Ile Gly Cys Asn Thr Cys Val Cys Arg Asp Arg Lys Trp Asn Cys Thr
                85                  90                  95

Asp His Val Cys Asp Ala Thr Cys Ser Thr Ile Gly Met Ala His Tyr
            100                 105                 110

Leu Thr Phe Asp Gly Leu Lys Tyr Leu Phe Pro Gly Glu Cys Gln Tyr
        115                 120                 125

Val Leu Val Gln Asp Tyr Cys Gly Ser Asn Pro Gly Thr Phe Arg Ile
    130                 135                 140

Leu Val Gly Asn Lys Gly Cys Ser His Pro Ser Val Lys Cys Lys Lys
145                 150                 155                 160

Arg Val Thr Ile Leu Val Glu Gly Gly Glu Ile Glu Leu Phe Asp Gly
                165                 170                 175

Glu Val Asn Val Lys Arg Pro Met Lys Asp Glu Thr His Phe Glu Val
            180                 185                 190

Val Glu Ser Gly Arg Tyr Ile Ile Leu Leu Leu Gly Lys Ala Leu Ser
        195                 200                 205

Val Val Trp Asp Arg His Leu Ser Ile Ser Val Val Leu Lys Gln Thr
    210                 215                 220

Tyr Gln Glu Lys Val Cys Gly Leu Cys Gly Asn Phe Asp Gly Ile Gln
225                 230                 235                 240

Asn Asn Asp Leu Thr Ser Ser Asn Leu Gln Val Glu Glu Asp Pro Val
                245                 250                 255

Asp Phe Gly Asn Ser Trp Lys Val Ser Ser Gln Cys Ala Asp Thr Arg
            260                 265                 270

Lys Val Pro Leu Asp Ser Ser Pro Ala Thr Cys His Asn Asn Ile Met
        275                 280                 285

Lys Gln Thr Met Val Asp Ser Ser Cys Arg Ile Leu Thr Ser Asp Val
    290                 295                 300

Phe Gln Asp Cys Asn Lys Leu Val Asp Pro Glu Pro Tyr Leu Asp Val
305                 310                 315                 320
```

-continued

Cys Ile Tyr Asp Thr Cys Ser Cys Glu Ser Ile Gly Asp Cys Ala Cys
                325                 330                 335

Phe Cys Asp Thr Ile Ala Ala Tyr Ala His Val Cys Ala Gln His Gly
            340                 345                 350

Lys Val Val Thr Trp Arg Thr Ala Thr Leu Cys Pro Gln Ser Cys Glu
        355                 360                 365

Glu Arg Asn Leu Arg Glu Asn Gly Tyr Glu Cys Glu Trp Arg Tyr Asn
    370                 375                 380

Ser Cys Ala Pro Ala Cys Gln Val Thr Cys Gln His Pro Glu Pro Leu
385                 390                 395                 400

Ala Cys Pro Val Gln Cys Val Glu Gly Cys His Ala His Cys Pro Pro
            405                 410                 415

Gly Lys Ile Leu Asp Glu Leu Leu Gln Thr Cys Val Asp Pro Glu Asp
        420                 425                 430

Cys Pro Val Cys Glu Val Ala Gly Arg Arg Phe Ala Ser Gly Lys Lys
    435                 440                 445

Val Thr Leu Asn Pro Ser Asp Pro Glu His Cys Gln Ile Cys His Cys
450                 455                 460

Asp Val Val Asn Leu Thr Cys Glu Ala Cys Gln Glu Pro Gly Gly Ser
465                 470                 475                 480

Ser Gly Gly Ser Gly Gly Ser Gly Gly Ser Gly Gly Ser Gly Gly Ser
            485                 490                 495

Gly Gly Ser Gly Gly Ser Gly Gly Ser Gly Gly Ser Gly Ser Asp Ala
        500                 505                 510

His Lys Ser Glu Val Ala His Arg Phe Lys Asp Leu Gly Glu Glu Asn
    515                 520                 525

Phe Lys Ala Leu Val Leu Ile Ala Phe Ala Gln Tyr Leu Gln Gln Cys
    530                 535                 540

Pro Phe Glu Asp His Val Lys Leu Val Asn Glu Val Thr Glu Phe Ala
545                 550                 555                 560

Lys Thr Cys Val Ala Asp Glu Ser Ala Glu Asn Cys Asp Lys Ser Leu
            565                 570                 575

His Thr Leu Phe Gly Asp Lys Leu Cys Thr Val Ala Thr Leu Arg Glu
        580                 585                 590

Thr Tyr Gly Glu Met Ala Asp Cys Cys Ala Lys Gln Glu Pro Glu Arg
    595                 600                 605

Asn Glu Cys Phe Leu Gln His Lys Asp Asp Asn Pro Asn Leu Pro Arg
    610                 615                 620

Leu Val Arg Pro Glu Val Asp Val Met Cys Thr Ala Phe His Asp Asn
625                 630                 635                 640

Glu Glu Thr Phe Leu Lys Lys Tyr Leu Tyr Glu Ile Ala Arg Arg His
            645                 650                 655

Pro Tyr Phe Tyr Ala Pro Glu Leu Leu Phe Phe Ala Lys Arg Tyr Lys
        660                 665                 670

Ala Ala Phe Thr Glu Cys Cys Gln Ala Ala Asp Lys Ala Ala Cys Leu
    675                 680                 685

Leu Pro Lys Leu Asp Glu Leu Arg Asp Glu Gly Lys Ala Ser Ser Ala
    690                 695                 700

Lys Gln Arg Leu Lys Cys Ala Ser Leu Gln Lys Phe Gly Glu Arg Ala
705                 710                 715                 720

Phe Lys Ala Trp Ala Val Ala Arg Leu Ser Gln Arg Phe Pro Lys Ala
            725                 730                 735

Glu Phe Ala Glu Val Ser Lys Leu Val Thr Asp Leu Thr Lys Val His

```
                    740                 745                 750
Thr Glu Cys Cys His Gly Asp Leu Leu Glu Cys Ala Asp Asp Arg Ala
            755                 760                 765
Asp Leu Ala Lys Tyr Ile Cys Glu Asn Gln Asp Ser Ile Ser Ser Lys
        770                 775                 780
Leu Lys Glu Cys Cys Glu Lys Pro Leu Leu Glu Lys Ser His Cys Ile
785                 790                 795                 800
Ala Glu Val Glu Asn Asp Glu Met Pro Ala Asp Leu Pro Ser Leu Ala
                805                 810                 815
Ala Asp Phe Val Glu Ser Lys Asp Val Cys Lys Asn Tyr Ala Glu Ala
            820                 825                 830
Lys Asp Val Phe Leu Gly Met Phe Leu Tyr Glu Tyr Ala Arg Arg His
        835                 840                 845
Pro Asp Tyr Ser Val Val Leu Leu Leu Arg Leu Ala Lys Thr Tyr Glu
    850                 855                 860
Thr Thr Leu Glu Lys Cys Cys Ala Ala Ala Asp Pro His Glu Cys Tyr
865                 870                 875                 880
Ala Lys Val Phe Asp Glu Phe Lys Pro Leu Val Glu Glu Pro Gln Asn
                885                 890                 895
Leu Ile Lys Gln Asn Cys Glu Leu Phe Glu Gln Leu Gly Glu Tyr Lys
            900                 905                 910
Phe Gln Asn Ala Leu Leu Val Arg Tyr Thr Lys Lys Val Pro Gln Val
        915                 920                 925
Ser Thr Pro Thr Leu Val Glu Val Ser Arg Asn Leu Gly Lys Val Gly
    930                 935                 940
Ser Lys Cys Cys Lys His Pro Glu Ala Lys Arg Met Pro Cys Ala Glu
945                 950                 955                 960
Asp Tyr Leu Ser Val Val Leu Asn Gln Leu Cys Val Leu His Glu Lys
                965                 970                 975
Thr Pro Val Ser Asp Arg Val Thr Lys Cys Cys Thr Glu Ser Leu Val
            980                 985                 990
Asn Arg Arg Pro Cys Phe Ser Ala  Leu Glu Val Asp Glu  Thr Tyr Val
        995                 1000                1005
Pro Lys  Glu Phe Asn Ala Glu  Thr Phe Thr Phe His  Ala Asp Ile
    1010                1015                1020
Cys Thr  Leu Ser Glu Lys Glu  Arg Gln Ile Lys Lys  Gln Thr Ala
    1025                1030                1035
Leu Val  Glu Leu Val Lys His  Lys Pro Lys Ala Thr  Lys Glu Gln
    1040                1045                1050
Leu Lys  Ala Val Met Asp Asp  Phe Ala Ala Phe Val  Glu Lys Cys
    1055                1060                1065
Cys Lys  Ala Asp Asp Lys Glu  Thr Cys Phe Ala Glu  Glu Gly Lys
    1070                1075                1080
Lys Leu  Val Ala Ala Ser Gln  Ala Ala Leu Gly Leu
    1085                1090                1095

<210> SEQ ID NO 3
<211> LENGTH: 18
<212> TYPE: DNA
<213> ORGANISM: Artificial Sequence
<220> FEATURE:
<223> OTHER INFORMATION: PCR primer alpha-2,6 sialyltransferase

<400> SEQUENCE: 3
ggacctgaag gcctgccg                                                    18
```

<210> SEQ ID NO 4
<211> LENGTH: 21
<212> TYPE: DNA
<213> ORGANISM: Artificial Sequence
<220> FEATURE:
<223> OTHER INFORMATION: PCR primer  alpha-2,6 sialyltransferase

<400> SEQUENCE: 4

```
aggaaaatgt tcttcccagg c                                              21
```

<210> SEQ ID NO 5
<211> LENGTH: 37
<212> TYPE: DNA
<213> ORGANISM: Artificial Sequence
<220> FEATURE:
<223> OTHER INFORMATION: Nested PCR primer  alpha-2,6 sialyltransferase

<400> SEQUENCE: 5

```
gcggctagcg ccaccatgat tcacaccaac ctgaaga                             37
```

<210> SEQ ID NO 6
<211> LENGTH: 31
<212> TYPE: DNA
<213> ORGANISM: Artificial Sequence
<220> FEATURE:
<223> OTHER INFORMATION: Nested PCR primer alpha-2,6 sialyltransferase

<400> SEQUENCE: 6

```
cgcggatccc tagcagtgaa tggtccggaa g                                   31
```

<210> SEQ ID NO 7
<211> LENGTH: 1221
<212> TYPE: DNA
<213> ORGANISM: Homo sapiens

<400> SEQUENCE: 7

```
atgattcaca ccaacctgaa gaaaaagttc agctgctgcg tcctggtctt tcttctgttt    60
gcagtcatct gtgtgtggaa ggaaaagaag aaagggagtt actatgattc ctttaaattg   120
caaaccaagg aattccaggt gttaaagagt ctggggaaat tggccatggg gtctgattcc   180
cagtctgtat cctcaagcag cacccaggac ccccacaggg gccgccagac cctcggcagt   240
ctcagaggcc tagccaaggc caaaccagag gcctccttcc aggtgtggaa caaggacagc   300
tcttccaaaa accttatccc taggctgcaa aagatctgga gaattaccct aagcatgaac   360
aagtacaaag tgtcctacaa ggggccagga ccaggcatca agttcagtgc agaggccctg   420
cgctgccacc tccgggacca tgtgaatgta tccatggtag aggtcacaga ttttccttc    480 aatacctctg aatgggaggg ttatctgccc aaggagagca ttaggaccaa ggctgggcct   540
tggggcaggt gtgctgttgt gtcgtcagcg ggatctctga agtcctccca actaggcaga   600
gaaatcgatg atcatgacgc agtcctgagg tttaatgggg cacccacagc caacttccaa   660
caagatgtgg gcacaaaaac taccattcgc ctgatgaact ctcagttggt taccacagag   720
aagcgcttcc tcaaagacag tttgtacaat gaaggaatcc taattgtatg ggacccatct   780
gtataccact cagatatccc aaagtggtac cagaatccgg attataattt ctttaacaac   840
tacaagactt atcgtaagct gcaccccaat cagcctttt acatcctcaa gccccagatg   900
ccttgggagc tatgggacat tcttcaagaa atctccccag aagagattca gccaaacccc   960
ccatcctctg ggatgcttgg tatcatcatc atgatgacgc tgtgtgacca ggtggatatt  1020
```

```
tatgagttcc tcccatccaa gcgcaagact gacgtgtgct actactacca gaagttcttc    1080
gatagtgcct gcacgatggg tgcctaccac ccgctgctct atgagaagaa tttggtgaag    1140
catctcaacc agggcacaga tgaggacatc tacctgcttg aaaagccac  actgcctggc    1200 ttccggacca ttcactgcta a                                              1221
```

```
<210> SEQ ID NO 8
<211> LENGTH: 8442
<212> TYPE: DNA
<213> ORGANISM: Homo sapiens
<220> FEATURE:
<221> NAME/KEY: CDS
<222> LOCATION: (1)..(8442)

<400> SEQUENCE: 8
```

| | | | | | | | | | | | | | | | | |
|---|---|---|---|---|---|---|---|---|---|---|---|---|---|---|---|---|
| atg | att | cct | gcc | aga | ttt | gcc | ggg | gtg | ctg | ctt | gct | ctg | gcc | ctc | att | 48 |
| Met | Ile | Pro | Ala | Arg | Phe | Ala | Gly | Val | Leu | Leu | Ala | Leu | Ala | Leu | Ile | |
| 1 | | | | 5 | | | | | 10 | | | | | 15 | | |
| ttg | cca | ggg | acc | ctt | tgt | gca | gaa | gga | act | cgc | ggc | agg | tca | tcc | acg | 96 |
| Leu | Pro | Gly | Thr | Leu | Cys | Ala | Glu | Gly | Thr | Arg | Gly | Arg | Ser | Ser | Thr | |
| | | | 20 | | | | | 25 | | | | | 30 | | | |
| gcc | cga | tgc | agc | ctt | ttc | gga | agt | gac | ttc | gtc | aac | acc | ttt | gat | ggg | 144 |
| Ala | Arg | Cys | Ser | Leu | Phe | Gly | Ser | Asp | Phe | Val | Asn | Thr | Phe | Asp | Gly | |
| | 35 | | | | | 40 | | | | | 45 | | | | | |
| agc | atg | tac | agc | ttt | gcg | gga | tac | tgc | agt | tac | ctc | ctg | gca | ggg | ggc | 192 |
| Ser | Met | Tyr | Ser | Phe | Ala | Gly | Tyr | Cys | Ser | Tyr | Leu | Leu | Ala | Gly | Gly | |
| 50 | | | | | 55 | | | | | 60 | | | | | | |
| tgc | cag | aaa | cgc | tcc | ttc | tcg | att | att | ggg | gac | ttc | cag | aat | ggc | aag | 240 |
| Cys | Gln | Lys | Arg | Ser | Phe | Ser | Ile | Ile | Gly | Asp | Phe | Gln | Asn | Gly | Lys | |
| 65 | | | | 70 | | | | | 75 | | | | | 80 | | |
| aga | gtg | agc | ctc | tcc | gtg | tat | ctt | ggg | gaa | ttt | ttt | gac | atc | cat | ttg | 288 |
| Arg | Val | Ser | Leu | Ser | Val | Tyr | Leu | Gly | Glu | Phe | Phe | Asp | Ile | His | Leu | |
| | | | | 85 | | | | | 90 | | | | | 95 | | |
| ttt | gtc | aat | ggt | acc | gtg | aca | cag | ggg | gac | caa | aga | gtc | tcc | atg | ccc | 336 |
| Phe | Val | Asn | Gly | Thr | Val | Thr | Gln | Gly | Asp | Gln | Arg | Val | Ser | Met | Pro | |
| | | | 100 | | | | | 105 | | | | | 110 | | | |
| tat | gcc | tcc | aaa | ggg | ctg | tat | cta | gaa | act | gag | gct | ggg | tac | tac | aag | 384 |
| Tyr | Ala | Ser | Lys | Gly | Leu | Tyr | Leu | Glu | Thr | Glu | Ala | Gly | Tyr | Tyr | Lys | |
| | 115 | | | | | 120 | | | | | 125 | | | | | |
| ctg | tcc | ggt | gag | gcc | tat | ggc | ttt | gtg | gcc | agg | atc | gat | ggc | agc | ggc | 432 |
| Leu | Ser | Gly | Glu | Ala | Tyr | Gly | Phe | Val | Ala | Arg | Ile | Asp | Gly | Ser | Gly | |
| 130 | | | | | 135 | | | | | 140 | | | | | | |
| aac | ttt | caa | gtc | ctg | ctg | tca | gac | aga | tac | ttc | aac | aag | acc | tgc | ggg | 480 |
| Asn | Phe | Gln | Val | Leu | Leu | Ser | Asp | Arg | Tyr | Phe | Asn | Lys | Thr | Cys | Gly | |
| 145 | | | | 150 | | | | | 155 | | | | | 160 | | |
| ctg | tgt | ggc | aac | ttt | aac | atc | ttt | gct | gaa | gat | gac | ttt | atg | acc | caa | 528 |
| Leu | Cys | Gly | Asn | Phe | Asn | Ile | Phe | Ala | Glu | Asp | Asp | Phe | Met | Thr | Gln | |
| | | | | 165 | | | | | 170 | | | | | 175 | | |
| gaa | ggg | acc | ttg | acc | tcg | gac | cct | tat | gac | ttt | gcc | aac | tca | tgg | gct | 576 |
| Glu | Gly | Thr | Leu | Thr | Ser | Asp | Pro | Tyr | Asp | Phe | Ala | Asn | Ser | Trp | Ala | |
| | | | 180 | | | | | 185 | | | | | 190 | | | |
| ctg | agc | agt | gga | gaa | cag | tgg | tgt | gaa | cgg | gca | tct | cct | ccc | agc | agc | 624 |
| Leu | Ser | Ser | Gly | Glu | Gln | Trp | Cys | Glu | Arg | Ala | Ser | Pro | Pro | Ser | Ser | |
| | | 195 | | | | | 200 | | | | | 205 | | | | |
| tca | tgc | aac | atc | tcc | tct | ggg | gaa | atg | cag | aag | ggc | ctg | tgg | gag | cag | 672 |
| Ser | Cys | Asn | Ile | Ser | Ser | Gly | Glu | Met | Gln | Lys | Gly | Leu | Trp | Glu | Gln | |
| 210 | | | | | 215 | | | | | 220 | | | | | | |
| tgc | cag | ctt | ctg | aag | agc | acc | tcg | gtg | ttt | gcc | cgc | tgc | cac | cct | ctg | 720 |
| Cys | Gln | Leu | Leu | Lys | Ser | Thr | Ser | Val | Phe | Ala | Arg | Cys | His | Pro | Leu | |
| 225 | | | | 230 | | | | | 235 | | | | | 240 | | |

-continued

| | | |
|---|---|---|
| gtg gac ccc gag cct ttt gtg gcc ctg tgt gag aag act ttg tgt gag<br>Val Asp Pro Glu Pro Phe Val Ala Leu Cys Glu Lys Thr Leu Cys Glu<br>245                          250                      255 | | 768 |
| tgt gct ggg ggg ctg gag tgc gcc tgc cct gcc ctc ctg gag tac gcc<br>Cys Ala Gly Gly Leu Glu Cys Ala Cys Pro Ala Leu Leu Glu Tyr Ala<br>                260                      265                      270 | | 816 |
| cgg acc tgt gcc cag gag gga atg gtg ctg tac ggc tgg acc gac cac<br>Arg Thr Cys Ala Gln Glu Gly Met Val Leu Tyr Gly Trp Thr Asp His<br>        275                      280                      285 | | 864 |
| agc gcg tgc agc cca gtg tgc cct gct ggt atg gag tat agg cag tgt<br>Ser Ala Cys Ser Pro Val Cys Pro Ala Gly Met Glu Tyr Arg Gln Cys<br>        290                      295                      300 | | 912 |
| gtg tcc cct tgc gcc agg acc tgc cag agc ctg cac atc aat gaa atg<br>Val Ser Pro Cys Ala Arg Thr Cys Gln Ser Leu His Ile Asn Glu Met<br>305                        310                      315                      320 | | 960 |
| tgt cag gag cga tgc gtg gat ggc tgc agc tgc cct gag gga cag ctc<br>Cys Gln Glu Arg Cys Val Asp Gly Cys Ser Cys Pro Glu Gly Gln Leu<br>                325                      330                      335 | | 1008 |
| ctg gat gaa ggc ctc tgc gtg gag agc acc gag tgt ccc tgc gtg cat<br>Leu Asp Glu Gly Leu Cys Val Glu Ser Thr Glu Cys Pro Cys Val His<br>        340                      345                      350 | | 1056 |
| tcc gga aag cgc tac cct ccc ggc acc tcc ctc tct cga gac tgc aac<br>Ser Gly Lys Arg Tyr Pro Pro Gly Thr Ser Leu Ser Arg Asp Cys Asn<br>        355                      360                      365 | | 1104 |
| acc tgc att tgc cga aac agc cag tgg atc tgc agc aat gaa gaa tgt<br>Thr Cys Ile Cys Arg Asn Ser Gln Trp Ile Cys Ser Asn Glu Glu Cys<br>370                        375                      380 | | 1152 |
| cca ggg gag tgc ctt gtc aca ggt caa tca cac ttc aag agc ttt gac<br>Pro Gly Glu Cys Leu Val Thr Gly Gln Ser His Phe Lys Ser Phe Asp<br>385                        390                      395                      400 | | 1200 |
| aac aga tac ttc acc ttc agt ggg atc tgc cag tac ctg ctg gcc cgg<br>Asn Arg Tyr Phe Thr Phe Ser Gly Ile Cys Gln Tyr Leu Leu Ala Arg<br>                405                      410                      415 | | 1248 |
| gat tgc cag gac cac tcc ttc tcc att gtc att gag act gtc cag tgt<br>Asp Cys Gln Asp His Ser Phe Ser Ile Val Ile Glu Thr Val Gln Cys<br>                    420                      425                      430 | | 1296 |
| gct gat gac cgc gac gct gtg tgc acc cgc tcc gtc acc gtc cgg ctg<br>Ala Asp Asp Arg Asp Ala Val Cys Thr Arg Ser Val Thr Val Arg Leu<br>        435                      440                      445 | | 1344 |
| cct ggc ctg cac aac agc ctt gtg aaa ctg aag cat ggg gca gga gtt<br>Pro Gly Leu His Asn Ser Leu Val Lys Leu Lys His Gly Ala Gly Val<br>450                        455                      460 | | 1392 |
| gcc atg gat ggc cag gac gtc cag ctc ccc ctc ctg aaa ggt gac ctc<br>Ala Met Asp Gly Gln Asp Val Gln Leu Pro Leu Leu Lys Gly Asp Leu<br>465                        470                      475                      480 | | 1440 |
| cgc atc cag cat aca gtg acg gcc tcc gtg cgc ctc agc tac ggg gag<br>Arg Ile Gln His Thr Val Thr Ala Ser Val Arg Leu Ser Tyr Gly Glu<br>                485                      490                      495 | | 1488 |
| gac ctg cag atg gac tgg gat ggc cgc ggg agg ctg ctg gtg aag ctg<br>Asp Leu Gln Met Asp Trp Asp Gly Arg Gly Arg Leu Leu Val Lys Leu<br>        500                      505                      510 | | 1536 |
| tcc ccc gtc tat gcc ggg aag acc tgc ggc ctg tgt ggg aat tac aat<br>Ser Pro Val Tyr Ala Gly Lys Thr Cys Gly Leu Cys Gly Asn Tyr Asn<br>        515                      520                      525 | | 1584 |
| ggc aac cag ggc gac gac ttc ctt acc ccc tct ggg ctg gcg gag ccc<br>Gly Asn Gln Gly Asp Asp Phe Leu Thr Pro Ser Gly Leu Ala Glu Pro<br>530                        535                      540 | | 1632 |
| cgg gtg gag gac ttc ggg aac gcc tgg aag ctg cac ggg gac tgc cag<br>Arg Val Glu Asp Phe Gly Asn Ala Trp Lys Leu His Gly Asp Cys Gln<br>545                        550                      555                      560 | | 1680 |

```
gac ctg cag aag cag cac agc gat ccc tgc gcc ctc aac ccg cgc atg      1728
Asp Leu Gln Lys Gln His Ser Asp Pro Cys Ala Leu Asn Pro Arg Met
                    565                 570                 575 acc agg ttc tcc gag gag gcg tgc gcg gtc ctg acg tcc ccc aca ttc      1776
Thr Arg Phe Ser Glu Glu Ala Cys Ala Val Leu Thr Ser Pro Thr Phe
            580                 585                 590 gag gcc tgc cat cgt gcc gtc agc ccg ctg ccc tac ctg cgg aac tgc      1824
Glu Ala Cys His Arg Ala Val Ser Pro Leu Pro Tyr Leu Arg Asn Cys
        595                 600                 605 cgc tac gac gtg tgc tcc tgc tcg gac ggc cgc gag tgc ctg tgc ggc      1872
Arg Tyr Asp Val Cys Ser Cys Ser Asp Gly Arg Glu Cys Leu Cys Gly
    610                 615                 620 gcc ctg gcc agc tat gcc gcg gcc tgc gcg ggg aga ggc gtg cgc gtc      1920
Ala Leu Ala Ser Tyr Ala Ala Ala Cys Ala Gly Arg Gly Val Arg Val
625                 630                 635                 640 gcg tgg cgc gag cca ggc cgc tgt gag ctg aac tgc ccg aaa ggc cag      1968
Ala Trp Arg Glu Pro Gly Arg Cys Glu Leu Asn Cys Pro Lys Gly Gln
                645                 650                 655 gtg tac ctg cag tgc ggg acc ccc tgc aac ctg acc tgc cgc tct ctc      2016
Val Tyr Leu Gln Cys Gly Thr Pro Cys Asn Leu Thr Cys Arg Ser Leu
            660                 665                 670 tct tac ccg gat gag gaa tgc aat gag gcc tgc ctg gag ggc tgc ttc      2064
Ser Tyr Pro Asp Glu Glu Cys Asn Glu Ala Cys Leu Glu Gly Cys Phe
        675                 680                 685 tgc ccc cca ggg ctc tac atg gat gag agg ggg gac tgc gtg ccc aag      2112
Cys Pro Pro Gly Leu Tyr Met Asp Glu Arg Gly Asp Cys Val Pro Lys
    690                 695                 700 gcc cag tgc ccc tgt tac tat gac ggt gag atc ttc cag cca gaa gac      2160
Ala Gln Cys Pro Cys Tyr Tyr Asp Gly Glu Ile Phe Gln Pro Glu Asp
705                 710                 715                 720 atc ttc tca gac cat cac acc atg tgc tac tgt gag gat ggc ttc atg      2208
Ile Phe Ser Asp His His Thr Met Cys Tyr Cys Glu Asp Gly Phe Met
                725                 730                 735 cac tgt acc atg agt gga gtc ccc gga agc ttg ctg cct gac gct gtc      2256
His Cys Thr Met Ser Gly Val Pro Gly Ser Leu Leu Pro Asp Ala Val
            740                 745                 750 ctc agc agt ccc ctg tct cat cgc agc aaa agg agc cta tcc tgt cgg      2304
Leu Ser Ser Pro Leu Ser His Arg Ser Lys Arg Ser Leu Ser Cys Arg
        755                 760                 765 ccc ccc atg gtc aag ctg gtg tgt ccc gct gac aac ctg cgg gct gaa      2352
Pro Pro Met Val Lys Leu Val Cys Pro Ala Asp Asn Leu Arg Ala Glu
    770                 775                 780 ggg ctc gag tgt acc aaa acg tgc cag aac tat gac ctg gag tgc atg      2400
Gly Leu Glu Cys Thr Lys Thr Cys Gln Asn Tyr Asp Leu Glu Cys Met
785                 790                 795                 800 agc atg ggc tgt gtc tct ggc tgc ctc tgc ccc ccg ggc atg gtc cgg      2448
Ser Met Gly Cys Val Ser Gly Cys Leu Cys Pro Pro Gly Met Val Arg
                805                 810                 815 cat gag aac aga tgt gtg gcc ctg gaa agg tgt ccc tgc ttc cat cag      2496
His Glu Asn Arg Cys Val Ala Leu Glu Arg Cys Pro Cys Phe His Gln
            820                 825                 830 ggc aag gag tat gcc cct gga gaa aca gtg aag att ggc tgc aac act      2544
Gly Lys Glu Tyr Ala Pro Gly Glu Thr Val Lys Ile Gly Cys Asn Thr
        835                 840                 845 tgt gtc tgt cgg gac cgg aag tgg aac tgc aca gac cat gtg tgt gat      2592
Cys Val Cys Arg Asp Arg Lys Trp Asn Cys Thr Asp His Val Cys Asp
    850                 855                 860 gcc acg tgc tcc acg atc ggc atg gcc cac tac ctc acc ttc gac ggg      2640
Ala Thr Cys Ser Thr Ile Gly Met Ala His Tyr Leu Thr Phe Asp Gly
```

-continued

```
      865                 870                 875                 880
ctc aaa tac ctg ttc ccc ggg gag tgc cag tac gtt ctg gtg cag gat    2688
Leu Lys Tyr Leu Phe Pro Gly Glu Cys Gln Tyr Val Leu Val Gln Asp
                    885                 890                 895 tac tgc ggc agt aac cct ggg acc ttt cgg atc cta gtg ggg aat aag    2736
Tyr Cys Gly Ser Asn Pro Gly Thr Phe Arg Ile Leu Val Gly Asn Lys
                900                 905                 910 gga tgc agc cac ccc tca gtg aaa tgc aag aaa cgg gtc acc atc ctg    2784
Gly Cys Ser His Pro Ser Val Lys Cys Lys Lys Arg Val Thr Ile Leu
            915                 920                 925 gtg gag gga gga gag att gag ctg ttt gac ggg gag gtg aat gtg aag    2832
Val Glu Gly Gly Glu Ile Glu Leu Phe Asp Gly Glu Val Asn Val Lys
        930                 935                 940 agg ccc atg aag gat gag act cac ttt gag gtg gtg gag tct ggc cgg    2880
Arg Pro Met Lys Asp Glu Thr His Phe Glu Val Val Glu Ser Gly Arg
945                 950                 955                 960 tac atc att ctg ctg ctg ggc aaa gcc ctc tcc gtg gtc tgg gac cgc    2928
Tyr Ile Ile Leu Leu Leu Gly Lys Ala Leu Ser Val Val Trp Asp Arg
                965                 970                 975 cac ctg agc atc tcc gtg gtc ctg aag cag aca tac cag gag aaa gtg    2976
His Leu Ser Ile Ser Val Val Leu Lys Gln Thr Tyr Gln Glu Lys Val
                980                 985                 990 tgt ggc ctg tgt ggg aat ttt gat  ggc atc cag aac aat  gac ctc acc   3024
Cys Gly Leu Cys Gly Asn Phe Asp  Gly Ile Gln Asn Asn  Asp Leu Thr
            995                 1000                1005 agc agc  aac ctc caa gtg gag  gaa gac cct gtg gac  ttt ggg aac      3069
Ser Ser  Asn Leu Gln Val Glu  Glu Asp Pro Val Asp  Phe Gly Asn
        1010                1015                1020 tcc tgg aaa gtg agc tcg cag tgt gct gac acc aga aaa gtg cct         3114
Ser Trp Lys Val Ser Ser Gln Cys Ala Asp Thr Arg Lys Val Pro
    1025                1030                1035 ctg gac tca tcc cct gcc acc tgc cat aac aac atc atg aag cag         3159
Leu Asp Ser Ser Pro Ala Thr Cys His Asn Asn Ile Met Lys Gln
    1040                1045                1050 acg atg gtg gat tcc tcc tgt aga atc ctt acc agt gac gtc ttc         3204
Thr Met Val Asp Ser Ser Cys Arg Ile Leu Thr Ser Asp Val Phe
    1055                1060                1065 cag gac tgc aac aag ctg gtg gac ccc gag cca tat ctg gat gtc         3249
Gln Asp Cys Asn Lys Leu Val Asp Pro Glu Pro Tyr Leu Asp Val
    1070                1075                1080 tgc att tac gac acc tgc tcc tgt gag tcc att ggg gac tgc gcc         3294
Cys Ile Tyr Asp Thr Cys Ser Cys Glu Ser Ile Gly Asp Cys Ala
    1085                1090                1095 tgc ttc tgc gac acc att gct gcc tat gcc cac gtg tgt gcc cag         3339
Cys Phe Cys Asp Thr Ile Ala Ala Tyr Ala His Val Cys Ala Gln
    1100                1105                1110 cat ggc aag gtg gtg acc tgg agg acg gcc aca ttg tgc ccc cag         3384
His Gly Lys Val Val Thr Trp Arg Thr Ala Thr Leu Cys Pro Gln
    1115                1120                1125 agc tgc gag gag agg aat ctc cgg gag aac ggg tat gag tgt gag         3429
Ser Cys Glu Glu Arg Asn Leu Arg Glu Asn Gly Tyr Glu Cys Glu
    1130                1135                1140 tgg cgc tat aac agc tgt gca cct gcc tgt caa gtc acg tgt cag         3474
Trp Arg Tyr Asn Ser Cys Ala Pro Ala Cys Gln Val Thr Cys Gln
    1145                1150                1155 cac cct gag cca ctg gcc tgc cct gtg cag tgt gtg gag ggc tgc         3519
His Pro Glu Pro Leu Ala Cys Pro Val Gln Cys Val Glu Gly Cys
    1160                1165                1170 cat gcc  cac tgc cct cca ggg  aaa atc ctg gat gag  ctt ttg cag      3564
```

-continued

| | | | | | | | | | | | | | |
|---|---|---|---|---|---|---|---|---|---|---|---|---|---|
| His | Ala | His | Cys | Pro | Pro | Gly | Lys | Ile | Leu | Asp | Glu | Leu | Leu | Gln |
| 1175 | | | | | 1180 | | | | | 1185 | | | | | acc tgc gtt gac cct gaa gac tgt cca gtg tgt gag gtg gct ggc          3609
Thr Cys Val Asp Pro Glu Asp Cys Pro Val Cys Glu Val Ala Gly
1190                1195                1200 cgg cgt ttt gcc tca gga aag aaa gtc acc ttg aat ccc agt gac          3654
Arg Arg Phe Ala Ser Gly Lys Lys Val Thr Leu Asn Pro Ser Asp
1205                1210                1215 cct gag cac tgc cag att tgc cac tgt gat gtt gtc aac ctc acc          3699
Pro Glu His Cys Gln Ile Cys His Cys Asp Val Val Asn Leu Thr
1220                1225                1230 tgt gaa gcc tgc cag gag ccg gga ggc ctg gtg gtg cct ccc aca          3744
Cys Glu Ala Cys Gln Glu Pro Gly Gly Leu Val Val Pro Pro Thr
1235                1240                1245 gat gcc ccg gtg agc ccc acc act ctg tat gtg gag gac atc tcg          3789
Asp Ala Pro Val Ser Pro Thr Thr Leu Tyr Val Glu Asp Ile Ser
1250                1255                1260 gaa ccg ccg ttg cac gat ttc tac tgc agc agg cta ctg gac ctg          3834
Glu Pro Pro Leu His Asp Phe Tyr Cys Ser Arg Leu Leu Asp Leu
1265                1270                1275 gtc ttc ctg ctg gat ggc tcc tcc agg ctg tcc gag gct gag ttt          3879
Val Phe Leu Leu Asp Gly Ser Ser Arg Leu Ser Glu Ala Glu Phe
1280                1285                1290 gaa gtg ctg aag gcc ttt gtg gtg gac atg atg gag cgg ctg cgc          3924
Glu Val Leu Lys Ala Phe Val Val Asp Met Met Glu Arg Leu Arg
1295                1300                1305 atc tcc cag aag tgg gtc cgc gtg gcc gtg gtg gag tac cac gac          3969
Ile Ser Gln Lys Trp Val Arg Val Ala Val Val Glu Tyr His Asp
1310                1315                1320 ggc tcc cac gcc tac atc ggg ctc aag gac cgg aag cga ccg tca          4014
Gly Ser His Ala Tyr Ile Gly Leu Lys Asp Arg Lys Arg Pro Ser
1325                1330                1335 gag ctg cgg cgc att gcc agc cag gtg aag tat gcg ggc agc cag          4059
Glu Leu Arg Arg Ile Ala Ser Gln Val Lys Tyr Ala Gly Ser Gln
1340                1345                1350 gtg gcc tcc acc agc gag gtc ttg aaa tac aca ctg ttc caa atc          4104
Val Ala Ser Thr Ser Glu Val Leu Lys Tyr Thr Leu Phe Gln Ile
1355                1360                1365 ttc agc aag atc gac cgc cct gaa gcc tcc cgc atc gcc ctg ctc          4149
Phe Ser Lys Ile Asp Arg Pro Glu Ala Ser Arg Ile Ala Leu Leu
1370                1375                1380 ctg atg gcc agc cag gag ccc caa cgg atg tcc cgg aac ttt gtc          4194
Leu Met Ala Ser Gln Glu Pro Gln Arg Met Ser Arg Asn Phe Val
1385                1390                1395 cgc tac gtc cag ggc ctg aag aag aag aag gtc att gtg atc ccg          4239
Arg Tyr Val Gln Gly Leu Lys Lys Lys Lys Val Ile Val Ile Pro
1400                1405                1410 gtg ggc att ggg ccc cat gcc aac ctc aag cag atc cgc ctc atc          4284
Val Gly Ile Gly Pro His Ala Asn Leu Lys Gln Ile Arg Leu Ile
1415                1420                1425 gag aag cag gcc cct gag aac aag gcc ttc gtg ctg agc agt gtg          4329
Glu Lys Gln Ala Pro Glu Asn Lys Ala Phe Val Leu Ser Ser Val
1430                1435                1440 gat gag ctg gag cag caa agg gac gag atc gtt agc tac ctc tgt          4374
Asp Glu Leu Glu Gln Gln Arg Asp Glu Ile Val Ser Tyr Leu Cys
1445                1450                1455 gac ctt gcc cct gaa gcc cct cct cct act ctg ccc ccc cac atg          4419
Asp Leu Ala Pro Glu Ala Pro Pro Pro Thr Leu Pro Pro His Met
1460                1465                1470

```
gca caa gtc act gtg ggc ccg ggg ctc ttg ggg gtt tcg acc ctg      4464
Ala Gln Val Thr Val Gly Pro Gly Leu Leu Gly Val Ser Thr Leu
    1475            1480                1485 ggg ccc aag agg aac tcc atg gtt ctg gat gtg gcg ttc gtc ctg      4509
Gly Pro Lys Arg Asn Ser Met Val Leu Asp Val Ala Phe Val Leu
    1490            1495                1500 gaa gga tcg gac aaa att ggt gaa gcc gac ttc aac agg agc aag      4554
Glu Gly Ser Asp Lys Ile Gly Glu Ala Asp Phe Asn Arg Ser Lys
    1505            1510                1515 gag ttc atg gag gag gtg att cag cgg atg gat gtg ggc cag gac      4599
Glu Phe Met Glu Glu Val Ile Gln Arg Met Asp Val Gly Gln Asp
    1520            1525                1530 agc atc cac gtc acg gtg ctg cag tac tcc tac atg gtg acc gtg      4644
Ser Ile His Val Thr Val Leu Gln Tyr Ser Tyr Met Val Thr Val
    1535            1540                1545 gag tac ccc ttc agc gag gca cag tcc aaa ggg gac atc ctg cag      4689
Glu Tyr Pro Phe Ser Glu Ala Gln Ser Lys Gly Asp Ile Leu Gln
    1550            1555                1560 cgg gtg cga gag atc cgc tac cag ggc ggc aac agg acc aac act      4734
Arg Val Arg Glu Ile Arg Tyr Gln Gly Gly Asn Arg Thr Asn Thr
    1565            1570                1575 ggg ctg gcc ctg cgg tac ctc tct gac cac agc ttc ttg gtc agc      4779
Gly Leu Ala Leu Arg Tyr Leu Ser Asp His Ser Phe Leu Val Ser
    1580            1585                1590 cag ggt gac cgg gag cag gcg ccc aac ctg gtc tac atg gtc acc      4824
Gln Gly Asp Arg Glu Gln Ala Pro Asn Leu Val Tyr Met Val Thr
    1595            1600                1605 gga aat cct gcc tct gat gag atc aag agg ctg cct gga gac atc      4869
Gly Asn Pro Ala Ser Asp Glu Ile Lys Arg Leu Pro Gly Asp Ile
    1610            1615                1620 cag gtg gtg ccc att gga gtg ggc cct aat gcc aac gtg cag gag      4914
Gln Val Val Pro Ile Gly Val Gly Pro Asn Ala Asn Val Gln Glu
    1625            1630                1635 ctg gag agg att ggc tgg ccc aat gcc cct atc ctc atc cag gac      4959
Leu Glu Arg Ile Gly Trp Pro Asn Ala Pro Ile Leu Ile Gln Asp
    1640            1645                1650 ttt gag acg ctc ccc cga gag gct cct gac ctg gtg ctg cag agg      5004
Phe Glu Thr Leu Pro Arg Glu Ala Pro Asp Leu Val Leu Gln Arg
    1655            1660                1665 tgc tgc tcc gga gag ggg ctg cag atc ccc acc ctc tcc cct gca      5049
Cys Cys Ser Gly Glu Gly Leu Gln Ile Pro Thr Leu Ser Pro Ala
    1670            1675                1680 cct gac tgc agc cag ccc ctg gac gtg atc ctt ctc ctg gat ggc      5094
Pro Asp Cys Ser Gln Pro Leu Asp Val Ile Leu Leu Leu Asp Gly
    1685            1690                1695 tcc tcc agt ttc cca gct tct tat ttt gat gaa atg aag agt ttc      5139
Ser Ser Ser Phe Pro Ala Ser Tyr Phe Asp Glu Met Lys Ser Phe
    1700            1705                1710 gcc aag gct ttc att tca aaa gcc aat ata ggg cct cgt ctc act      5184
Ala Lys Ala Phe Ile Ser Lys Ala Asn Ile Gly Pro Arg Leu Thr
    1715            1720                1725 cag gtg tca gtg ctg cag tat gga agc atc acc acc att gac gtg      5229
Gln Val Ser Val Leu Gln Tyr Gly Ser Ile Thr Thr Ile Asp Val
    1730            1735                1740 cca tgg aac gtg gtc ccg gag aaa gcc cat ttg ctg agc ctt gtg      5274
Pro Trp Asn Val Val Pro Glu Lys Ala His Leu Leu Ser Leu Val
    1745            1750                1755 gac gtc atg cag cgg gag gga ggc ccc agc caa atc ggg gat gcc      5319
Asp Val Met Gln Arg Glu Gly Gly Pro Ser Gln Ile Gly Asp Ala
    1760            1765                1770
```

-continued

| | | | | | | | | | | | | | | |
|---|---|---|---|---|---|---|---|---|---|---|---|---|---|---|
| ttg | ggc | ttt | gct | gtg | cga | tac | ttg | act | tca | gaa | atg | cat | ggg | gcg | 5364 |
| Leu | Gly | Phe | Ala | Val | Arg | Tyr | Leu | Thr | Ser | Glu | Met | His | Gly | Ala | |
| | 1775 | | | | 1780 | | | | 1785 | | | | | | | cgc ccg gga gcc tca aag gcg gtg gtc atc ctg gtc acg gac gtc  5409
Arg Pro Gly Ala Ser Lys Ala Val Val Ile Leu Val Thr Asp Val
    1790            1795              1800 tct gtg gat tca gtg gat gca gca gct gat gcc gcc agg tcc aac  5454
Ser Val Asp Ser Val Asp Ala Ala Ala Asp Ala Ala Arg Ser Asn
1805            1810              1815 aga gtg aca gtg ttc cct att gga att gga gat cgc tac gat gca  5499
Arg Val Thr Val Phe Pro Ile Gly Ile Gly Asp Arg Tyr Asp Ala
    1820            1825              1830 gcc cag cta cgg atc ttg gca ggc cca gca ggc gac tcc aac gtg  5544
Ala Gln Leu Arg Ile Leu Ala Gly Pro Ala Gly Asp Ser Asn Val
1835            1840              1845 gtg aag ctc cag cga atc gaa gac ctc cct acc atg gtc acc ttg  5589
Val Lys Leu Gln Arg Ile Glu Asp Leu Pro Thr Met Val Thr Leu
    1850            1855              1860 ggc aat tcc ttc ctc cac aaa ctg tgc tct gga ttt gtt agg att  5634
Gly Asn Ser Phe Leu His Lys Leu Cys Ser Gly Phe Val Arg Ile
1865            1870              1875 tgc atg gat gag gat ggg aat gag aag agg ccc ggg gac gtc tgg  5679
Cys Met Asp Glu Asp Gly Asn Glu Lys Arg Pro Gly Asp Val Trp
    1880            1885              1890 acc ttg cca gac cag tgc cac acc gtg act tgc cag cca gat ggc  5724
Thr Leu Pro Asp Gln Cys His Thr Val Thr Cys Gln Pro Asp Gly
1895            1900              1905 cag acc ttg ctg aag agt cat cgg gtc aac tgt gac cgg ggg ctg  5769
Gln Thr Leu Leu Lys Ser His Arg Val Asn Cys Asp Arg Gly Leu
    1910            1915              1920 agg cct tcg tgc cct aac agc cag tcc cct gtt aaa gtg gaa gag  5814
Arg Pro Ser Cys Pro Asn Ser Gln Ser Pro Val Lys Val Glu Glu
1925            1930              1935 acc tgt ggc tgc cgc tgg acc tgc ccc tgc gtg tgc aca ggc agc  5859
Thr Cys Gly Cys Arg Trp Thr Cys Pro Cys Val Cys Thr Gly Ser
    1940            1945              1950 tcc act cgg cac atc gtg acc ttt gat ggg cag aat ttc aag ctg  5904
Ser Thr Arg His Ile Val Thr Phe Asp Gly Gln Asn Phe Lys Leu
1955            1960              1965 act ggc agc tgt tct tat gtc cta ttt caa aac aag gag cag gac  5949
Thr Gly Ser Cys Ser Tyr Val Leu Phe Gln Asn Lys Glu Gln Asp
    1970            1975              1980 ctg gag gtg att ctc cat aat ggt gcc tgc agc cct gga gca agg  5994
Leu Glu Val Ile Leu His Asn Gly Ala Cys Ser Pro Gly Ala Arg
1985            1990              1995 cag ggc tgc atg aaa tcc atc gag gtg aag cac agt gcc ctc tcc  6039
Gln Gly Cys Met Lys Ser Ile Glu Val Lys His Ser Ala Leu Ser
    2000            2005              2010 gtc gag ctg cac agt gac atg gag gtg acg gtg aat ggg aga ctg  6084
Val Glu Leu His Ser Asp Met Glu Val Thr Val Asn Gly Arg Leu
2015            2020              2025 gtc tct gtt cct tac gtg ggt ggg aac atg gaa gtc aac gtt tat  6129
Val Ser Val Pro Tyr Val Gly Gly Asn Met Glu Val Asn Val Tyr
    2030            2035              2040 ggt gcc atc atg cat gag gtc aga ttc aat cac ctt ggt cac atc  6174
Gly Ala Ile Met His Glu Val Arg Phe Asn His Leu Gly His Ile
2045            2050              2055 ttc aca ttc act cca caa aac aat gag ttc caa ctg cag ctc agc  6219
Phe Thr Phe Thr Pro Gln Asn Asn Glu Phe Gln Leu Gln Leu Ser -continued

```
              2060              2065              2070 ccc aag act ttt gct tca aag acg tat ggt ctg tgt ggg atc tgt         6264
Pro Lys Thr Phe Ala Ser Lys Thr Tyr Gly Leu Cys Gly Ile Cys
2075              2080              2085 gat gag aac gga gcc aat gac ttc atg ctg agg gat ggc aca gtc         6309
Asp Glu Asn Gly Ala Asn Asp Phe Met Leu Arg Asp Gly Thr Val
2090              2095              2100 acc aca gac tgg aaa aca ctt gtt cag gaa tgg act gtg cag cgg         6354
Thr Thr Asp Trp Lys Thr Leu Val Gln Glu Trp Thr Val Gln Arg
2105              2110              2115 cca ggg cag acg tgc cag ccc atc ctg gag gag cag tgt ctt gtc         6399
Pro Gly Gln Thr Cys Gln Pro Ile Leu Glu Glu Gln Cys Leu Val
2120              2125              2130 ccc gac agc tcc cac tgc cag gtc ctc ctc tta cca ctg ttt gct         6444
Pro Asp Ser Ser His Cys Gln Val Leu Leu Leu Pro Leu Phe Ala
2135              2140              2145 gaa tgc cac aag gtc ctg gct cca gca aca ttc tat gcc atc tgc         6489
Glu Cys His Lys Val Leu Ala Pro Ala Thr Phe Tyr Ala Ile Cys
2150              2155              2160 cag cag gac agt tgc cac cag gag caa gtg tgt gag gtg atc gcc         6534
Gln Gln Asp Ser Cys His Gln Glu Gln Val Cys Glu Val Ile Ala
2165              2170              2175 tct tat gcc cac ctc tgt cgg acc aac ggg gtc tgc gtt gac tgg         6579
Ser Tyr Ala His Leu Cys Arg Thr Asn Gly Val Cys Val Asp Trp
2180              2185              2190 agg aca cct gat ttc tgt gct atg tca tgc cca cca tct ctg gtt         6624
Arg Thr Pro Asp Phe Cys Ala Met Ser Cys Pro Pro Ser Leu Val
2195              2200              2205 tat aac cac tgt gag cat ggc tgt ccc cgg cac tgt gat ggc aac         6669
Tyr Asn His Cys Glu His Gly Cys Pro Arg His Cys Asp Gly Asn
2210              2215              2220 gtg agc tcc tgt ggg gac cat ccc tcc gaa ggc tgt ttc tgc cct         6714
Val Ser Ser Cys Gly Asp His Pro Ser Glu Gly Cys Phe Cys Pro
2225              2230              2235 cca gat aaa gtc atg ttg gaa ggc agc tgt gtc cct gaa gag gcc         6759
Pro Asp Lys Val Met Leu Glu Gly Ser Cys Val Pro Glu Glu Ala
2240              2245              2250 tgc act cag tgc att ggt gag gat gga gtc cag cac cag ttc ctg         6804
Cys Thr Gln Cys Ile Gly Glu Asp Gly Val Gln His Gln Phe Leu
2255              2260              2265 gaa gcc tgg gtc ccg gac cac cag ccc tgt cag atc tgc aca tgc         6849
Glu Ala Trp Val Pro Asp His Gln Pro Cys Gln Ile Cys Thr Cys
2270              2275              2280 ctc agc ggg cgg aag gtc aac tgc aca acg cag ccc tgc ccc acg         6894
Leu Ser Gly Arg Lys Val Asn Cys Thr Thr Gln Pro Cys Pro Thr
2285              2290              2295 gcc aaa gct ccc acg tgt ggc ctg tgt gaa gta gcc cgc ctc cgc         6939
Ala Lys Ala Pro Thr Cys Gly Leu Cys Glu Val Ala Arg Leu Arg
2300              2305              2310 cag aat gca gac cag tgc tgc ccc gag tat gag tgt gtg tgt gac         6984
Gln Asn Ala Asp Gln Cys Cys Pro Glu Tyr Glu Cys Val Cys Asp
2315              2320              2325 cca gtg agc tgt gac ctg ccc cca gtg cct cac tgt gaa cgt ggc         7029
Pro Val Ser Cys Asp Leu Pro Pro Val Pro His Cys Glu Arg Gly
2330              2335              2340 ctc cag ccc aca ctg acc aac cct ggc gag tgc aga ccc aac ttc         7074
Leu Gln Pro Thr Leu Thr Asn Pro Gly Glu Cys Arg Pro Asn Phe
2345              2350              2355 acc tgc gcc tgc agg aag gag gag tgc aaa aga gtg tcc cca ccc         7119
```

```
Thr Cys Ala Cys Arg Lys Glu Glu Cys Lys Arg Val Ser Pro Pro
    2360            2365            2370 tcc tgc ccc ccg cac cgt ttg ccc acc ctt cgg aag acc cag tgc      7164
Ser Cys Pro Pro His Arg Leu Pro Thr Leu Arg Lys Thr Gln Cys
    2375            2380            2385 tgt gat gag tat gag tgt gcc tgc aac tgt gtc aac tcc aca gtg      7209
Cys Asp Glu Tyr Glu Cys Ala Cys Asn Cys Val Asn Ser Thr Val
    2390            2395            2400 agc tgt ccc ctt ggg tac ttg gcc tca acc gcc acc aat gac tgt      7254
Ser Cys Pro Leu Gly Tyr Leu Ala Ser Thr Ala Thr Asn Asp Cys
    2405            2410            2415 ggc tgt acc aca acc acc tgc ctt ccc gac aag gtg tgt gtc cac      7299
Gly Cys Thr Thr Thr Thr Cys Leu Pro Asp Lys Val Cys Val His
    2420            2425            2430 cga agc acc atc tac cct gtg ggc cag ttc tgg gag gag ggc tgc      7344
Arg Ser Thr Ile Tyr Pro Val Gly Gln Phe Trp Glu Glu Gly Cys
    2435            2440            2445 gat gtg tgc acc tgc acc gac atg gag gat gcc gtg atg ggc ctc      7389
Asp Val Cys Thr Cys Thr Asp Met Glu Asp Ala Val Met Gly Leu
    2450            2455            2460 cgc gtg gcc cag tgc tcc cag aag ccc tgt gag gac agc tgt cgg      7434
Arg Val Ala Gln Cys Ser Gln Lys Pro Cys Glu Asp Ser Cys Arg
    2465            2470            2475 tcg ggc ttc act tac gtt ctg cat gaa ggc gag tgc tgt gga agg      7479
Ser Gly Phe Thr Tyr Val Leu His Glu Gly Glu Cys Cys Gly Arg
    2480            2485            2490 tgc ctg cca tct gcc tgt gag gtg gtg act ggc tca ccg cgg ggg      7524
Cys Leu Pro Ser Ala Cys Glu Val Val Thr Gly Ser Pro Arg Gly
    2495            2500            2505 gac tcc cag tct tcc tgg aag agt gtc ggc tcc cag tgg gcc tcc      7569
Asp Ser Gln Ser Ser Trp Lys Ser Val Gly Ser Gln Trp Ala Ser
    2510            2515            2520 ccg gag aac ccc tgc ctc atc aat gag tgt gtc cga gtg aag gag      7614
Pro Glu Asn Pro Cys Leu Ile Asn Glu Cys Val Arg Val Lys Glu
    2525            2530            2535 gag gtc ttt ata caa caa agg aac gtc tcc tgc ccc cag ctg gag      7659
Glu Val Phe Ile Gln Gln Arg Asn Val Ser Cys Pro Gln Leu Glu
    2540            2545            2550 gtc cct gtc tgc ccc tcg ggc ttt cag ctg agc tgt aag acc tca      7704
Val Pro Val Cys Pro Ser Gly Phe Gln Leu Ser Cys Lys Thr Ser
    2555            2560            2565 gcg tgc tgc cca agc tgt cgc tgt gag cgc atg gag gcc tgc atg      7749
Ala Cys Cys Pro Ser Cys Arg Cys Glu Arg Met Glu Ala Cys Met
    2570            2575            2580 ctc aat ggc act gtc att ggg ccc ggg aag act gtg atg atc gat      7794
Leu Asn Gly Thr Val Ile Gly Pro Gly Lys Thr Val Met Ile Asp
    2585            2590            2595 gtg tgc acg acc tgc cgc tgc atg gtg cag gtg ggg gtc atc tct      7839
Val Cys Thr Thr Cys Arg Cys Met Val Gln Val Gly Val Ile Ser
    2600            2605            2610 gga ttc aag ctg gag tgc agg aag acc acc tgc aac ccc tgc ccc      7884
Gly Phe Lys Leu Glu Cys Arg Lys Thr Thr Cys Asn Pro Cys Pro
    2615            2620            2625 ctg ggt tac aag gaa gaa aat aac aca ggt gaa tgt tgt ggg aga      7929
Leu Gly Tyr Lys Glu Glu Asn Asn Thr Gly Glu Cys Cys Gly Arg
    2630            2635            2640 tgt ttg cct acg gct tgc acc att cag cta aga gga gga cag atc      7974
Cys Leu Pro Thr Ala Cys Thr Ile Gln Leu Arg Gly Gly Gln Ile
    2645            2650            2655
```

| | | | | | | | | | | | |
|---|---|---|---|---|---|---|---|---|---|---|---|
| atg | aca | ctg | aag | cgt | gat | gag | acg | ctc | cag | gat | ggc | tgt | gat | act | 8019 |
| Met | Thr | Leu | Lys | Arg | Asp | Glu | Thr | Leu | Gln | Asp | Gly | Cys | Asp | Thr | |
| 2660 | | | | 2665 | | | | | 2670 | | | | | | |

```
atg aca ctg aag cgt gat gag acg ctc cag gat ggc tgt gat act        8019
Met Thr Leu Lys Arg Asp Glu Thr Leu Gln Asp Gly Cys Asp Thr
2660            2665                2670 cac ttc tgc aag gtc aat gag aga gga gag tac ttc tgg gag aag        8064
His Phe Cys Lys Val Asn Glu Arg Gly Glu Tyr Phe Trp Glu Lys
    2675            2680                2685 agg gtc aca ggc tgc cca ccc ttt gat gaa cac aag tgt ctg gct        8109
Arg Val Thr Gly Cys Pro Pro Phe Asp Glu His Lys Cys Leu Ala
2690            2695                2700 gag gga ggt aaa att atg aaa att cca ggc acc tgc tgt gac aca        8154
Glu Gly Gly Lys Ile Met Lys Ile Pro Gly Thr Cys Cys Asp Thr
2705            2710                2715 tgt gag gag cct gag tgc aac gac atc act gcc agg ctg cag tat        8199
Cys Glu Glu Pro Glu Cys Asn Asp Ile Thr Ala Arg Leu Gln Tyr
2720            2725                2730 gtc aag gtg gga agc tgt aag tct gaa gta gag gtg gat atc cac        8244
Val Lys Val Gly Ser Cys Lys Ser Glu Val Glu Val Asp Ile His
2735            2740                2745 tac tgc cag ggc aaa tgt gcc agc aaa gcc atg tac tcc att gac        8289
Tyr Cys Gln Gly Lys Cys Ala Ser Lys Ala Met Tyr Ser Ile Asp
2750            2755                2760 atc aac gat gtg cag gac cag tgc tcc tgc tgc tct ccg aca cgg        8334
Ile Asn Asp Val Gln Asp Gln Cys Ser Cys Cys Ser Pro Thr Arg
2765            2770                2775 acg gag ccc atg cag gtg gcc ctg cac tgc acc aat ggc tct gtt        8379
Thr Glu Pro Met Gln Val Ala Leu His Cys Thr Asn Gly Ser Val
2780            2785                2790 gtg tac cat gag gtt ctc aat gcc atg gag tgc aaa tgc tcc ccc        8424
Val Tyr His Glu Val Leu Asn Ala Met Glu Cys Lys Cys Ser Pro
2795            2800                2805 agg aag tgc agc aag tga                                            8442
Arg Lys Cys Ser Lys
2810
```

<210> SEQ ID NO 9
<211> LENGTH: 2813
<212> TYPE: PRT
<213> ORGANISM: Homo sapiens

<400> SEQUENCE: 9

```
Met Ile Pro Ala Arg Phe Ala Gly Val Leu Leu Ala Leu Ala Leu Ile
1               5                   10                  15

Leu Pro Gly Thr Leu Cys Ala Glu Gly Thr Arg Gly Arg Ser Ser Thr
            20                  25                  30

Ala Arg Cys Ser Leu Phe Gly Ser Asp Phe Val Asn Thr Phe Asp Gly
        35                  40                  45

Ser Met Tyr Ser Phe Ala Gly Tyr Cys Ser Tyr Leu Leu Ala Gly Gly
    50                  55                  60

Cys Gln Lys Arg Ser Phe Ser Ile Ile Gly Asp Phe Gln Asn Gly Lys
65                  70                  75                  80

Arg Val Ser Leu Ser Val Tyr Leu Gly Glu Phe Phe Asp Ile His Leu
                85                  90                  95

Phe Val Asn Gly Thr Val Thr Gln Gly Asp Gln Arg Val Ser Met Pro
            100                 105                 110

Tyr Ala Ser Lys Gly Leu Tyr Leu Glu Thr Glu Ala Gly Tyr Tyr Lys
        115                 120                 125

Leu Ser Gly Glu Ala Tyr Gly Phe Val Ala Arg Ile Asp Gly Ser Gly
    130                 135                 140
```

```
Asn Phe Gln Val Leu Leu Ser Asp Arg Tyr Phe Asn Lys Thr Cys Gly
145                 150                 155                 160

Leu Cys Gly Asn Phe Asn Ile Phe Ala Glu Asp Asp Phe Met Thr Gln
            165                 170                 175

Glu Gly Thr Leu Thr Ser Asp Pro Tyr Asp Phe Ala Asn Ser Trp Ala
            180                 185                 190

Leu Ser Ser Gly Glu Gln Trp Cys Glu Arg Ala Ser Pro Ser Ser
            195                 200                 205

Ser Cys Asn Ile Ser Ser Gly Glu Met Gln Lys Gly Leu Trp Glu Gln
            210                 215                 220

Cys Gln Leu Leu Lys Ser Thr Ser Val Phe Ala Arg Cys His Pro Leu
225                 230                 235                 240

Val Asp Pro Glu Pro Phe Val Ala Leu Cys Glu Lys Thr Leu Cys Glu
                245                 250                 255

Cys Ala Gly Gly Leu Glu Cys Ala Cys Pro Ala Leu Leu Glu Tyr Ala
            260                 265                 270

Arg Thr Cys Ala Gln Glu Gly Met Val Leu Tyr Gly Trp Thr Asp His
            275                 280                 285

Ser Ala Cys Ser Pro Val Cys Pro Ala Gly Met Glu Tyr Arg Gln Cys
290                 295                 300

Val Ser Pro Cys Ala Arg Thr Cys Gln Ser Leu His Ile Asn Glu Met
305                 310                 315                 320

Cys Gln Glu Arg Cys Val Asp Gly Cys Ser Cys Pro Glu Gly Gln Leu
            325                 330                 335

Leu Asp Glu Gly Leu Cys Val Glu Ser Thr Glu Cys Pro Cys Val His
            340                 345                 350

Ser Gly Lys Arg Tyr Pro Pro Gly Thr Ser Leu Ser Arg Asp Cys Asn
            355                 360                 365

Thr Cys Ile Cys Arg Asn Ser Gln Trp Ile Cys Ser Asn Glu Glu Cys
370                 375                 380

Pro Gly Glu Cys Leu Val Thr Gly Gln Ser His Phe Lys Ser Phe Asp
385                 390                 395                 400

Asn Arg Tyr Phe Thr Phe Ser Gly Ile Cys Gln Tyr Leu Leu Ala Arg
            405                 410                 415

Asp Cys Gln Asp His Ser Phe Ser Ile Val Ile Glu Thr Val Gln Cys
            420                 425                 430

Ala Asp Asp Arg Asp Ala Val Cys Thr Arg Ser Val Thr Val Arg Leu
            435                 440                 445

Pro Gly Leu His Asn Ser Leu Val Lys Leu Lys His Gly Ala Gly Val
450                 455                 460

Ala Met Asp Gly Gln Asp Val Gln Leu Pro Leu Leu Lys Gly Asp Leu
465                 470                 475                 480

Arg Ile Gln His Thr Val Thr Ala Ser Val Arg Leu Ser Tyr Gly Glu
            485                 490                 495

Asp Leu Gln Met Asp Trp Asp Gly Arg Gly Arg Leu Leu Val Lys Leu
            500                 505                 510

Ser Pro Val Tyr Ala Gly Lys Thr Cys Gly Leu Cys Gly Asn Tyr Asn
            515                 520                 525

Gly Asn Gln Gly Asp Asp Phe Leu Thr Pro Ser Gly Leu Ala Glu Pro
            530                 535                 540

Arg Val Glu Asp Phe Gly Asn Ala Trp Lys Leu His Gly Asp Cys Gln
545                 550                 555                 560

Asp Leu Gln Lys Gln His Ser Asp Pro Cys Ala Leu Asn Pro Arg Met
```

-continued

```
                565                 570                 575
Thr Arg Phe Ser Glu Glu Ala Cys Ala Val Leu Thr Ser Pro Thr Phe
                580                 585                 590
Glu Ala Cys His Arg Ala Val Ser Pro Leu Pro Tyr Leu Arg Asn Cys
                595                 600                 605
Arg Tyr Asp Val Cys Ser Cys Ser Asp Gly Arg Glu Cys Leu Cys Gly
                610                 615                 620
Ala Leu Ala Ser Tyr Ala Ala Ala Cys Ala Gly Arg Gly Val Arg Val
625                 630                 635                 640
Ala Trp Arg Glu Pro Gly Arg Cys Glu Leu Asn Cys Pro Lys Gly Gln
                645                 650                 655
Val Tyr Leu Gln Cys Gly Thr Pro Cys Asn Leu Thr Cys Arg Ser Leu
                660                 665                 670
Ser Tyr Pro Asp Glu Glu Cys Asn Glu Ala Cys Leu Glu Gly Cys Phe
                675                 680                 685
Cys Pro Pro Gly Leu Tyr Met Asp Glu Arg Gly Asp Cys Val Pro Lys
                690                 695                 700
Ala Gln Cys Pro Cys Tyr Tyr Asp Gly Glu Ile Phe Gln Pro Glu Asp
705                 710                 715                 720
Ile Phe Ser Asp His His Thr Met Cys Tyr Cys Glu Asp Gly Phe Met
                725                 730                 735
His Cys Thr Met Ser Gly Val Pro Gly Ser Leu Leu Pro Asp Ala Val
                740                 745                 750
Leu Ser Ser Pro Leu Ser His Arg Ser Lys Arg Ser Leu Ser Cys Arg
                755                 760                 765
Pro Pro Met Val Lys Leu Val Cys Pro Ala Asp Asn Leu Arg Ala Glu
                770                 775                 780
Gly Leu Glu Cys Thr Lys Thr Cys Gln Asn Tyr Asp Leu Glu Cys Met
785                 790                 795                 800
Ser Met Gly Cys Val Ser Gly Cys Leu Cys Pro Pro Gly Met Val Arg
                805                 810                 815
His Glu Asn Arg Cys Val Ala Leu Glu Arg Cys Pro Cys Phe His Gln
                820                 825                 830
Gly Lys Glu Tyr Ala Pro Gly Glu Thr Val Lys Ile Gly Cys Asn Thr
                835                 840                 845
Cys Val Cys Arg Asp Arg Lys Trp Asn Cys Thr Asp His Val Cys Asp
                850                 855                 860
Ala Thr Cys Ser Thr Ile Gly Met Ala His Tyr Leu Thr Phe Asp Gly
865                 870                 875                 880
Leu Lys Tyr Leu Phe Pro Gly Glu Cys Gln Tyr Val Leu Val Gln Asp
                885                 890                 895
Tyr Cys Gly Ser Asn Pro Gly Thr Phe Arg Ile Leu Val Gly Asn Lys
                900                 905                 910
Gly Cys Ser His Pro Ser Val Lys Cys Lys Arg Val Thr Ile Leu
                915                 920                 925
Val Glu Gly Gly Glu Ile Glu Leu Phe Asp Gly Glu Val Asn Val Lys
                930                 935                 940
Arg Pro Met Lys Asp Glu Thr His Phe Glu Val Val Glu Ser Gly Arg
945                 950                 955                 960
Tyr Ile Ile Leu Leu Leu Gly Lys Ala Leu Ser Val Val Trp Asp Arg
                965                 970                 975
His Leu Ser Ile Ser Val Val Leu Lys Gln Thr Tyr Gln Glu Lys Val
                980                 985                 990
```

```
Cys Gly Leu Cys Gly Asn Phe Asp  Gly Ile Gln Asn  Asn  Asp Leu Thr
        995              1000             1005

Ser Ser  Asn Leu Gln Val Glu  Glu Asp Pro Val Asp  Phe Gly Asn
    1010             1015              1020

Ser Trp  Lys Val Ser Ser Gln  Cys Ala Asp Thr Arg  Lys Val Pro
    1025             1030              1035

Leu Asp  Ser Ser Pro Ala Thr  Cys His Asn Asn Ile  Met Lys Gln
    1040             1045              1050

Thr Met  Val Asp Ser Ser Cys  Arg Ile Leu Thr Ser  Asp Val Phe
    1055             1060              1065

Gln Asp  Cys Asn Lys Leu Val  Asp Pro Glu Pro Tyr  Leu Asp Val
    1070             1075              1080

Cys Ile  Tyr Asp Thr Cys Ser  Cys Glu Ser Ile Gly  Asp Cys Ala
    1085             1090              1095

Cys Phe  Cys Asp Thr Ile Ala  Ala Tyr Ala His Val  Cys Ala Gln
    1100             1105              1110

His Gly  Lys Val Val Thr Trp  Arg Thr Ala Thr Leu  Cys Pro Gln
    1115             1120              1125

Ser Cys  Glu Glu Arg Asn Leu  Arg Glu Asn Gly Tyr  Glu Cys Glu
    1130             1135              1140

Trp Arg  Tyr Asn Ser Cys Ala  Pro Ala Cys Gln Val  Thr Cys Gln
    1145             1150              1155

His Pro  Glu Pro Leu Ala Cys  Pro Val Gln Cys Val  Glu Gly Cys
    1160             1165              1170

His Ala  His Cys Pro Pro Gly  Lys Ile Leu Asp Glu  Leu Leu Gln
    1175             1180              1185

Thr Cys  Val Asp Pro Glu Asp  Cys Pro Val Cys Glu  Val Ala Gly
    1190             1195              1200

Arg Arg  Phe Ala Ser Gly Lys  Lys Val Thr Leu Asn  Pro Ser Asp
    1205             1210              1215

Pro Glu  His Cys Gln Ile Cys  His Cys Asp Val Val  Asn Leu Thr
    1220             1225              1230

Cys Glu  Ala Cys Gln Glu Pro  Gly Gly Leu Val Val  Pro Pro Thr
    1235             1240              1245

Asp Ala  Pro Val Ser Pro Thr  Thr Leu Tyr Val Glu  Asp Ile Ser
    1250             1255              1260

Glu Pro  Pro Leu His Asp Phe  Tyr Cys Ser Arg Leu  Leu Asp Leu
    1265             1270              1275

Val Phe  Leu Leu Asp Gly Ser  Ser Arg Leu Ser Glu  Ala Glu Phe
    1280             1285              1290

Glu Val  Leu Lys Ala Phe Val  Val Asp Met Met Glu  Arg Leu Arg
    1295             1300              1305

Ile Ser  Gln Lys Trp Val Arg  Val Ala Val Val Glu  Tyr His Asp
    1310             1315              1320

Gly Ser  His Ala Tyr Ile Gly  Leu Lys Asp Arg Lys  Arg Pro Ser
    1325             1330              1335

Glu Leu  Arg Arg Ile Ala Ser  Gln Val Lys Tyr Ala  Gly Ser Gln
    1340             1345              1350

Val Ala  Ser Thr Ser Glu Val  Leu Lys Tyr Thr Leu  Phe Gln Ile
    1355             1360              1365

Phe Ser  Lys Ile Asp Arg Pro  Glu Ala Ser Arg Ile  Ala Leu Leu
    1370             1375              1380
```

-continued

```
Leu Met Ala Ser Gln Glu Pro Gln Arg Met Ser Arg Asn Phe Val
1385                1390                1395

Arg Tyr Val Gln Gly Leu Lys Lys Lys Val Ile Val Ile Pro
1400                1405                1410

Val Gly Ile Gly Pro His Ala Asn Leu Lys Gln Ile Arg Leu Ile
1415                1420                1425

Glu Lys Gln Ala Pro Glu Asn Lys Ala Phe Val Leu Ser Ser Val
1430                1435                1440

Asp Glu Leu Glu Gln Gln Arg Asp Glu Ile Val Ser Tyr Leu Cys
1445                1450                1455

Asp Leu Ala Pro Glu Ala Pro Pro Pro Thr Leu Pro Pro His Met
1460                1465                1470

Ala Gln Val Thr Val Gly Pro Gly Leu Leu Gly Val Ser Thr Leu
1475                1480                1485

Gly Pro Lys Arg Asn Ser Met Val Leu Asp Val Ala Phe Val Leu
1490                1495                1500

Glu Gly Ser Asp Lys Ile Gly Glu Ala Asp Phe Asn Arg Ser Lys
1505                1510                1515

Glu Phe Met Glu Glu Val Ile Gln Arg Met Asp Val Gly Gln Asp
1520                1525                1530

Ser Ile His Val Thr Val Leu Gln Tyr Ser Tyr Met Val Thr Val
1535                1540                1545

Glu Tyr Pro Phe Ser Glu Ala Gln Ser Lys Gly Asp Ile Leu Gln
1550                1555                1560

Arg Val Arg Glu Ile Arg Tyr Gln Gly Gly Asn Arg Thr Asn Thr
1565                1570                1575

Gly Leu Ala Leu Arg Tyr Leu Ser Asp His Ser Phe Leu Val Ser
1580                1585                1590

Gln Gly Asp Arg Glu Gln Ala Pro Asn Leu Val Tyr Met Val Thr
1595                1600                1605

Gly Asn Pro Ala Ser Asp Glu Ile Lys Arg Leu Pro Gly Asp Ile
1610                1615                1620

Gln Val Val Pro Ile Gly Val Gly Pro Asn Ala Asn Val Gln Glu
1625                1630                1635

Leu Glu Arg Ile Gly Trp Pro Asn Ala Pro Ile Leu Ile Gln Asp
1640                1645                1650

Phe Glu Thr Leu Pro Arg Glu Ala Pro Asp Leu Val Leu Gln Arg
1655                1660                1665

Cys Cys Ser Gly Glu Gly Leu Gln Ile Pro Thr Leu Ser Pro Ala
1670                1675                1680

Pro Asp Cys Ser Gln Pro Leu Asp Val Ile Leu Leu Leu Asp Gly
1685                1690                1695

Ser Ser Ser Phe Pro Ala Ser Tyr Phe Asp Glu Met Lys Ser Phe
1700                1705                1710

Ala Lys Ala Phe Ile Ser Lys Ala Asn Ile Gly Pro Arg Leu Thr
1715                1720                1725

Gln Val Ser Val Leu Gln Tyr Gly Ser Ile Thr Thr Ile Asp Val
1730                1735                1740

Pro Trp Asn Val Val Pro Glu Lys Ala His Leu Leu Ser Leu Val
1745                1750                1755

Asp Val Met Gln Arg Glu Gly Gly Pro Ser Gln Ile Gly Asp Ala
1760                1765                1770

Leu Gly Phe Ala Val Arg Tyr Leu Thr Ser Glu Met His Gly Ala
```

```
        1775                1780                1785

Arg Pro Gly Ala Ser Lys Ala Val Val Ile Leu Val Thr Asp Val
        1790                1795                1800

Ser Val Asp Ser Val Asp Ala Ala Asp Ala Ala Arg Ser Asn
        1805                1810                1815

Arg Val Thr Val Phe Pro Ile Gly Ile Gly Asp Arg Tyr Asp Ala
        1820                1825                1830

Ala Gln Leu Arg Ile Leu Ala Gly Pro Ala Gly Asp Ser Asn Val
        1835                1840                1845

Val Lys Leu Gln Arg Ile Glu Asp Leu Pro Thr Met Val Thr Leu
        1850                1855                1860

Gly Asn Ser Phe Leu His Lys Leu Cys Ser Gly Phe Val Arg Ile
        1865                1870                1875

Cys Met Asp Glu Asp Gly Asn Glu Lys Arg Pro Gly Asp Val Trp
        1880                1885                1890

Thr Leu Pro Asp Gln Cys His Thr Val Thr Cys Gln Pro Asp Gly
        1895                1900                1905

Gln Thr Leu Leu Lys Ser His Arg Val Asn Cys Asp Arg Gly Leu
        1910                1915                1920

Arg Pro Ser Cys Pro Asn Ser Gln Ser Pro Val Lys Val Glu Glu
        1925                1930                1935

Thr Cys Gly Cys Arg Trp Thr Cys Pro Cys Val Cys Thr Gly Ser
        1940                1945                1950

Ser Thr Arg His Ile Val Thr Phe Asp Gly Gln Asn Phe Lys Leu
        1955                1960                1965

Thr Gly Ser Cys Ser Tyr Val Leu Phe Gln Asn Lys Glu Gln Asp
        1970                1975                1980

Leu Glu Val Ile Leu His Asn Gly Ala Cys Ser Pro Gly Ala Arg
        1985                1990                1995

Gln Gly Cys Met Lys Ser Ile Glu Val Lys His Ser Ala Leu Ser
        2000                2005                2010

Val Glu Leu His Ser Asp Met Glu Val Thr Val Asn Gly Arg Leu
        2015                2020                2025

Val Ser Val Pro Tyr Val Gly Gly Asn Met Glu Val Asn Val Tyr
        2030                2035                2040

Gly Ala Ile Met His Glu Val Arg Phe Asn His Leu Gly His Ile
        2045                2050                2055

Phe Thr Phe Thr Pro Gln Asn Asn Glu Phe Gln Leu Gln Leu Ser
        2060                2065                2070

Pro Lys Thr Phe Ala Ser Lys Thr Tyr Gly Leu Cys Gly Ile Cys
        2075                2080                2085

Asp Glu Asn Gly Ala Asn Asp Phe Met Leu Arg Asp Gly Thr Val
        2090                2095                2100

Thr Thr Asp Trp Lys Thr Leu Val Gln Glu Trp Thr Val Gln Arg
        2105                2110                2115

Pro Gly Gln Thr Cys Gln Pro Ile Leu Glu Glu Gln Cys Leu Val
        2120                2125                2130

Pro Asp Ser Ser His Cys Gln Val Leu Leu Leu Pro Leu Phe Ala
        2135                2140                2145

Glu Cys His Lys Val Leu Ala Pro Ala Thr Phe Tyr Ala Ile Cys
        2150                2155                2160

Gln Gln Asp Ser Cys His Gln Glu Gln Val Cys Glu Val Ile Ala
        2165                2170                2175
```

```
Ser Tyr Ala His Leu Cys Arg Thr Asn Gly Val Cys Val Asp Trp
    2180            2185                2190

Arg Thr Pro Asp Phe Cys Ala Met Ser Cys Pro Pro Ser Leu Val
    2195            2200                2205

Tyr Asn His Cys Glu His Gly Cys Pro Arg His Cys Asp Gly Asn
    2210            2215                2220

Val Ser Ser Cys Gly Asp His Pro Ser Glu Gly Cys Phe Cys Pro
    2225            2230                2235

Pro Asp Lys Val Met Leu Glu Gly Ser Cys Val Pro Glu Glu Ala
    2240            2245                2250

Cys Thr Gln Cys Ile Gly Glu Asp Gly Val Gln His Gln Phe Leu
    2255            2260                2265

Glu Ala Trp Val Pro Asp His Gln Pro Cys Gln Ile Cys Thr Cys
    2270            2275                2280

Leu Ser Gly Arg Lys Val Asn Cys Thr Thr Gln Pro Cys Pro Thr
    2285            2290                2295

Ala Lys Ala Pro Thr Cys Gly Leu Cys Glu Val Ala Arg Leu Arg
    2300            2305                2310

Gln Asn Ala Asp Gln Cys Cys Pro Glu Tyr Glu Cys Val Cys Asp
    2315            2320                2325

Pro Val Ser Cys Asp Leu Pro Pro Val Pro His Cys Glu Arg Gly
    2330            2335                2340

Leu Gln Pro Thr Leu Thr Asn Pro Gly Glu Cys Arg Pro Asn Phe
    2345            2350                2355

Thr Cys Ala Cys Arg Lys Glu Glu Cys Lys Arg Val Ser Pro Pro
    2360            2365                2370

Ser Cys Pro Pro His Arg Leu Pro Thr Leu Arg Lys Thr Gln Cys
    2375            2380                2385

Cys Asp Glu Tyr Glu Cys Ala Cys Asn Cys Val Asn Ser Thr Val
    2390            2395                2400

Ser Cys Pro Leu Gly Tyr Leu Ala Ser Thr Ala Thr Asn Asp Cys
    2405            2410                2415

Gly Cys Thr Thr Thr Thr Cys Leu Pro Asp Lys Val Cys Val His
    2420            2425                2430

Arg Ser Thr Ile Tyr Pro Val Gly Gln Phe Trp Glu Glu Gly Cys
    2435            2440                2445

Asp Val Cys Thr Cys Thr Asp Met Glu Asp Ala Val Met Gly Leu
    2450            2455                2460

Arg Val Ala Gln Cys Ser Gln Lys Pro Cys Glu Asp Ser Cys Arg
    2465            2470                2475

Ser Gly Phe Thr Tyr Val Leu His Glu Gly Glu Cys Cys Gly Arg
    2480            2485                2490

Cys Leu Pro Ser Ala Cys Glu Val Val Thr Gly Ser Pro Arg Gly
    2495            2500                2505

Asp Ser Gln Ser Ser Trp Lys Ser Val Gly Ser Gln Trp Ala Ser
    2510            2515                2520

Pro Glu Asn Pro Cys Leu Ile Asn Glu Cys Val Arg Val Lys Glu
    2525            2530                2535

Glu Val Phe Ile Gln Gln Arg Asn Val Ser Cys Pro Gln Leu Glu
    2540            2545                2550

Val Pro Val Cys Pro Ser Gly Phe Gln Leu Ser Cys Lys Thr Ser
    2555            2560                2565
```

```
Ala Cys Cys Pro Ser Cys Arg Cys Glu Arg Met Glu Ala Cys Met
2570                2575                2580

Leu Asn Gly Thr Val Ile Gly Pro Gly Lys Thr Val Met Ile Asp
    2585                2590                2595

Val Cys Thr Thr Cys Arg Cys Met Val Gln Val Gly Val Ile Ser
2600                2605                2610

Gly Phe Lys Leu Glu Cys Arg Lys Thr Thr Cys Asn Pro Cys Pro
    2615                2620                2625

Leu Gly Tyr Lys Glu Glu Asn Asn Thr Gly Glu Cys Cys Gly Arg
    2630                2635                2640

Cys Leu Pro Thr Ala Cys Thr Ile Gln Leu Arg Gly Gly Gln Ile
2645                2650                2655

Met Thr Leu Lys Arg Asp Glu Thr Leu Gln Asp Gly Cys Asp Thr
2660                2665                2670

His Phe Cys Lys Val Asn Glu Arg Gly Glu Tyr Phe Trp Glu Lys
    2675                2680                2685

Arg Val Thr Gly Cys Pro Pro Phe Asp Glu His Lys Cys Leu Ala
    2690                2695                2700

Glu Gly Gly Lys Ile Met Lys Ile Pro Gly Thr Cys Cys Asp Thr
    2705                2710                2715

Cys Glu Glu Pro Glu Cys Asn Asp Ile Thr Ala Arg Leu Gln Tyr
2720                2725                2730

Val Lys Val Gly Ser Cys Lys Ser Glu Val Glu Val Asp Ile His
    2735                2740                2745

Tyr Cys Gln Gly Lys Cys Ala Ser Lys Ala Met Tyr Ser Ile Asp
    2750                2755                2760

Ile Asn Asp Val Gln Asp Gln Cys Ser Cys Cys Ser Pro Thr Arg
    2765                2770                2775

Thr Glu Pro Met Gln Val Ala Leu His Cys Thr Asn Gly Ser Val
    2780                2785                2790

Val Tyr His Glu Val Leu Asn Ala Met Glu Cys Lys Cys Ser Pro
    2795                2800                2805

Arg Lys Cys Ser Lys
    2810

<210> SEQ ID NO 10
<211> LENGTH: 1444
<212> TYPE: PRT
<213> ORGANISM: Artificial Sequence
<220> FEATURE:
<223> OTHER INFORMATION: amino acid sequence of a single chain factor
      viii molecule

<400> SEQUENCE: 10

Ala Thr Arg Arg Tyr Tyr Leu Gly Ala Val Glu Leu Ser Trp Asp Tyr
1               5                   10                  15

Met Gln Ser Asp Leu Gly Glu Leu Pro Val Asp Ala Arg Phe Pro Pro
            20                  25                  30

Arg Val Pro Lys Ser Phe Pro Phe Asn Thr Ser Val Val Tyr Lys Lys
        35                  40                  45

Thr Leu Phe Val Glu Phe Thr Asp His Leu Phe Asn Ile Ala Lys Pro
    50                  55                  60

Arg Pro Pro Trp Met Gly Leu Leu Gly Pro Thr Ile Gln Ala Glu Val
65                  70                  75                  80

Tyr Asp Thr Val Val Ile Thr Leu Lys Asn Met Ala Ser His Pro Val
                85                  90                  95
```

```
Ser Leu His Ala Val Gly Val Ser Tyr Trp Lys Ala Ser Glu Gly Ala
            100                 105                 110

Glu Tyr Asp Asp Gln Thr Ser Gln Arg Glu Lys Glu Asp Asp Lys Val
            115                 120                 125

Phe Pro Gly Gly Ser His Thr Tyr Val Trp Gln Val Leu Lys Glu Asn
130                 135                 140

Gly Pro Met Ala Ser Asp Pro Leu Cys Leu Thr Tyr Ser Tyr Leu Ser
145                 150                 155                 160

His Val Asp Leu Val Lys Asp Leu Asn Ser Gly Leu Ile Gly Ala Leu
            165                 170                 175

Leu Val Cys Arg Glu Gly Ser Leu Ala Lys Lys Thr Gln Thr Leu
            180                 185                 190

His Lys Phe Ile Leu Leu Phe Ala Val Phe Asp Glu Gly Lys Ser Trp
            195                 200                 205

His Ser Glu Thr Lys Asn Ser Leu Met Gln Asp Arg Asp Ala Ala Ser
            210                 215                 220

Ala Arg Ala Trp Pro Lys Met His Thr Val Asn Gly Tyr Val Asn Arg
225                 230                 235                 240

Ser Leu Pro Gly Leu Ile Gly Cys His Arg Lys Ser Val Tyr Trp His
            245                 250                 255

Val Ile Gly Met Gly Thr Thr Pro Glu Val His Ser Ile Phe Leu Glu
            260                 265                 270

Gly His Thr Phe Leu Val Arg Asn His Arg Gln Ala Ser Leu Glu Ile
            275                 280                 285

Ser Pro Ile Thr Phe Leu Thr Ala Gln Thr Leu Leu Met Asp Leu Gly
            290                 295                 300

Gln Phe Leu Leu Phe Cys His Ile Ser Ser His Gln His Asp Gly Met
305                 310                 315                 320

Glu Ala Tyr Val Lys Val Asp Ser Cys Pro Glu Glu Pro Gln Leu Arg
            325                 330                 335

Met Lys Asn Asn Glu Glu Ala Glu Asp Tyr Asp Asp Leu Thr Asp
            340                 345                 350

Ser Glu Met Asp Val Val Arg Phe Asp Asp Asn Ser Pro Ser Phe
            355                 360                 365

Ile Gln Ile Arg Ser Val Ala Lys Lys His Pro Lys Thr Trp Val His
370                 375                 380

Tyr Ile Ala Ala Glu Glu Asp Trp Asp Tyr Ala Pro Leu Val Leu
385                 390                 395                 400

Ala Pro Asp Asp Arg Ser Tyr Lys Ser Gln Tyr Leu Asn Asn Gly Pro
            405                 410                 415

Gln Arg Ile Gly Arg Lys Tyr Lys Lys Val Arg Phe Met Ala Tyr Thr
            420                 425                 430

Asp Glu Thr Phe Lys Thr Arg Glu Ala Ile Gln His Glu Ser Gly Ile
            435                 440                 445

Leu Gly Pro Leu Leu Tyr Gly Glu Val Gly Asp Thr Leu Leu Ile Ile
            450                 455                 460

Phe Lys Asn Gln Ala Ser Arg Pro Tyr Asn Ile Tyr Pro His Gly Ile
465                 470                 475                 480

Thr Asp Val Arg Pro Leu Tyr Ser Arg Arg Leu Pro Lys Gly Val Lys
            485                 490                 495

His Leu Lys Asp Phe Pro Ile Leu Pro Gly Glu Ile Phe Lys Tyr Lys
            500                 505                 510
```

```
Trp Thr Val Thr Val Glu Asp Gly Pro Thr Lys Ser Asp Pro Arg Cys
        515                 520                 525

Leu Thr Arg Tyr Tyr Ser Ser Phe Val Asn Met Glu Arg Asp Leu Ala
        530                 535                 540

Ser Gly Leu Ile Gly Pro Leu Ile Cys Tyr Lys Glu Ser Val Asp
545                 550                 555                 560

Gln Arg Gly Asn Gln Ile Met Ser Asp Lys Arg Asn Val Ile Leu Phe
                565                 570                 575

Ser Val Phe Asp Glu Asn Arg Ser Trp Tyr Leu Thr Glu Asn Ile Gln
            580                 585                 590

Arg Phe Leu Pro Asn Pro Ala Gly Val Gln Leu Glu Asp Pro Glu Phe
        595                 600                 605

Gln Ala Ser Asn Ile Met His Ser Ile Asn Gly Tyr Val Phe Asp Ser
        610                 615                 620

Leu Gln Leu Ser Val Cys Leu His Glu Val Ala Tyr Trp Tyr Ile Leu
625                 630                 635                 640

Ser Ile Gly Ala Gln Thr Asp Phe Leu Ser Val Phe Phe Ser Gly Tyr
                645                 650                 655

Thr Phe Lys His Lys Met Val Tyr Glu Asp Thr Leu Thr Leu Phe Pro
            660                 665                 670

Phe Ser Gly Glu Thr Val Phe Met Ser Met Glu Asn Pro Gly Leu Trp
        675                 680                 685

Ile Leu Gly Cys His Asn Ser Asp Phe Arg Asn Arg Gly Met Thr Ala
        690                 695                 700

Leu Leu Lys Val Ser Ser Cys Asp Lys Asn Thr Gly Asp Tyr Tyr Glu
705                 710                 715                 720

Asp Ser Tyr Glu Asp Ile Ser Ala Tyr Leu Leu Ser Lys Asn Asn Ala
                725                 730                 735

Ile Glu Pro Arg Ser Phe Ser Gln Asn Ser Arg His Pro Ser Thr Arg
            740                 745                 750

Gln Lys Gln Phe Asn Ala Thr Thr Ile Pro Glu Asn Thr Thr Leu Gln
        755                 760                 765

Ser Asp Gln Glu Glu Ile Asp Tyr Asp Asp Thr Ile Ser Val Glu Met
770                 775                 780

Lys Lys Glu Asp Phe Asp Ile Tyr Asp Glu Asp Glu Asn Gln Ser Pro
785                 790                 795                 800

Arg Ser Phe Gln Lys Lys Thr Arg His Tyr Phe Ile Ala Ala Val Glu
                805                 810                 815

Arg Leu Trp Asp Tyr Gly Met Ser Ser Ser Pro His Val Leu Arg Asn
            820                 825                 830

Arg Ala Gln Ser Gly Ser Val Pro Gln Phe Lys Lys Val Val Phe Gln
        835                 840                 845

Glu Phe Thr Asp Gly Ser Phe Thr Gln Pro Leu Tyr Arg Gly Glu Leu
850                 855                 860

Asn Glu His Leu Gly Leu Leu Gly Pro Tyr Ile Arg Ala Glu Val Glu
865                 870                 875                 880

Asp Asn Ile Met Val Thr Phe Arg Asn Gln Ala Ser Arg Pro Tyr Ser
                885                 890                 895

Phe Tyr Ser Ser Leu Ile Ser Tyr Glu Glu Asp Gln Arg Gln Gly Ala
            900                 905                 910

Glu Pro Arg Lys Asn Phe Val Lys Pro Asn Glu Thr Lys Thr Tyr Phe
        915                 920                 925

Trp Lys Val Gln His His Met Ala Pro Thr Lys Asp Glu Phe Asp Cys
```

```
                930            935            940
Lys Ala Trp Ala Tyr Phe Ser Asp Val Asp Leu Glu Lys Asp Val His
945            950            955            960

Ser Gly Leu Ile Gly Pro Leu Leu Val Cys His Thr Asn Thr Leu Asn
            965            970            975

Pro Ala His Gly Arg Gln Val Thr Val Gln Glu Phe Ala Leu Phe Phe
            980            985            990

Thr Ile Phe Asp Glu Thr Lys Ser Trp Tyr Phe Thr Glu Asn Met Glu
            995            1000           1005

Arg Asn Cys Arg Ala Pro Cys Asn Ile Gln Met Glu Asp Pro Thr
    1010           1015           1020

Phe Lys Glu Asn Tyr Arg Phe His Ala Ile Asn Gly Tyr Ile Met
    1025           1030           1035

Asp Thr Leu Pro Gly Leu Val Met Ala Gln Asp Gln Arg Ile Arg
    1040           1045           1050

Trp Tyr Leu Leu Ser Met Gly Ser Asn Glu Asn Ile His Ser Ile
    1055           1060           1065

His Phe Ser Gly His Val Phe Thr Val Arg Lys Lys Glu Glu Tyr
    1070           1075           1080

Lys Met Ala Leu Tyr Asn Leu Tyr Pro Gly Val Phe Glu Thr Val
    1085           1090           1095

Glu Met Leu Pro Ser Lys Ala Gly Ile Trp Arg Val Glu Cys Leu
    1100           1105           1110

Ile Gly Glu His Leu His Ala Gly Met Ser Thr Leu Phe Leu Val
    1115           1120           1125

Tyr Ser Asn Lys Cys Gln Thr Pro Leu Gly Met Ala Ser Gly His
    1130           1135           1140

Ile Arg Asp Phe Gln Ile Thr Ala Ser Gly Gln Tyr Gly Gln Trp
    1145           1150           1155

Ala Pro Lys Leu Ala Arg Leu His Tyr Ser Gly Ser Ile Asn Ala
    1160           1165           1170

Trp Ser Thr Lys Glu Pro Phe Ser Trp Ile Lys Val Asp Leu Leu
    1175           1180           1185

Ala Pro Met Ile Ile His Gly Ile Lys Thr Gln Gly Ala Arg Gln
    1190           1195           1200

Lys Phe Ser Ser Leu Tyr Ile Ser Gln Phe Ile Ile Met Tyr Ser
    1205           1210           1215

Leu Asp Gly Lys Lys Trp Gln Thr Tyr Arg Gly Asn Ser Thr Gly
    1220           1225           1230

Thr Leu Met Val Phe Phe Gly Asn Val Asp Ser Ser Gly Ile Lys
    1235           1240           1245

His Asn Ile Phe Asn Pro Pro Ile Ile Ala Arg Tyr Ile Arg Leu
    1250           1255           1260

His Pro Thr His Tyr Ser Ile Arg Ser Thr Leu Arg Met Glu Leu
    1265           1270           1275

Met Gly Cys Asp Leu Asn Ser Cys Ser Met Pro Leu Gly Met Glu
    1280           1285           1290

Ser Lys Ala Ile Ser Asp Ala Gln Ile Thr Ala Ser Ser Tyr Phe
    1295           1300           1305

Thr Asn Met Phe Ala Thr Trp Ser Pro Ser Lys Ala Arg Leu His
    1310           1315           1320

Leu Gln Gly Arg Ser Asn Ala Trp Arg Pro Gln Val Asn Asn Pro
    1325           1330           1335
```

Lys Glu Trp Leu Gln Val Asp Phe Gln Lys Thr Met Lys Val Thr
1340                1345                1350

Gly Val Thr Thr Gln Gly Val Lys Ser Leu Leu Thr Ser Met Tyr
    1355                1360                1365

Val Lys Glu Phe Leu Ile Ser Ser Ser Gln Asp Gly His Gln Trp
1370                1375                1380

Thr Leu Phe Phe Gln Asn Gly Lys Val Lys Val Phe Gln Gly Asn
    1385                1390                1395

Gln Asp Ser Phe Thr Pro Val Val Asn Ser Leu Asp Pro Pro Leu
1400                1405                1410

Leu Thr Arg Tyr Leu Arg Ile His Pro Gln Ser Trp Val His Gln
    1415                1420                1425

Ile Ala Leu Arg Met Glu Val Leu Gly Cys Glu Ala Gln Asp Leu
1430                1435                1440

Tyr

<210> SEQ ID NO 11
<211> LENGTH: 585
<212> TYPE: PRT
<213> ORGANISM: Homo sapiens

<400> SEQUENCE: 11

Asp Ala His Lys Ser Glu Val Ala His Arg Phe Lys Asp Leu Gly Glu
1               5                   10                  15

Glu Asn Phe Lys Ala Leu Val Leu Ile Ala Phe Ala Gln Tyr Leu Gln
            20                  25                  30

Gln Cys Pro Phe Glu Asp His Val Lys Leu Val Asn Glu Val Thr Glu
        35                  40                  45

Phe Ala Lys Thr Cys Val Ala Asp Glu Ser Ala Glu Asn Cys Asp Lys
    50                  55                  60

Ser Leu His Thr Leu Phe Gly Asp Lys Leu Cys Thr Val Ala Thr Leu
65                  70                  75                  80

Arg Glu Thr Tyr Gly Glu Met Ala Asp Cys Cys Ala Lys Gln Glu Pro
                85                  90                  95

Glu Arg Asn Glu Cys Phe Leu Gln His Lys Asp Asp Asn Pro Asn Leu
            100                 105                 110

Pro Arg Leu Val Arg Pro Glu Val Asp Val Met Cys Thr Ala Phe His
        115                 120                 125

Asp Asn Glu Glu Thr Phe Leu Lys Lys Tyr Leu Tyr Glu Ile Ala Arg
    130                 135                 140

Arg His Pro Tyr Phe Tyr Ala Pro Glu Leu Leu Phe Phe Ala Lys Arg
145                 150                 155                 160

Tyr Lys Ala Ala Phe Thr Glu Cys Cys Gln Ala Ala Asp Lys Ala Ala
                165                 170                 175

Cys Leu Leu Pro Lys Leu Asp Glu Leu Arg Asp Glu Gly Lys Ala Ser
            180                 185                 190

Ser Ala Lys Gln Arg Leu Lys Cys Ala Ser Leu Gln Lys Phe Gly Glu
        195                 200                 205

Arg Ala Phe Lys Ala Trp Ala Val Ala Arg Leu Ser Gln Arg Phe Pro
    210                 215                 220

Lys Ala Glu Phe Ala Glu Val Ser Lys Leu Val Thr Asp Leu Thr Lys
225                 230                 235                 240

Val His Thr Glu Cys Cys His Gly Asp Leu Leu Glu Cys Ala Asp Asp
                245                 250                 255

```
Arg Ala Asp Leu Ala Lys Tyr Ile Cys Glu Asn Gln Asp Ser Ile Ser
            260                 265                 270

Ser Lys Leu Lys Glu Cys Cys Glu Lys Pro Leu Leu Glu Lys Ser His
        275                 280                 285

Cys Ile Ala Glu Val Glu Asn Asp Glu Met Pro Ala Asp Leu Pro Ser
    290                 295                 300

Leu Ala Ala Asp Phe Val Glu Ser Lys Asp Val Cys Lys Asn Tyr Ala
305                 310                 315                 320

Glu Ala Lys Asp Val Phe Leu Gly Met Phe Leu Tyr Glu Tyr Ala Arg
                325                 330                 335

Arg His Pro Asp Tyr Ser Val Val Leu Leu Arg Leu Ala Lys Thr
            340                 345                 350

Tyr Glu Thr Thr Leu Glu Lys Cys Cys Ala Ala Ala Asp Pro His Glu
        355                 360                 365

Cys Tyr Ala Lys Val Phe Asp Glu Phe Lys Pro Leu Val Glu Glu Pro
    370                 375                 380

Gln Asn Leu Ile Lys Gln Asn Cys Glu Leu Phe Glu Gln Leu Gly Glu
385                 390                 395                 400

Tyr Lys Phe Gln Asn Ala Leu Leu Val Arg Tyr Thr Lys Lys Val Pro
                405                 410                 415

Gln Val Ser Thr Pro Thr Leu Val Glu Val Ser Arg Asn Leu Gly Lys
            420                 425                 430

Val Gly Ser Lys Cys Cys Lys His Pro Glu Ala Lys Arg Met Pro Cys
        435                 440                 445

Ala Glu Asp Tyr Leu Ser Val Val Leu Asn Gln Leu Cys Val Leu His
    450                 455                 460

Glu Lys Thr Pro Val Ser Asp Arg Val Thr Lys Cys Cys Thr Glu Ser
465                 470                 475                 480

Leu Val Asn Arg Arg Pro Cys Phe Ser Ala Leu Glu Val Asp Glu Thr
                485                 490                 495

Tyr Val Pro Lys Glu Phe Asn Ala Glu Thr Phe Thr Phe His Ala Asp
            500                 505                 510

Ile Cys Thr Leu Ser Glu Lys Glu Arg Gln Ile Lys Lys Gln Thr Ala
        515                 520                 525

Leu Val Glu Leu Val Lys His Lys Pro Lys Ala Thr Lys Glu Gln Leu
    530                 535                 540

Lys Ala Val Met Asp Asp Phe Ala Ala Phe Val Glu Lys Cys Cys Lys
545                 550                 555                 560

Ala Asp Asp Lys Glu Thr Cys Phe Ala Glu Glu Gly Lys Lys Leu Val
                565                 570                 575

Ala Ala Ser Gln Ala Ala Leu Gly Leu
            580                 585

<210> SEQ ID NO 12
<211> LENGTH: 1023
<212> TYPE: DNA
<213> ORGANISM: Homo sapiens

<400> SEQUENCE: 12
atggtgaccc tgcggaagag gaccctgaaa gtgctcacct tcctcgtgct cttcatcttc     60
ctcacctcct tcttcctgaa ctactcccac accatggtgg ccaccacctg gttccccaag    120
cagatggtcc tggagctctc cgagaacctg aagagactga tcaagcacag gccttgcacc    180 tgcaccccact gcatcgggca gcgcaagctc tcggcctggt tcgatgagag gttcaaccag    240
```

```
accatgcagc cgctgctgac cgcccagaac gcgctcttgg aggacgacac ctaccgatgg    300
tggctgaggc tccagcggga gaagaagccc aataacttga atgacaccat caaggagctg    360
ttcagagtgg tgcctgggaa tgtggaccct atgctggaga agaggtcggt gggctgccgg    420
cgctgcgccg ttgtgggcaa ctcgggcaac ctgagggagt cttcttatgg gcctgagata    480
gacagtcacg actttgtcct caggatgaac aaggcgccca cggcagggtt tgaagctgat    540
gttgggacca agaccaccca ccatctggtg taccctgaga gcttccggga gctgggagat    600
aatgtcagca tgatcctggt gcccttcaag accatcgact tggagtgggt ggtgagcgcc    660
atcaccacgg gcaccatttc ccacacctac atcccggttc ctgcaaagat cagagtgaaa    720
caggataaga tcctgatcta ccacccagcc ttcatcaagt atgtctttga caactggctg    780
caagggcacg ggcgataccc atctaccggc atcctctcgg tcatcttctc aatgcatgtc    840
tgcgatgagg tggacttgta cggcttcggg gcagacagca aagggaactg gcaccactac    900
tgggagaaca acccatccgc gggggctttt cgcaagacgg gggtgcacga tgcagacttt    960
gagtctaacg tgacggccac cttggcctcc atcaataaaa tccggatctt caaggggaga    1020
tga                                                                  1023
```

METHODS FOR PREPARING MODIFIED VON WILLEBRAND FACTOR

This application is the United States national stage entry under 35 U.S.C. § 371 of International Application No. PCT/EP2016/061440, filed on May 20, 2016 and published as WO 2016/188905 A1, which claims priority to European Patent Application No. 15168934.6, filed on May 22, 2015. The contents of these applications are each incorporated herein by reference in their entirety.

FIELD OF THE INVENTION

The present invention relates to products and methods for improving treatment of blood coagulation disorders.

BACKGROUND OF THE INVENTION

There are various bleeding disorders caused by deficiencies of blood coagulation factors. The most common disorders are hemophilia A and B, resulting from deficiencies of blood coagulation Factor VIII (FVIII) and IX, respectively. Another known bleeding disorder is von Willebrand's disease (VWD).

In plasma FVIII exists mostly as a noncovalent complex with von Willebrand Factor (VWF), and its coagulant function is to accelerate Factor IXa dependent conversion of Factor X to Xa.

Classic hemophilia or hemophilia A is an inherited bleeding disorder. It results from a chromosome X-linked deficiency of blood coagulation FVIII, and affects almost exclusively males with an incidence of between one and two individuals per 10,000. The X-chromosome defect is transmitted by female carriers who are not themselves hemophiliacs. The clinical manifestation of hemophilia A is an increased bleeding tendency.

In severe hemophilia A patients undergoing prophylactic treatment FVIII has to be administered intravenously (i.v.) about 3 times per week due to the short plasma half-life of FVIII of about 12 to 14 hours. Each i.v. administration is cumbersome, associated with pain and entails the risk of an infection especially as this is mostly done at home by the patients themselves or by the parents of children having been diagnosed for hemophilia A. It would thus be highly desirable to increase the half-life of FVIII so that pharmaceutical compositions containing such FVIII would have to be administered less frequently.

Several attempts have been made to prolong the half-life of non-activated FVIII either by reducing its interaction with cellular receptors (WO 03/093313 A2, WO 02/060951 A2), by covalently attaching polymers to FVIII (WO 94/15625, WO 97/11957 and U.S. Pat. No. 4,970,300), by encapsulation of FVIII (WO 99/55306), by introduction of novel metal binding sites (WO 97/03193), by covalently attaching the A2 domain to the A3 domain either by peptidic (WO 97/40145 and WO 03/087355) or disulfide linkage (WO 02/103024A2) or by covalently attaching the A1 domain to the A2 domain (WO2006/108590).

Another approach to enhance the functional half-life of FVIII or VWF is by PEGylation of FVIII (WO 2007/126808, WO 2006/053299, WO 2004/075923) or by PEGylation of VWF (WO 2006/071801). The increased half-life of pegylated VWF would indirectly also enhance the half-life of FVIII present in plasma. Also fusion proteins of FVIII have been described (WO 2004/101740, WO2008/077616 and WO 2009/156137).

VWF, which is missing, functionally defect or only available in reduced quantity in different forms of von Willebrand disease (VWD), is a multimeric adhesive glycoprotein present in the plasma of mammals, which has multiple physiological functions. During primary hemostasis VWF acts as a mediator between specific receptors on the platelet surface and components of the extracellular matrix such as collagen. Moreover, VWF serves as a carrier and stabilizing protein for procoagulant FVIII. VWF is synthesized in endothelial cells and megakaryocytes as a 2813 amino acid precursor molecule. The amino acid sequence and the cDNA sequence of wild-type VWF are disclosed in Collins et al. 1987, Proc. Natl. Acad. Sci. USA 84:4393-4397. The precursor polypeptide, pre-pro-VWF, consists of an N-terminal 22-residue signal peptide, followed by a 741-residue pro-peptide and the 2050-residue polypeptide found in mature plasma VWF (Fischer et al., FEBS Lett. 351: 345-348, 1994). After cleavage of the signal peptide in the endoplasmatic reticulum a C-terminal disulfide bridge is formed between two monomers of VWF. During further transport through the secretory pathway 12 N-linked and 10 O-linked carbohydrate side chains are added. More important, VWF dimers are multimerized via N-terminal disulfide bridges and the propeptide of 741 amino acids length is cleaved off by the enzyme PACE/furin in the late Golgi apparatus.

Once secreted into plasma the protease ADAMTS13 can cleave high-molecular weight VWF multimers within the A1 domain of VWF. Plasma VWF therefore consists of a whole range of multimers ranging from single dimers of 500 kDa to multimers consisting of up to more than 20 dimers of a molecular weight of over 10,000 kDa. The VWF-HMWM hereby having the strongest hemostatic activity, which can be measured in ristocetin cofactor activity (VWF:RCo). The higher the ratio of VWF:RCo/VWF antigen, the higher the relative amount of high molecular weight multimers.

In plasma FVIII binds with high affinity to VWF, which protects it from premature elimination and thus, plays in addition to its role in primary hemostasis a crucial role to stabilize FVIII, regulate plasma levels of FVIII and as a consequence is also a central factor to control secondary hemostasis. The half-life of non-activated FVIII bound to VWF is about 12 to 14 hours in plasma. In von Willebrand disease type 3, where no or almost no VWF is present, the half-life of FVIII is only about 2 to 6 hours, leading to symptoms of mild to moderate hemophilia A in such patients due to decreased concentrations of FVIII. The stabilizing effect of VWF on FVIII has also been used to aid recombinant expression of FVIII in CHO cells (Kaufman et al. 1989, Mol Cell Biol 9:1233-1242).

VWF-derived polypeptides, in particular VWF fragments, have been described to stabilize FVIII in vitro and in vivo. WO 2013/106787 A1 is directed at chimeric proteins comprising certain VWF fragments and a FVIII protein. WO 2014/198699 A2 and WO 2013/083858 A2 describe VWF fragments and their use in the treatment of hemophilia. WO 2011/060242 A2 discloses fusion polypeptides comprising certain VWF fragments and an antibody Fc region. WO2013/093760 A2 describes a method for preparing a protein, comprising co-expressing FVIII or VWF polypeptides, including truncated forms of VWF, with a recombinant α-2,3-sialyltransferase. Yee et al. (2014) Blood 124(3):445-452 found that a VWF fragment containing the D'D3 domains is sufficient to stabilize Factor VIII in mice. However, although a VWF D'D3-Fc fusion protein exhibited markedly prolonged survival when transfused into FVIII-deficient mice, the VWF D'D3-Fc fusion protein did not prolong the survival of co-transfused FVIII.

The effect of the fermentation temperature on the sialylation level of a glycoprotein was investigated by Trummer et al (Biotech. Bioeng. (2006) Vol. 94, No. 6, p. 1033-1044) who found for erythropoietin at 30° C. a decrease in sialylation by 40% and at 33° C. a decrease by 20%.

Ahn et al. also investigated the effect of fermentation temperature on the sialylation level of a glycoprotein and published for erythropoietin (Biotech. Bioeng. (2008) Vol. 101, No. 6, p. 1234-1244) a percentage of asialo glycoprotein at 37° C. of 2.4%, and at 32° C. of 2.1%.

There is an ongoing need for methods increasing the half-life of FVIII and FVIII products with reduced administration frequency.

SUMMARY OF THE INVENTION

It has been found by the inventors that the sialylation of N-glycans of VWF fragments can be significantly increased if mammalian cells transfected with recombinant DNA encoding a VWF fragment are cultured at a lowered temperature, e.g. below 36° C. The products obtained in this way exhibit improved pharmacokinetics and a prolonged mean residence time (MRT) and can be used to also improve pharmacokinetics and prolong MRT of a co-administered FVIII. It has been found by the inventors that the clearance of FVIII can be significantly reduced by co-administration of a half-life extended VWF-derived polypeptide which is characterized by a high degree of sialylation of its N-glycans. They are therefore particularly suitable for treating blood coagulation disorders. Especially VWF fragments capable of binding to FVIII which comprise N-glycans wherein more than 75% of all N-glycans on average have at least one sialic acid have been shown to be particularly useful.

Another advantage of the method of the present invention as described above is that the VWF fragments obtained have a higher proportion of dimers than VWF fragments produced in a conventional manner. The inventors found that the dimers have a higher affinity to FVIII than the monomers.

In particular preferred embodiments of the invention the VWF-derived polypeptide of the invention may be connected to a half-life extending moiety and is characterized by a high degree of sialylation of its N-glycans and has a particular low amount of N-glycans with multivalent terminal and non-sialylated galactose residues, including a particular low amount of N-glycans with two or more terminal and non-sialylated galactose residues, and even more preferred a particular low amount of N-glycans with three or more terminal and non-sialylated galactose residues.

The present invention therefore relates to the following embodiments [1] to [53]:

[1] A method of producing a glycoprotein comprising N-glycans with increased sialylation, which comprises (i) providing cells comprising a nucleic acid encoding a polypeptide comprising a truncated von Willebrand Factor (VWF), and (ii) culturing said cells at a temperature of less than 36.0° C., wherein said polypeptide comprising a truncated VWF preferably has a circulatory mean residence time (MRT) greater than that of full-length VWF.

[2] A method of producing a dimer of a glycoprotein comprising a truncated von Willebrand Factor (VWF), which comprises (i) providing cells comprising a nucleic acid encoding the amino acid sequence of the glycoprotein, and (ii) culturing said cells at a temperature of less than 36.0° C.

[3] A method of increasing the dimerization of a glycoprotein comprising a truncated von Willebrand Factor (VWF), which comprises (i) providing cells comprising a nucleic acid encoding amino acid sequence of the glycoprotein, and (ii) culturing said cells at a temperature of less than 36.0° C.

[4] The method of any one of the preceding items, wherein the cells further comprise a recombinant nucleic acid encoding a sialyltransferase, preferably an α-2,6-sialyltransferase and/or an α-2,3-sialyltransferase.

[5] The method of any one of the preceding items, wherein prior to step (ii) the cells are cultured at a temperature of 37.0° C.±1.0° C., and step (ii) comprises culturing the cells at a temperature of 34.0° C.±2.0° C.

[6] A method of producing a glycoprotein comprising N-glycans with increased sialylation, which comprises (i) providing cells comprising a nucleic acid encoding a polypeptide comprising a truncated von Willebrand Factor (VWF) and a recombinant nucleic acid encoding an α-2,6-sialyltransferase, and (ii) culturing the cells under conditions that allow expression of the glycoprotein.

[7] The method of any one of the preceding items, wherein the cells are transfected mammalian cells, and step (i) comprises introducing into mammalian cells the nucleic acid encoding a polypeptide comprising the truncated VWF, and optionally the recombinant nucleic acid encoding a sialyltransferase.

[8] The method of any one of the preceding items, further comprising the step of recovering the glycoprotein from the culture medium.

[9] The method of any one of the preceding items, further comprising subjecting the glycoprotein obtained in any one of the preceding items to ion exchange chromatography, whereby glycoprotein with high sialylation is separated from glycoprotein with low sialylation; and collecting the fractions eluted from the ion exchange column having high sialylation.

[10] The method of any one of the preceding items, further comprising contacting the glycoprotein obtained in any one of the preceding items with a sialyltransferase and a sialic acid donor in vitro.

[11] The method of item [10], wherein the sialyltransferase is an α-2,6-sialyltransferase, an α-2,3-sialyltransferase, or a combination thereof.

[12] The method of any one of the preceding items, wherein the glycoprotein further comprises a half-life extending heterologous polypeptide fused to the truncated VWF.

[13] The method of item [12], wherein the half-life extending heterologous polypeptide comprises or consists of a polypeptide selected from the group consisting of albumin or a fragment thereof having a length of at least 100 amino acids, immunoglobulin constant regions and portions thereof, e.g. the Fc fragment, transferrin and fragments thereof, the C-terminal peptide of human chorionic gonadotropin, solvated random chains with large hydrodynamic volume known as XTEN, homo-amino acid repeats (HAP), proline-alanine-serine repeats (PAS), albumin, afamin, alpha-fetoprotein, Vitamin D binding protein, polypeptides capable of binding under physiological conditions to albumin or immunoglobulin constant regions, and combinations thereof.

[14] The method of any one of items [1] to [11], comprising conjugating the glycoprotein obtained in any one of the preceding items with the half-life-extending moiety.

[15] The method of item [14], wherein the half-life-extending moiety is selected from the group consisting of hydroxyethyl starch (HES), polyethylene glycol (PEG), polysialic acids (PSAs) and albumin binding ligands, e.g. fatty acid chains.

[16] The method of any one of the preceding items, wherein, on average, at least 75% of the N-glycans of the obtained glycoprotein comprise at least one sialic acid moiety.

[17] The method of any one of the preceding items, wherein, on average, at least 80% of the N-glycans of the obtained glycoprotein comprise at least one sialic acid moiety.

[18] The method of any one of the preceding items, wherein, on average, at least 85% of the N-glycans of the obtained glycoprotein comprise at least one sialic acid moiety.

[19] The method of any one of the preceding items, wherein, on average, at least 50% of the obtained glycoprotein is present as dimer.

[20] A glycoprotein obtainable by a method of any one of the preceding items.

[21] A glycoprotein comprising a truncated von Willebrand Factor (VWF), wherein said truncated VWF is capable of binding to a Factor VIII (FVIII), and wherein said glycoprotein comprises N-glycans, and at least 75%, preferably at least 85%, more preferably at least 90%, preferably at least 95%, preferably at least 96%, preferably at least 97%, preferably at least 98%, more preferably at least 99% of said N-glycans comprise, on average, at least one sialic acid moiety.

[22] A glycoprotein comprising a truncated von Willebrand Factor (VWF), wherein said truncated VWF is capable of binding to a Factor VIII (FVIII), and wherein said glycoprotein comprises N-glycans, wherein less than 35%, preferably less than 34%, preferably less than 33%, preferably less than 32%, preferably less than 31%, preferably less than 30%, preferably less than 29%, preferably less than 28%, preferably less than 27% preferably less than 26%, preferably less than 25%, preferably less than 24%, preferably less than 23%, preferably less than 22%, preferably less than 21%, preferably less than 20%, preferably less than 19%, preferably less than 18%, preferably less than 17%, preferably less than 16%, preferably less than 15%, preferably less than 14%, preferably less than 13%, preferably less than 12%, preferably less than 11%, preferably less than 10%, preferably less than 9%, preferably less than 8%, preferably less than 7%, preferably less than 6% and preferably less than 5% of said N-glycans comprise, on average, two or more terminal and non-sialylated galactose residues.

[23] A glycoprotein according to items [21] and [22].

[24] A glycoprotein comprising a truncated von Willebrand Factor (VWF), wherein said truncated VWF is capable of binding to a Factor VIII (FVIII), and wherein said glycoprotein comprises N-glycans, wherein less than 6%, preferably less than 5%, preferably less than 4%, preferably less than 3%, preferably less than 2%, and preferably less than 1% of said N-glycans comprise, on average, three or more terminal and non-sialylated galactose residues.

[25] A glycoprotein according to items [21] and [24] or to items [22] and [24] or to items [23] and [24].

[26] The glycoprotein of items [21] to [25], wherein at least 70% of said N-glycans comprise, on average, at least one α-2,6-sialic acid moiety or one α-2,3-sialic acid moiety.

[27] The glycoprotein of any one of items [20] to [26], wherein the truncated VWF comprises (a) amino acids 776 to 805 of SEQ ID NO:9 or (b) an amino acid sequence having a sequence identity of at least 90% to amino acids 776 to 805 of SEQ ID NO:9.

[28] The glycoprotein of any one of items [20] to [27], wherein the truncated VWF comprises (a) amino acids 766 to 864 of SEQ ID NO:9 or (b) an amino acid sequence having a sequence identity of at least 90% to amino acids 766 to 864 of SEQ ID NO:9.

[29] The glycoprotein of any one of items [20] to [28], wherein the truncated VWF consists of (a) amino acids 764 to 1242 of SEQ ID NO:9, (b) an amino acid sequence having a sequence identity of at least 90% to amino acids 764 to 1242 of SEQ ID NO:9, or (c) a fragment of (a) or (b).

[30] The glycoprotein of any one of items [20] to [29], further comprising a half-life extending heterologous polypeptide fused to the truncated VWF, and/or a half-life-extending moiety conjugated to the glycoprotein.

[31] The glycoprotein of item [30], wherein said half-life extending heterologous polypeptide comprises or consists of human serum albumin or a fragment thereof, wherein the length of said fragment is at least 100 amino acids.

[32] The glycoprotein of item [30], wherein said heterologous polypeptide fused to the glycoprotein comprises or consists of a polypeptide selected from the group consisting of immunoglobulin constant regions and portions thereof, e.g. the Fc fragment, transferrin and fragments thereof, the C-terminal peptide of human chorionic gonadotropin, solvated random chains with large hydrodynamic volume known as XTEN, homo-amino acid repeats (HAP), proline-alanine-serine repeats (PAS), albumin, afamin, alpha-feto-protein, Vitamin D binding protein, polypeptides capable of binding under physiological conditions to albumin or immunoglobulin constant regions, and combinations thereof.

[33] The glycoprotein of item [30], wherein said half-life-extending moiety conjugated to the glycoprotein is selected from the group consisting of hydroxyethyl starch (HES), polyethylene glycol (PEG), polysialic acids (PSAs), elastin-like polypeptides, heparosan polymers, hyaluronic acid and albumin binding ligands, e.g. fatty acid chains.

[34] The glycoprotein of any one of items [20] to [33], wherein the glycoprotein is a dimer.

[35] The dimeric glycoprotein of item [34], wherein the affinity of said dimeric glycoprotein to the FVIII is greater than the affinity of a monomeric glycoprotein to said FVIII, wherein said monomeric glycoprotein has the same amino acid sequence as the dimeric glycoprotein.

[36] The glycoprotein of any one of items [20] to [35], wherein said truncated VWF has one or more amino acid substitution(s) relative to the amino acid sequence shown in SEQ ID NO:9, wherein the truncated VWF having said one or more amino acid substitutions has a greater affinity to FVIII than a truncated VWF consisting of the same amino acid sequence except for said one or more amino acid substitutions relative to SEQ ID NO:9.

[37] The glycoprotein of item [36], wherein the affinity of said glycoprotein to the FVIII is greater than the affinity of a reference polypeptide, wherein the amino acid sequence of said reference polypeptide is identical to the amino acid sequence of said glycoprotein except that the amino acid sequence of the truncated VWF of the reference polypeptide does not have said one or more substitutions relative to the amino acids sequence shown in SEQ ID NO:9.

[38] A composition comprising a population of glycoproteins as defined in any one of items [20] to [37], wherein the ratio of dimeric glycoprotein to monomeric glycoprotein in the composition is greater than 1.0, preferably greater than 1.5, more preferably greater than 2.0, most preferably greater than 2.5.

[39] A pharmaceutical composition comprising a glycoprotein of any one of items [20] to [37] and a pharmaceutically acceptable excipient.

[40] The pharmaceutical composition of item [39], wherein at least 50%, at least 60%, at least 70%, at least 80% or at least 90% of the glycoproteins in the composition are present as dimers.

[41] A glycoprotein as defined in any one of items [20] to [37] for use in the treatment of a blood coagulation disorder, said treatment comprising administering to a subject an effective amount of said glycoprotein.

[42] The glycoprotein for use according to item [41], wherein said treatment further comprises administering to the subject an effective amount of a FVIII.

[43] The glycoprotein for use according to item [42], wherein the plasma MRT of the FVIII is increased, and/or the clearance of the FVIII is reduced, by the co-administration of the glycoprotein, as compared to a treatment with the FVIII alone.

[44] The glycoprotein for use according to item [42] or [43], wherein the frequency of administration of the FVIII is reduced as compared to a treatment with the FVIII alone.

[45] The glycoprotein for use according to any one of items [42] to [44], wherein the glycoprotein and/or the FVIII is/are administered intravenously.

[46] The glycoprotein for use according to any one of items [42] to [44], wherein the glycoprotein and/or the FVIII is/are administered subcutaneously.

[47] The glycoprotein for use according to any one of items [42] to [46], wherein the glycoprotein and the FVIII are administered separately.

[48] The use of a glycoprotein as defined in any one of items [20] to [37] for increasing the plasma MRT of Factor VIII.

[49] The use of a glycoprotein as defined in any one of items [20] to [37] for reducing the clearance of administered FVIII from the circulation.

[50] The use of item [48] or [49], wherein said Factor VIII is exogenously administered to a subject having hemophilia A.

[51] A pharmaceutical kit comprising (i) a FVIII and (ii) a glycoprotein as defined in any one of items [20] to [37] for simultaneous, separate or sequential use in the treatment of a blood coagulation disorder.

[52] A method of treating a blood coagulation disorder, comprising administering to a patient in need thereof an effective amount of a glycoprotein as defined in any one of items [20] to [37].

[53] A method of extending the circulatory half-life of an exogenously administered FVIII, which comprises co-administering the glycoprotein of any one of items [20] to [37].

DESCRIPTION OF THE DRAWINGS

FIG. 5: Legend to the glycostructures shown in FIGS. 6 to 25

DETAILED DESCRIPTION

Figure 1:
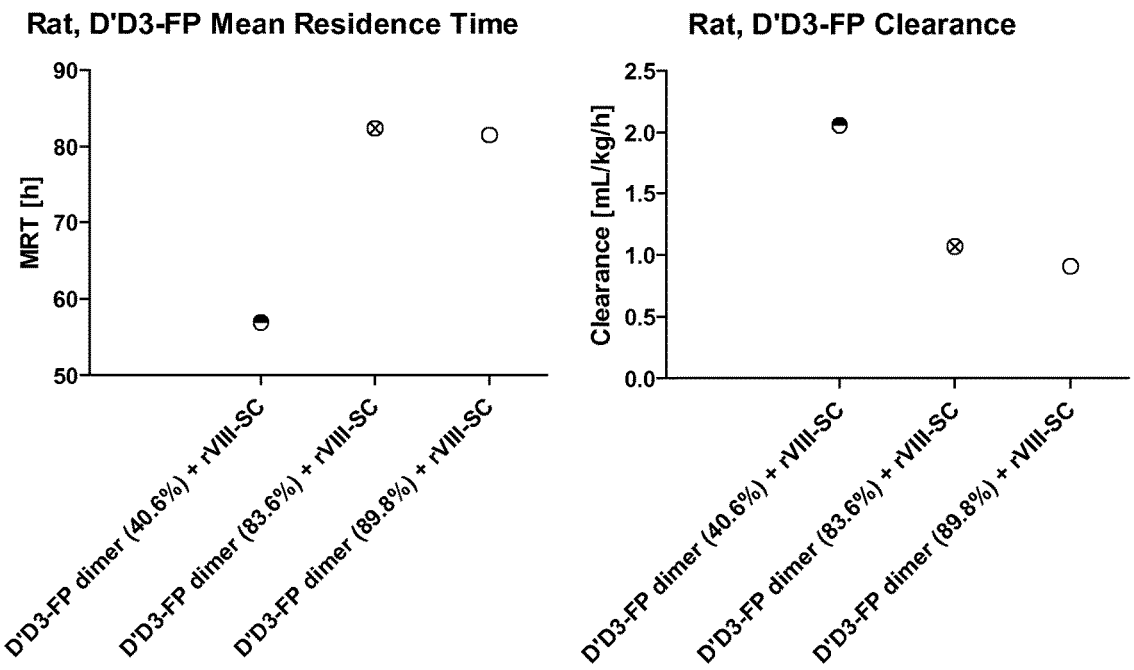
FIG. 1: Mean residence time and clearance (mean) of D'D3-FP dimer quantified as albumin in rats, as determined in Example 8.1.

In a first aspect, the present invention pertains to a method of producing a glycoprotein comprising sialylated N-glycans, which comprises (i) providing cells comprising a nucleic acid encoding a polypeptide comprising a truncated von Willebrand Factor (VWF), and (ii) culturing said cells at a temperature of less than 36.0° C. Preferably, the N-glycans of the produced glycoprotein have an increased sialylation, and/or a high degree of sialylation.

In a second aspect, the present invention pertains to a method of producing a glycoprotein comprising sialylated N-glycans, which comprises (i) providing cells comprising a nucleic acid encoding a polypeptide comprising a truncated von Willebrand Factor (VWF) and a recombinant nucleic acid encoding an α-2,3-sialyltransferase and/or an α-2,6-sialyltransferase, and (ii) culturing the cells under conditions that allow expression of the glycoprotein and of the sialyltransferase(s). Preferably, the N-glycans of the produced glycoprotein have an increased sialylation, and/or a high sialylation.

The term "glycoprotein", as used herein, refers to a protein or polypeptide that comprises one or more covalently linked oligosaccharide chains. The oligosaccharide chains may be composed of a single unbranched chain of sugar residues or may be composed of a chain of sugar residues that branches one or more times.

"N-linked glycans" are oligosaccharides that are covalently linked to asparagine residues of a polypeptide. Terminal galactoses on such N-linked glycans may be modified by the attachment of an α-2,3- or an α-2,6-linked sialic acid (as shown in FIGS. 5 to 25). Preferably the terminal galactoses are D-galactoses. N-glycans are usually branched and can be, for example, of a bi-, tri- or tetra-antennary type, so that there could be two, three or four terminal galactose residues in one N-glycan, which may be sialylated to varying degrees or be all non-sialylated. "Terminal" refers to the most distant position in a given branch of an N-glycan from the attachment point of the N-glycan to the peptidic chain of the glycoprotein of the invention.

The term "sialic acid" refers to the N- or O-substituted derivatives of neuraminic acid usually found as terminal monosaccharides of animal oligosaccharides (for review, see Varkis (1992) Glycobiology vol. 2 no. 1 pp. 25-40). The most common sialic acid is N-acetyl neuraminic acid. An "increased sialylation" means that at least 75% of the N-glycans of the glycoprotein comprise, on average, at least one sialic acid moiety. By way of non-limiting example an "increased sialylation of at least 75%" is determined as in Example 6 of the present invention, i.e. by enzymatically cleaving all N-glycans from a given glycoprotein of interest and then determining the amount of cleaved N-glycans with no sialic acids ("asialo N-glycans") and the total amount of all cleaved N-glycans. A "sialylation of at least 75%" corresponds then to an amount of 25% of asialo N-glycans or less of the total amount of all cleaved N-glycans.

Increased sialylation is of importance for maintaining a given therapeutic glycoprotein longer in the circulation since glycoproteins with a reduced sialylation bind to the asialoglycoprotein receptor (ASGP-R) and are then—after receptor mediated endocytosis—finally degraded.

The ASGP-R is expressed exclusively by parenchymal hepatocytes, which contain 100,000-500,000 binding sites per cell. These receptors are randomly distributed over the sinusoidal plasma membrane facing the blood capillaries. Their main function is to maintain plasma glycoprotein homeostasis by recognition, binding and endocytosis of asialoglycoproteins (Stokmaier et al (2009) Bioorganic & Medicinal Chemistry, 7254-7264).

The human ASGP-R consists of two homologous subunits, designated H1 and H2, which form a non-covalent heteroligomeric complex with an estimated ratio of 2-5:1, respectively. This ASGP-R complex binds to glycoproteins exposing glycostructures with non-sialylated terminal D-galactose and N-acetyl-D-galactoseamin residues. It has been found that the binding affinity of glycostructures to the ASGP-R strongly depends on the valency of the ligand. Whereas the affinity of a single D-galactose residue is only in the millimolar range, bi-, tri- and tetraantennary desialylated glycans bind with dissociation constants of $10^{-6}$, $5 \times 10^{-9}$ and $10^{-9}$ M, respectively.

Therefore in particular preferred embodiments of the invention the glycoprotein of the invention which is characterized by a high degree of sialylation of its N-glycans has a particular low amount of N-glycans with multivalent terminal and non-sialylated galactose residues, including a particular low amount of N-glycans with two or more terminal and non-sialylated galactose residues, and even more preferred a particular low amount of N-glycans with three or more terminal and non-sialylated galactose residues.

In a first step, the methods of the invention comprise the step of providing cells comprising a nucleic acid encoding a polypeptide comprising a truncated von Willebrand Factor (VWF).

The Truncated VWF

The term "von Willebrand Factor" (VWF) as used herein includes naturally occurring (native) VWF, but also variants thereof retaining at least the FVIII binding activity of naturally occurring VWF, e.g. sequence variants where one or more residues have been inserted, deleted or substituted. The FVIII binding activity is determined by a FVIII-VWF binding assay as described in Example 11.

The preferred VWF in accordance with this invention is human VWF represented by the amino acid sequence shown in SEQ ID NO:9. The cDNA encoding SEQ ID NO:9 is shown in SEQ ID NO:8.

The gene encoding human native VWF is transcribed into a 9 kb mRNA which is translated into a pre-propolypeptide of 2813 amino acids with an estimated molecular weight of 310,000 Da. The pre-propolypeptide contains an N-terminal 22 amino acids signal peptide, followed by a 741 amino acid pro-polypeptide (amino acids 23-763 of SEQ ID NO:9) and the mature subunit (amino acids 764-2813 of SEQ ID NO:9). Cleavage of the 741 amino acids propolypeptide from the N-terminus results in mature VWF consisting of 2050 amino acids. The amino acid sequence of the human native VWF pre-propolypeptide is shown in SEQ ID NO:9. Unless indicated otherwise, the amino acid numbering of VWF residues in this application refers to SEQ ID NO:9, even if the VWF molecule does not comprise all residues of SEQ ID NO:9.

The propolypeptide of native VWF comprises multiple domains. Different domain annotations can be found in the literature (see, e.g. Zhou et al. (2012) Blood 120(2): 449-458). The following domain annotation of native pre-propolypeptide of VWF is applied in this application:

D1-D2-D'-D3-A1-A2-A3-D4-C1-C2-C3-C4-C5-C6-CK

With reference to SEQ ID NO:9, the D' domain consists of amino acids 764-865; and the D3 domain consists of amino acids 866-1242.

The feature "truncated" means that the polypeptide does not comprise the entire amino acid sequence of mature VWF (amino acids 764-2813 of SEQ ID NO:9). Typically, the truncated VWF does not comprise all amino acids 764-2813 of SEQ ID NO:9 but only a fragment thereof. A truncated VWF may also be referred to as a VWF fragment, or in the plural as VWF fragments.

Typically, the truncated VWF is capable of binding to a Factor VIII. Preferably, the truncated VWF is capable of binding to the mature form of human native Factor VIII. In another embodiment, the truncated VWF is capable of binding to the single-chain Factor VIII consisting of the amino acid sequence SEQ ID NO:10. Binding of the truncated VWF to Factor VIII can be determined by a FVIII-VWF binding assay as described in Example 11.

The truncated VWF of the present invention preferably comprises or consists of an amino acid sequence having a sequence identity of at least 90% to amino acids 776 to 805 of SEQ ID NO:9 and is capable of binding to FVIII. In preferred embodiments the truncated VWF comprises or consists of an amino acid sequence having a sequence identity of at least 95%, at least 96%, at least 97%, at least 98%, or at least 99%, to amino acids 776 to 805 of SEQ ID NO:9 and is capable of binding to FVIII. Most preferably, the truncated VWF comprises or consists of amino acids 776 to 805 of SEQ ID NO:9. Unless indicated otherwise herein, sequence identities are determined over the entire length of the reference sequence (e.g. amino acids 776 to 805 of SEQ ID NO:9).

The truncated VWF of the present invention preferably comprises or consists of an amino acid sequence having a sequence identity of at least 90% to amino acids 766 to 864 of SEQ ID NO:9 and is capable of binding to FVIII. In preferred embodiments the truncated VWF comprises or consists of an amino acid sequence having a sequence identity of at least 95%, at least 96%, at least 97%, at least 98%, or at least 99%, to amino acids 766 to 864 of SEQ ID NO:9 and is capable of binding to FVIII. Most preferably, the truncated VWF comprises or consists of amino acids 766 to 864 of SEQ ID NO:9.

In another preferred embodiment, the truncated VWF consists of (a) an amino acid sequence having a sequence identity of at least 90% to amino acids 764 to 1242 of SEQ ID NO:9, or (b) a fragment thereof, provided that the truncated VWF is still capable of binding to FVIII. More preferably, the truncated VWF consists of (a) an amino acid sequence having a sequence identity of at least 95%, at least 96%, at least 97%, at least 98%, or at least 99%, to amino acids 764 to 1242 of SEQ ID NO:9, or (b) a fragment thereof, provided that the truncated VWF is still capable of binding to FVIII. Most preferably, the truncated VWF consists of (a) amino acids 764 to 1242 of SEQ ID NO:9, or (b) a fragment thereof, provided that the truncated VWF is still capable of binding to FVIII.

As described in more detail below, the method of the invention comprises providing cells comprising a nucleic acid encoding the polypeptide comprising the truncated VWF. The nucleic acid is introduced into suitable host cells by techniques that are known per se.

In a preferred embodiment, the nucleic acid in the host cell encodes (a) an amino acid sequence having a sequence identity of at least 90% to amino acids 1 to 1242 of SEQ ID NO:9, or (b) a fragment thereof, provided that the truncated mature VWF is still capable of binding to FVIII. More preferably, the nucleic acid encodes (a) an amino acid sequence having a sequence identity of at least 95%, at least 96%, at least 97%, at least 98%, or at least 99%, to amino acids 1 to 1242 of SEQ ID NO:9, or (b) a fragment thereof, provided that the truncated VWF is still capable of binding to FVIII. Most preferably, the nucleic acid encodes (a) amino acids 1 to 1242 of SEQ ID NO:9, or (b) a fragment thereof, provided that the truncated VWF is still capable of binding to FVIII. Especially if the glycoprotein eventually produced is a dimer, the nucleic acid will comprise a sequence encoding amino acids 1 to 763 of VWF (e.g. SEQ ID NO:9), even if the truncated VWF in the glycoprotein does not comprise amino acids 1 to 763 of VWF (e.g. SEQ ID NO:9).

In other embodiments the truncated VWF comprises or consists of one of the following amino acid sequences, each referring to SEQ ID NO:9:

776-805; 766-805; 764-805; 776-810; 766-810; 764-810; 776-815; 766-815; 764-815;

776-820; 766-820; 764-820; 776-825; 766-825; 764-825; 776-830; 766-830; 764-830;

776-835; 766-835; 764-835; 776-840; 766-840; 764-840; 776-845; 766-845; 764-845;

776-850; 766-850; 764-850; 776-855; 766-855; 764-855; 776-860; 766-860; 764-860;

776-864; 766-864; 764-864; 776-865; 766-865; 764-865; 776-870; 766-870; 764-870;

776-875; 766-875; 764-875; 776-880; 766-880; 764-880; 776-885; 766-885; 764-885;

776-890; 766-890; 764-890; 776-895; 766-895; 764-895; 776-900; 766-900; 764-900;
776-905; 766-905; 764-905; 776-910; 766-910; 764-910; 776-915; 766-915; 764-915;
776-920; 766-920; 764-920; 776-925; 766-925; 764-925; 776-930; 766-930; 764-930;
776-935; 766-935; 764-935; 776-940; 766-940; 764-940; 776-945; 766-945; 764-945;
776-950; 766-950; 764-950; 776-955; 766-955; 764-955; 776-960; 766-960; 764-960;
776-965; 766-965; 764-965; 776-970; 766-970; 764-970; 776-975; 766-975; 764-975;
776-980; 766-980; 764-980; 776-985; 766-985; 764-985; 776-990; 766-990; 764-990;
776-995; 766-995; 764-995; 776-1000; 766-1000; 764-1000; 776-1005; 766-1005; 764-1005;
776-1010; 766-1010; 764-1010; 776-1015; 766-1015; 764-1015; 776-1020; 766-1020; 764-1020;
776-1025; 766-1025; 764-1025; 776-1030; 766-1030; 764-1030; 776-1035; 766-1035; 764-1035;
776-1040; 766-1040; 764-1040; 776-1045; 766-1045; 764-1045; 776-1050; 766-1050; 764-1050;
776-1055; 766-1055; 764-1055; 776-1060; 766-1060; 764-1060; 776-1065; 766-1065; 764-1065;
776-1070; 766-1070; 764-1070; 776-1075; 766-1075; 764-1075; 776-1080; 766-1080; 764-1080;
776-1085; 766-1085; 764-1085; 776-1090; 766-1090; 764-1090; 776-1095; 766-1095; 764-1095;
776-1100; 766-1100; 764-1100; 776-1105; 766-1105; 764-1105; 776-1110; 766-1110; 764-1110;
776-1115; 766-1115; 764-1115; 776-1120; 766-1120; 764-1120; 776-1125; 766-1125; 764-1125;
776-1130; 766-1130; 764-1130; 776-1135; 766-1135; 764-1135; 776-1140; 766-1140; 764-1140;
776-1145; 766-1145; 764-1145; 776-1150; 766-1150; 764-1150; 776-1155; 766-1155; 764-1155;
776-1160; 766-1160; 764-1160; 776-1165; 766-1165; 764-1165; 776-1170; 766-1170; 764-1170;
776-1175; 766-1175; 764-1175; 776-1180; 766-1180; 764-1180; 776-1185; 766-1185; 764-1185;
776-1190; 766-1190; 764-1190; 776-1195; 766-1195; 764-1195; 776-1200; 766-1200; 764-1200;
776-1205; 766-1205; 764-1205; 776-1210; 766-1210; 764-1210; 776-1215; 766-1215; 764-1215;
776-1220; 766-1220; 764-1220; 776-1225; 766-1225; 764-1225; 776-1230; 766-1230; 764-1230;
776-1235; 766-1235; 764-1235; 776-1240; 766-1240; 764-1240; 776-1242; 766-1242; 764-1242;
764-1464; 764-1250; 764-1041; 764-828; 764-865; 764-1045; 764-1035; 764-1128; 764-1198;
764-1268; 764-1261; 764-1264; 764-1459; 764-1463; 764-1464; 764-1683; 764-1873; 764-1482;
764-1479; 764-1672; and 764-1874.

In certain embodiments the truncated VWF has an internal deletion relative to mature wild type VWF. For example, the A1, A2, A3, D4, C1, C2, C3, C4, C5, C6 domains or combinations thereof may be deleted, and the D' domain, the D3 domain and the CK domain is retained. In further embodiments the truncated VWF does not comprise the binding sites for platelet glycoprotein Ibα (GPIbα), collagen and/or integrin αIIbβIII (RGDS sequence within the C1 domain). In other embodiments, the truncated VWF does not comprise the cleavage site (Tyr1605-Met1606) for ADAMTS13 which is located at the central A2 domain of VWF. In yet another embodiment, the truncated VWF does not comprise the binding sites for GPIbα, and/or does not comprise the binding site for collagen, and/or does not comprise the binding site for integrin αIIbβIII, and/or it does not comprise the cleavage site (Tyr1605-Met1606) for ADAMTS13 which is located at the central A2 domain of VWF.

In other embodiments the truncated VWF comprises or consists of an amino acid sequence that has a sequence identity of at least 90%, or at least 91%, or at least 92%, or at least 93%, or at least 94%, or at least 95%, or at least 96%, or at least 97%, or at least 98%, or at least 99%, to one of the amino acid sequences recited in the preceding paragraph, provided that the truncated VWF is capable of binding to FVIII.

A glycoprotein is termed a "dimer" in the present invention if two monomers of the glycoprotein are linked covalently. Preferably the two monomeric subunits are covalently linked via at least one disulfide bridge, e.g. by one, two, three or four disulfide bridges. The cysteine residues forming the at least one disulfide bridge are preferably located within the truncated VWF portion of the glycoprotein. In one embodiment, these cysteine residues are Cys-1142, Cys-1222, Cys-1225, Cys-1227 and combinations thereof.

If the glycoprotein of the invention is a dimer, the truncated VWF preferably comprises or consists of two polypeptides each with an amino acid sequence having a sequence identity of at least 90% to amino acids 764 to 1099, amino acids 764 to 1142, amino acids 764 to 1222, amino acids 764 to 1225, or amino acids 764 to 1227 of SEQ ID NO:9 and is capable of binding to FVIII. In preferred embodiments the truncated VWF comprises or consists of an amino acid sequence having a sequence identity of at least 95%, at least 96%, at least 97%, at least 98%, or at least 99%, to amino acids 764 to 1099, amino acids 764 to 1142, amino acids 764 to 1222, amino acids 764 to 1225, or amino acids 764 to 1227 of SEQ ID NO:9 and is capable of binding to FVIII. Most preferably, the truncated VWF comprises or consists of amino acids 764 to 1099, amino acids 764 to 1142, amino acids 764 to 1222, amino acids 764 to 1225, or amino acids 764 to 1227 of SEQ ID NO:9.

The truncated VWF may be any one of the VWF fragments disclosed in WO 2013/106787 A1, WO 2014/198699 A2, WO 2011/060242 A2 or WO 2013/093760 A2, the disclosure of which is incorporated herein by reference.

Further Components of the Polypeptide

In addition to the truncated VWF, the glycoprotein may further comprises a half-life extending moiety. The half-life-extending moiety may be a heterologous amino acid sequence fused to the truncated VWF. Alternatively, the half-life-extending moiety may be chemically conjugated to the polypeptide comprising the truncated VWF by a covalent bond different from a peptide bond.

In certain embodiments of the invention, the half-life of the glycoprotein is extended by chemical modification, e.g. attachment of a half-life extending moiety such as polyethylene glycol (PEGylation), glycosylated PEG, hydroxyl ethyl starch (HESylation), polysialic acids, elastin-like polypeptides, heparosan polymers or hyaluronic acid. In another embodiment, the glycoprotein is conjugated to a HLEP such as albumin via a chemical linker. The principle of this conjugation technology has been described in an exemplary manner by Conjuchem LLC (see, e.g., U.S. Pat. No. 7,256, 253).

In other embodiments, the half-life-extending moiety is a half-life enhancing protein (HLEP). Preferably, the HLEP is an albumin or a fragment thereof. The N-terminus of the albumin may be fused to the C-terminus of the truncated VWF. Alternatively, the C-terminus of the albumin may be fused to the N-terminus of the truncated VWF. One or more HLEPs may be fused to the N- or C-terminal part of VWF provided that they do not to interfere with or abolish the binding capability of the truncated VWF to FVIII.

In one embodiment the polypeptide has the following structure:

tVWF-L1-H      [formula 1]

Wherein tVWF is the truncated VWF, L1 is a chemical bond or a linker sequence, and H is a HLEP.

L1 may be a chemical bond or a linker sequence consisting of one or more amino acids, e.g. of 1 to 50, 1 to 30, 1 to 20, 1 to 15, 1 to 10, 1 to 5 or 1 to 3 (e.g. 1 , 2 or 3) amino acids and which may be equal or different from each other. Usually, the linker sequences are not present at the corresponding position in the wild-type VWF. Examples of suitable amino acids present in L1 include Gly and Ser. The linker should be non-immunogenic and may be a non-cleavable or cleavable linker. Non-cleavable linkers may be comprised of alternating glycine and serine residues as exemplified in WO2007/090584. In another embodiment of the invention the peptidic linker between the truncated VWF moiety and the albumin moiety consists of peptide sequences, which serve as natural interdomain linkers in human proteins. Preferably such peptide sequences in their natural environment are located close to the protein surface and are accessible to the immune system so that one can assume a natural tolerance against this sequence. Examples are given in WO2007/090584. Cleavable linker sequences are described, e.g., in WO 2013/120939 A1.

Preferred HLEP sequences are described infra. Likewise encompassed by the invention are fusions to the exact "N-terminal amino acid" of the respective HLEP, or fusions to the "N-terminal part" of the respective HLEP, which includes N-terminal deletions of one or more amino acids of the HLEP. The polypeptide may comprise more than one HLEP sequence, e.g. two or three HLEP sequences. These multiple HLEP sequences may be fused to the C-terminal part of VWF in tandem, e.g. as successive repeats.

In another embodiment of the invention, the half-life of the complex of the invention is extended by chemical modification, e.g. attachment of a half-life extending moiety such as polyethylene glycol (PEGylation), glycosylated PEG, hydroxyl ethyl starch (HESylation), polysialic acids, elastin-like polypeptides, heparosan polymers or hyaluronic acid. In another embodiment, the glycoprotein of the invention is conjugated to a HLEP such as albumin via a chemical linker. The principle of this conjugation technology has been described in an exemplary manner by Conjuchem LLC (see, e.g., U.S. Pat. No. 7,256,253).

Half-Life Enhancing Polypeptides (HLEPs)

Preferably, the half-life extending moiety is a half-life extending polypeptide (HLEP), more preferably HLEP is selected from albumin or fragments thereof, immunoglobulin constant region and portions thereof, e.g. the Fc fragment, solvated random chains with large hydrodynamic volume (e.g. XTEN (Schellenberger et al. 2009; Nature Biotechnol. 27:1186-1190), homo-amino acid repeats (HAP) or proline-alanine-serine repeats (PAS)), afamin, alpha-fetoprotein, Vitamin D binding protein, transferrin or variants thereof, carboxyl-terminal peptide (CTP) of human chorionic gonadotropin-ß subunit, polypeptides or lipids capable of binding under physiological conditions to albumin or immunoglobulin constant region.

A "half-life enhancing polypeptide" as used herein is preferably selected from the group consisting of albumin, a member of the albumin-family, the constant region of immunoglobulin G and fragments thereof, region and polypeptides capable of binding under physiological conditions to albumin, to members of the albumin family as well as to portions of an immunoglobulin constant region. It may be a full-length half-life-enhancing protein described herein (e.g. albumin, a member of the albumin-family or the constant region of immunoglobulin G) or one or more fragments thereof that are capable of stabilizing or prolonging the therapeutic activity or the biological activity of the coagulation factor. Such fragments may be of 10 or more amino acids in length or may include at least about 15, at least about 20, at least about 25, at least about 30, at least about 50, at least about 100, or more contiguous amino acids from the HLEP sequence or may include part or all of specific domains of the respective HLEP, as long as the HLEP fragment provides a functional half-life extension of at least 25% compared to the respective polypeptide without the HLEP.

The HLEP portion of the glycoprotein may be a variant of a wild type HLEP. The term "variants" includes insertions, deletions and substitutions, either conservative or non-conservative, where such changes do not substantially alter the FVIII-binding activity of the truncated VWF.

In particular, the proposed truncated VWF HLEP fusion constructs of the invention may include naturally occurring polymorphic variants of HLEPs and fragments of HLEPs. The HLEP may be derived from any vertebrate, especially any mammal, for example human, monkey, cow, sheep, or pig. Non-mammalian HLEPs include, but are not limited to, hen and salmon.

Albumin as HLEP

The terms, "human serum albumin" (HSA) and "human albumin" (HA) and "albumin" (ALB) are used interchangeably in this application. The terms "albumin" and "serum albumin" are broader, and encompass human serum albumin (and fragments and variants thereof) as well as albumin from other species (and fragments and variants thereof).

As used herein, "albumin" refers collectively to albumin polypeptide or amino acid sequence, or an albumin fragment or variant, having one or more functional activities (e.g., biological activities) of albumin. In particular, "albumin" refers to human albumin or fragments thereof, especially the mature form of human albumin as shown in SEQ ID NO:11 herein or albumin from other vertebrates or fragments thereof, or analogs or variants of these molecules or fragments thereof.

In particular, the proposed truncated VWF fusion constructs of the invention may include naturally occurring polymorphic variants of human albumin and fragments of human albumin. Generally speaking, an albumin fragment or variant will be at least 10, preferably at least 40, most preferably more than 70 amino acids long.

Preferred embodiments of the invention include albumin variants with enhanced binding to the FcRn receptor. Such albumin variants may lead to a longer plasma half-life of a truncated VWF albumin variant fusion protein as compared to a truncated VWF fusion with a wild-type albumin.

The albumin portion of the proposed VWF fusion constructs of the invention may comprise at least one subdomain or domain of HA or conservative modifications thereof.

Immunoglobulins as HLEPs

Immunoglobulin G (IgG) constant regions (Fc) are known in the art to increase the half-life of therapeutic proteins (Dumont J A et al. 2006. BioDrugs 20:151-160). The IgG constant region of the heavy chain consists of 3 domains (CH1-CH3) and a hinge region. The immunoglobulin sequence may be derived from any mammal, or from subclasses IgG1, IgG2, IgG3 or IgG4, respectively. IgG and IgG fragments without an antigen-binding domain may also be used as HLEPs. The therapeutic polypeptide portion is connected to the IgG or the IgG fragments preferably via the hinge region of the antibody or a peptidic linker, which may even be cleavable. Several patents and patent applications describe the fusion of therapeutic proteins to immunoglobulin constant regions to enhance the therapeutic protein's in vivo half-lives. US 2004/0087778 and WO 2005/001025 describe fusion proteins of Fc domains or at least portions of immunoglobulin constant regions with biologically active peptides that increase the half-life of the peptide, which otherwise would be quickly eliminated in vivo. Fc-IFN-β fusion proteins were described that achieved enhanced biological activity, prolonged circulating half-life and greater solubility (WO 2006/000448). Fc-EPO proteins with a prolonged serum half-life and increased in vivo potency were disclosed (WO 2005/063808) as well as Fc fusions with G-CSF (WO 2003/076567), glucagon-like peptide-1 (WO 2005/000892), clotting factors (WO 2004/101740) and interleukin-10 (U.S. Pat. No. 6,403,077), all with half-life enhancing properties.

Various HLEPs which can be used in accordance with this invention are described in detail in WO 2013/120939 A1.

Nucleic Acid

The nucleic acid encoding the polypeptide to be expressed can be prepared according to methods known in the art. Based on the cDNA sequence of VWF (SEQ ID NO:8), recombinant DNA encoding the above-mentioned truncated VWF constructs can be designed and generated.

Even if the glycoprotein which is secreted by the host cells does not comprise amino acids 1 to 763 of VWF, it is preferred that the nucleic acid (e.g. the DNA) encoding the intracellular precursor of the glycoprotein comprises a nucleotide sequence encoding an amino acid sequence having a sequence identity of at least 95%, at least 96%, at least 97%, at least 98%, or at least 99%, to amino acids 23 to 763 or preferably to amino acids 1 to 763 of SEQ ID NO:9. Most preferably, the nucleic acid (e.g. the DNA) encoding the intracellular precursor of the glycoprotein comprises a nucleotide sequence encoding amino acids 23 to 763 of SEQ ID NO:9, or amino acids 1 to 763 of SEQ ID NO:9.

Constructs in which the DNA contains the entire open reading frame inserted in the correct orientation into an expression plasmid may be used for protein expression. Typical expression vectors contain promoters that direct the synthesis of large amounts of mRNA corresponding to the inserted nucleic acid in the plasmid-bearing cells. They may also include an origin of replication sequence allowing for their autonomous replication within the host organism, and sequences that increase the efficiency with which the synthesized mRNA is translated. Stable long-term vectors may be maintained as freely replicating entities by using regulatory elements of, for example, viruses (e.g., the OriP sequences from the Epstein Barr Virus genome). Cell lines may also be produced that have integrated the vector into the genomic DNA, and in this manner the gene product is produced on a continuous basis.

Typically, the cells to be provided are obtained by introducing the nucleic acid encoding a polypeptide comprising the truncated VWF into mammalian host cells.

Host Cells

Any host cell susceptible to cell culture, and to expression of glycoproteins, may be utilized in accordance with the present invention. In certain embodiments, a host cell is mammalian. Non-limiting examples of mammalian cells that may be used in accordance with the present invention include BALB/c mouse myeloma line (NSO/1, ECACC No: 85110503); human retinoblasts (PER.C6 (CruCell, Leiden, The Netherlands)); monkey kidney CV1 line transformed by SV40 (COS-7, ATCC CRL 1651); human embryonic kidney line (293 or 293 cells subcloned for growth in suspension culture, Graham et al., J. Gen Virol., 36:59, 1977); baby hamster kidney cells (BHK, ATCC CCL10); Chinese hamster ovary cells+/−DHFR (CHO, Urlaub and Chasin, Proc. Natl. Acad. Sci. USA, 77:4216, 1980); mouse sertoli cells (TM4, Mather, Biol. Reprod., 23:243 251, 1980); monkey kidney cells (CV1 ATCC CCL 70); African green monkey kidney cells (VERO-76, ATCC CRL-1 587); human cervical carcinoma cells (HeLa, ATCC CCL 2); canine kidney cells (MDCK, ATCC CCL 34); buffalo rat liver cells (BRL 3A, ATCC CRL 1442); human lung cells (W138, ATCC CCL 75); human liver cells (HepG2, HB 8065); mouse mammary tumor (MMT 060562, ATCC CCL51); TRI cells (Mather et al., Annals NY. Acad. Sci., 383:44-68, 1982); MRC 5 cells; PS4 cells; human amniocyte cells (CAP); and a human hepatoma line (Hep G2). Preferably, the cell line is a rodent cell line, especially a hamster cell line such as CHO or BHK.

Methods suitable for introducing nucleic acids sufficient to achieve expression of a glycoprotein of interest into mammalian host cells are known in the art. See, for example, Gething et al., Nature, 293:620-625, 1981; Mantei et al., Nature, 281:40-46, 1979; Levinson et al. EP 117,060; and EP 117,058. For mammalian cells, common methods of introducing genetic material into mammalian cells include the calcium phosphate precipitation method of Graham and van der Erb (Virology, 52:456-457, 1978) or the Lipofectamine™ (Gibco BRL) Method of Hawley-Nelson (Focus 15:73, 1993). General aspects of mammalian cell host system transformations have been described by Axel in US. Pat. No. 4,399,216. For various techniques for introducing genetic material into mammalian cells, see Keown et al., Methods in Enzymology, 1989, Keown et al., Methods in Enzymology, 185:527-537, 1990, and Mansour et al., Nature, 336:348-352, 1988.

Culturing the Cells

In a second step, the method of the first aspect of the invention comprises culturing the cells at a temperature of less than 36.0° C. In the method of the second aspect, the method comprises culturing the cells under conditions that allow expression of the glycoprotein.

The basal medium chosen for culturing the host cell line is not critical to the present invention and may be any one of, or combination of, those known to the art which are suitable for culturing mammalian cells. Media such as Dulbecco's Modified Eagle Medium, Ham's F-12 Medium, Eagle's Minimal Essential Medium and RPMI-1640 Medium and the like are commercially available. The addition of growth factors such as recombinant insulin is optional. In one embodiment, the medium is "protein-free" in the sense that it is either completely free of any protein or at least are free of any protein that is not recombinantly produced. Human serum albumin may be used as a serum-free culture supplement for the production of the glycoprotein. Preferably, the medium contains a protease inhibitor, such as a serine protease inhibitor, which is suitable for tissue culture and which is of synthetic or vegetable origin.

Generally, the present invention may be used with any cell culture method that is amenable to the expression of glycoproteins. For example, cells may be grown in batch or fed-batch cultures, where the culture is terminated after sufficient expression of the glycoprotein, after which the expressed glycoprotein is harvested. Alternatively, cells may be grown in continuous cultures (e.g. perfusion cultures), where the culture is not terminated and new nutrients and other components are periodically or continuously added to the culture, during which the expressed glycoprotein is harvested periodically or continuously. The latter embodiment is preferred if the method comprises a temperature shift as described hereinbelow. The culture can be any conventional type of culture, such as batch, fed-batch or continuous, but is preferably continuous. Suitable continuous cultures include perfusion culture.

Cells may be grown in any convenient volume chosen by the practitioner. For example, cells may be grown in small scale reaction vessels ranging in volume from a few milliliters to several liters. Alternatively, cells may be grown in large scale commercial bioreactors ranging in volume from approximately at least 1 liter to 10, 100, 250, 500, 1000, 2500, 5000, 8000, 10,000, 12,000 liters or more, or any volume in between. The culture is typically carried out in a bioreactor, which is usually a stainless steel, glass or plastic vessel of 1 (one) to 10000 (ten thousand) litres capacity, for example 5, 10, 50, 100, 1000, 2500, 5000 or 8000 litres. The vessel is usually rigid but flexible plastic bags can be used, particularly for smaller volumes. These are generally of the 'single use' type.

Mammalian cells such as CHO and BHK cells are generally cultured as suspension cultures. That is to say, the cells are suspended in the medium, rather than adhering to a solid support. The cells may alternatively be immobilized on a carrier, in particular on a microcarrier. Porous carriers, such as Cytoline®, Cytopore® or Cytodex®, may be particularly suitable.

To obtain a high sialylation, the cells (e.g. CHO cells) are preferably cultured at a decreased temperature, e.g. at less than 36.0° C. "Decreased temperature" refers to a temperature that is lower than the optimum temperature or normal temperature for growth of the respective cell line. For most mammalian cells the normal temperature is 37° C. It is therefore preferred according to the invention that the cells (e.g. CHO cells) are cultured at a decreased temperature of 30.0 to 36.0° C., 30.5 to 35.5° C., 31.0 to 35.0° C., 31.5 to 34.5° C., 32.0 to 34.0° C., or 32.5 to 33.5° C. Preferably, the cells are cultured at a decreased temperature of 30.0° C.±1.0° C., 31.0° C.±1.0° C., 32.0° C.±1.0° C., 33.0° C.±1.0° C., 34.0° C.±1.0° C., or 35.0° C.±1.0° C.

The decreased temperature is maintained for a time period that is sufficient to increase the sialylation of the glycoprotein to be expressed. Preferably, the decreased temperature is maintained for at least 1 hour, at least 6 hours, at least 12 hours, at least 18 hours, at least 24 hours, at least 48 hours, at least 72 hours, at least 96 hours, at least 120 hours, or at least 144 hours. In other embodiments, the decreased temperature is maintained for 1 hour to 8 weeks, 6 hours to 6 weeks, 12 hours to 5 weeks, 18 hours to 4 weeks, 24 hours to 3 weeks, 48 hours to 14 days, 72 hours to 10 days, or 3 to 7 days.

To accomplish this, a culture may be subjected to one or more temperature shifts during the course of the culture. When shifting the temperature of a culture, the temperature shift may be relatively gradual. For example, it may take several hours or days to complete the temperature change. Alternatively, the temperature shift may be relatively abrupt. The temperature may be steadily increased or decreased during the culture process. Alternatively, the temperature may be increased or decreased by discrete amounts at various times during the culture process. The subsequent temperature(s) or temperature range(s) may be lower than or higher than the initial or previous temperature(s) or temperature range(s). One of ordinary skill in the art will understand that multiple discrete temperature shifts are encompassed in this embodiment. For example, the temperature may be shifted once (either to a higher or lower temperature or temperature range), the cells maintained at this temperature or temperature range for a certain period of time, after which the temperature may be shifted again to a new temperature or temperature range, which may be either higher or lower than the temperature or temperature range of the previous temperature or temperature range. The temperature of the culture after each discrete shift may be constant or may be maintained within a certain range of temperatures.

Typically, the cells (e.g. CHO cells) will initially be cultured at a "normal" temperature of 37.0° C.±1.0° C. until the target cell density is achieved. The initial culture period is then followed by a temperature shift to the decreased temperature. After a period of culturing at the decreased temperature, a temperature shift to the normal temperature may or may not follow. Preferably, the cells (e.g. CHO cells) will initially be cultured at 37.0° C.±1.0° C. for several days, followed by manufacturing at a decreased temperature of 31.0-35.0° C.

Based on the present disclosure, those of ordinary skill in the art will be able to select temperatures in which to grow cells, depending on the particular needs of the respective cell line and the particular production requirements of the practitioner.

In certain embodiments, batch and fed-batch bioreactors are terminated once the expressed glycoprotein reaches a sufficiently high titer. Additionally or alternatively, batch and fed-batch bioreactors may be terminated once the cells reach a sufficiently high density, as determined by the needs of the practitioner. For example, the culture may be terminated once the cells reach 1, 5, 10, 15, 20, 25, 30, 35, 40, 45, 50, 55, 60, 65, 70, 75, 80, 85, 90, 95 or 99 percent of maximal viable cell density. Additionally or alternatively, batch and fed-batch bioreactors may be terminated prior to excessive accumulation of metabolic waste products such as lactate and ammonium.

In certain cases, it may be beneficial to supplement a cell culture during the subsequent production phase with nutrients or other medium components that have been depleted or metabolized by the cells. As non-limiting examples, it may be beneficial to supplement a cell culture with hormones and/or other growth factors, inorganic ions (such as, for example, sodium, chloride, calcium, magnesium, and phosphate), buffers, vitamins, nucleosides or nucleotides, trace elements (inorganic compounds usually present at very low final concentrations), amino acids, lipids, or glucose or other energy source. Such supplementary components may all be added to the cell culture at one time, or they may be provided to the cell culture in a series of additions or they may be provided together with fresh medium during a perfusion culture.

Alternatively to batch and fed-batch bioreactors the invention can also be practiced when cells expressing a glycoprotein of the invention are cultured in continuous perfusion bioreactors.

One of ordinary skill in the art will be able to tailor specific cell culture conditions in order to optimize certain characteristics of the cell culture including but not limited to growth rate, cell viability, final cell density of the cell culture, final concentration of detrimental metabolic byproducts such as lactate and ammonium, titer of the expressed glycoprotein, extent and composition of the oligosaccharide side chains or any combination of these or other conditions deemed important by the practitioner.

Isolation of the Expressed Glycoprotein

In general, it will typically be desirable to isolate and/or purify glycoproteins expressed according to the present invention. In certain embodiments, the expressed glycoprotein is secreted into the medium and thus cells and other solids may be removed, as by centrifugation or filtering for example, as a first step in the purification process.

The expressed glycoprotein may be isolated and purified by standard methods including, but not limited to, chromatography (e.g., ion exchange, affinity, size exclusion, and hydroxyapatite chromatography), gel filtration, centrifugation, or differential solubility, ethanol precipitation and/or by any other available technique for the purification of proteins (See, e.g., Scopes, Protein Purification Principles and Practice 2nd Edition, Springer-Verlag, New York, 1987; Higgins, S. J. and Hames, B. D. (eds.), Protein Expression: A Practical Approach, Oxford Univ Press, 1999; and Deutscher, M. P., Simon, M. I., Abelson, J. N. (eds.), Guide to Protein Purification: Methods in Enzymology (Methods in Enzymology Series, Vol. 182), Academic Press, 1997, each of which is incorporated herein by reference). For immunoaffinity chromatography in particular, the glycoprotein may be isolated by binding it to an affinity column comprising antibodies that were raised against that glycoprotein and were affixed to a stationary support. Alternatively, affinity tags such as an influenza coat sequence, poly-histidine, or glutathione-S-transferase can be attached to the glycoprotein by standard recombinant techniques to allow for easy purification by passage over the appropriate affinity column. Protease inhibitors such as phenyl methyl sulfonyl fluoride (PMSF), leupeptin, pepstatin or aprotinin may be added at any or all stages in order to reduce or eliminate degradation of the glycoprotein during the purification process. Protease inhibitors are particularly advantageous when cells must be lysed in order to isolate and purify the expressed glycoprotein. Additionally or alternatively, glycosidase inhibitors may be added at any or all stages in order to reduce or eliminate enzymatic trimming of the covalently attached oligosaccharide chains. A preferred purification method is described in Example 5 of this application.

Glycoproteins expressed according to the present invention have more extensive sialylation than they would if grown under traditional cell culture conditions. Thus, one practical benefit of the present invention that may be exploited at the purification step is that the additional and/or altered sialic acid residues on a glycoprotein grown in accordance with certain of the present inventive methods may confer on it distinct biochemical properties that may be used by the practitioner to purify that glycoprotein more easily, or to a greater purity, than would be possible for a glycoprotein grown in accordance with more traditional methods. For example, the glycoprotein can be purified or greatly enriched by anion exchange chromatography, making use of the negative charge of the sialic acid residues. Thereby a further enrichment of glycoprotein with high sialylation can be achieved.

In a further embodiment, the sialylation of the glycoprotein obtained by a method of the invention can be further increased by contacting the glycoprotein with a sialyltransferase in vitro. The sialyltransferase typically is a mammalian sialyltransferase, preferably it is a human sialyltransferase. The sialyltransferase may be an α-2,3-sialyltransferase and/or an α-2,6-sialyltransferase. Preferably, the sialyltransferase is a human α-2,3-sialyltransferase (Genbank NP_775479-ST3GAL 1) and/or a human α-2,6-sialyltransferase. Most preferably, the sialyltransferase is human α-2,6-sialyltransferase identified by Genbank NP_003023-ST6GAL 1). Further present in the in vitro reaction is a sialyl group donor, or sialic acid donor. Suitable donors include, e.g., Cytidine-5'-monophospho-N-acetylneuraminic acid (CMP-NANA), Roche Catalog No. 05 974 003 103. A suitable kit for in vitro sialylation is available from Roche (Catalog Number 07 012 250 103).

One of ordinary skill in the art will appreciate that the exact purification technique will vary depending on the character of the glycoprotein to be purified, the character of the cells from which the glycoprotein is expressed, and/or the composition of the medium in which the cells were grown.

As mentioned above, the invention, in a second aspect, relates to a method of producing a glycoprotein comprising N-glycans with increased sialylation, which comprises (i) providing cells comprising a nucleic acid encoding a polypeptide comprising a truncated von Willebrand Factor (VWF) and a recombinant nucleic acid encoding an α-2,3-sialyltransferase and/or an α-2,6-sialyltransferase, preferably an α-2,6-sialyltransferase, and (ii) culturing the cells under conditions that allow expression of the glycoprotein.

The α-2,3-sialyltransferase preferably is a human α-2,3-sialyltransferase. The cDNA sequence encoding human α-2,3-sialyltransferase is shown in SEQ ID NO:12, and based thereon the skilled artisan can design suitable expression vectors containing a coding sequence of α-2,3-sialyltransferase.

The α-2,6-sialyltransferase preferably is a human α-2,6-sialyltransferase. The cDNA sequence encoding human α-2,6-sialyltransferase is shown in SEQ ID NO:7, and based thereon the skilled artisan can design suitable expression vectors containing a coding sequence of α-2,6-sialyltransferase.

The transfected cells can be cultured under conditions allowing expression of the glycoprotein according to known culturing methods.

The glycoprotein can be recovered and/or isolated using established purification techniques.

The embodiments described hereinabove in connection with the method of the first aspect of the invention apply to the method of the second aspect mutatis mutandis.

Glycoprotein of the Invention

In a third aspect the invention relates to a glycoprotein obtainable by a method described herein.

In a fourth aspect, the invention relates to a glycoprotein comprising a truncated von Willebrand Factor (VWF), wherein said truncated VWF is capable of binding to a Factor VIII (FVIII), and wherein said glycoprotein comprises N-glycans, and at least 75%, preferably at least 80%, more preferably at least 85% of said N-glycans comprise, on average, at least one sialic acid moiety. In preferred embodiments, at least 87%, at least 90%, at least 92%, at least 93%, at least 94%, at least 95%, at least 96%, at least 97%, at least 98%, or at least 99%, of said N-glycans comprise, on average, at least one sialic acid moiety. The inventors demonstrated that polypeptides comprising highly sialylated VWF fragments not only have a prolonged half-life themselves, but are also capable to extend the half-life of co-administered FVIII. In other words, administration of the glycoprotein of the invention leads to an extended half-life and/or to a reduced clearance of co-administered FVIII.

In a fifth aspect, the invention relates to a glycoprotein comprising a truncated von Willebrand Factor (VWF), wherein said truncated VWF is capable of binding to a Factor VIII (FVIII), and wherein said glycoprotein comprises N-glycans, wherein at least 50% of the sialyl groups of the N-glycans of the glycoproteins are α-2,6-linked sialyl groups. In general, terminal sialyl groups can be attached to the galactose groups via a α-2,3- or via a α-2,6-linkage. In one embodiment, N-glycans of the glycoprotein of the invention comprise more α-2,6-linked sialyl groups than α-2,3-linked sialyl groups. Preferably, at least 60%, or at least 70%, or at least 80%, or at least 90% of the sialyl groups of the N-glycans are α-2,6-linked sialyl groups. These embodiments can be obtained by, e.g., co-expressing human α-2,6-sialyltransferase in mammalian cells.

In a sixth aspect, the invention relates to a glycoprotein comprising a truncated von Willebrand Factor (VWF), wherein said truncated VWF is capable of binding to a Factor VIII (FVIII), and wherein said glycoprotein comprises N-glycans, wherein at least 50% of the sialyl groups of the N-glycans of the glycoproteins are α-2,3-linked sialyl groups. In general, terminal sialyl groups can be attached to the galactose groups via a α-2,3- or via a α-2,6-linkage. In one embodiment, N-glycans of the glycoprotein of the invention comprise more α-2,3-linked sialyl groups than α-2,6-linked sialyl groups. Preferably, at least 60%, or at least 70%, or at least 80%, or at least 90% of the sialyl groups of the N-glycans are α-2,3-linked sialyl groups. These embodiments can be obtained by, e.g., co-expressing human α-2,3-sialyltransferase in mammalian cells.

The preferred amino acid sequences of the glycoprotein of the invention have already been described hereinabove. The embodiments described above in connection with the first aspect of the invention apply to the third, fourth, fifth and sixth aspects mutatis mutandis.

The "glycoprotein of the invention" as used herein refers to a glycoprotein according to the third, fourth, fifth or sixth aspect. The glycoprotein of the invention has an increased sialylation of N-glycans, and in particular an increased α-2,6-sialylation or an increased α-2,3-sialylation.

In one embodiment, at least 75%, at least 80%, at least 85%, at least 90%, or at least 95% of the N-glycans of the glycoprotein of the invention comprise at least one sialic acid group. In another embodiment, at least 75%, at least 80%, at least 85%, at least 90%, at least 95%, at least 96%, at least 97%, at least 98% or at least 99% of the N-glycans of the truncated VWF within the glycoprotein of the invention comprise at least one sialic acid group.

In another embodiment, less than 25%, less than 20%, less than 15%, or less than 12%, or even less than 10%, or less than 8%, or less than 6%, or less than 5%, or less than 4%, or less than 3%, or less than 2% or even less than 1% of the N-glycans of the glycoprotein of the invention are asialo-N-glycans, i.e. they are N-glycans lacking a sialic acid group. In another embodiment, less than 25%, less than 20%, less than 15%, or less than 12%, or less than 10%, or less than 8%, or less than 6%, or less than 5%, or less than 4%, or less than 3%, or less than 2% or even less than 1% of the N-glycans of the truncated VWF within the glycoprotein of the invention are asialo-N-glycans, i.e. they do not have a sialic acid group.

In another embodiment, at least 30%, or at least 35%, or at least 40% of the N-glycans of the glycoprotein of the invention are monosialo-N-glycans, i.e. they are N-glycans with one sialic acid group. In another embodiment, at least 30%, or at least 35%, or at least 40% of the N-glycans of the truncated VWF within the glycoprotein of the invention are monosialo-N-glycans. By way of non-limiting example the amount of monosialylated N-glycans can be determined as detailed in Example 6 and in Example 12.

In yet another embodiment, at least 15%, or at least 25%, or at least 30% of the N-glycans of the glycoprotein of the invention are disialo-N-glycans, i.e. they are N-glycans with 2 sialic acid groups. In yet another embodiment, at least 15%, or at least 25%, or at least 30% of the N-glycans of the truncated VWF within the glycoprotein of the invention are disialo-N-glycans. By way of non-limiting example the amount of disialylated N-glycans can be determined as detailed in Example 6 and in Example 12.

In yet another embodiment, at least 5%, or at least 10%, of the N-glycans of the glycoprotein of the invention are trisialo-N-glycans, i.e. they are N-glycans with 3 sialic acid groups. In yet another embodiment, at least 5%, or at least 10%, of the N-glycans of the truncated VWF within the glycoprotein of the invention are trisialo-N-glycans. By way of non-limiting example the amount of trisialylated N-glycans can be determined as detailed in Example 6 and in Example 12.

In another embodiment, at least 20%, or at least 30%, or at least 40%, of the N-glycans of the glycoprotein of the invention comprise two or more sialic acid groups. In another embodiment, at least 20%, or at least 30%, or at least 40%, of the N-glycans of the truncated VWF within the glycoprotein of the invention comprise two or more sialic acid groups.

Other preferred embodiments of the invention comprise a truncated von Willebrand Factor (VWF), wherein said truncated VWF is capable of binding to a Factor VIII (FVIII), and wherein said glycoprotein comprises N-glycans, wherein less than 35%, preferably less than 34%, preferably less than 33%, preferably less than 32%, preferably less than 31%, preferably less than 30%, preferably less than 29%, preferably less than 28%, preferably less than 27% preferably less than 26%, preferably less than 25%, preferably less than 24%, preferably less than 23%, preferably less than 22%, preferably less than 21%, preferably less than 20%, preferably less than 19%, preferably less than 18%, preferably less than 17%, preferably less than 16%, preferably less than 15%, preferably less than 14%, preferably less than 13%, preferably less than 12%, preferably less than 11%, preferably less than 10%, preferably less than 9%, preferably less than 8%, preferably less than 7%, preferably less than 6% and preferably less than 5% of said N-glycans comprise, on average, two or more terminal and non-sialylated galactose residues.

Still other even more preferred embodiments of the invention comprise a truncated von Willebrand Factor (VWF), wherein said truncated VWF is capable of binding to a Factor VIII (FVIII), and wherein said truncated VWF comprises N-glycans, wherein less than 6%, preferably less than 5%, preferably less than 4%, preferably less than 3%, preferably less than 2%, and preferably less than 1% of said N-glycans comprise, on average, three or more terminal and non-sialylated galactose residues.

The above-described embodiments can be combined with each other. Any percentages of N-glycans mentioned above, or any indications of the degree of sialylation, are to be understood as average percentages or degrees, i.e. they refer to a population of molecules, not to a single molecule. It is clear that the glycosylation or sialylation of the individual glycoprotein molecules within a population of glycoproteins will show some heterogeneity.

It has further been found that the glycoproteins obtained in accordance with this invention have a high proportion of dimers. The glycoprotein of the invention is therefore preferably present as dimer. In one embodiment, at least 50%, or at least 60%, or at least 70%, or at least 80%, or at least 90%, or at least 95% or about 100% of the glycoproteins are present as dimers. In another embodiment, the ratio dimer:monomer of the glycoprotein of the invention is at least 1.5, preferably at least 2, more preferably at least 2.5 or at least 3. The dimer formation obtained by the methods of the invention is favorable, as the dimer has an improved affinity to Factor VIII. The dimer content, and the ratio of dimer to monomer of the glycoprotein of the invention can be determined as described in Example 5.

In another preferred embodiment, the glycoprotein of the invention comprises a heterologous polypeptide, e.g. a HLEP as defined above. Most preferably, the HLEP is human serum albumin (see SEQ ID NO:11). The embodiments described supra apply here mutatis mutandis.

The glycoprotein of the invention is preferably capable of binding to Factor VIII (see above). In one embodiment, the affinity of the glycoprotein of the invention to Factor VIII is greater than that of human native VWF to the same Factor VIII. The factor VIII affinity may refer to human native Factor VIII, or to the Factor VIII characterized by SEQ ID NO:10.

It has been found that preparations of the glycoprotein in accordance with this invention with a high proportion of dimers do have an increased affinity to Factor VIII. Such increased affinity to Factor VIII does lead to an enhanced stabilization of Factor VIII by the glycoproteins of the present invention. Alternatively to or in combination with an increased dimer proportion also glycoproteins in accordance with the invention with mutations within the Factor VIII binding domain which do increase the affinity to Factor VIII are preferred embodiments of the invention. Suitable mutations are disclosed, e.g., in WO 2013/120939 A1.

Another aspect of the invention is a glycoprotein as defined herein for use in the treatment of a blood coagulation disorder. The treatment comprises administering to a patient an effective amount of the glycoprotein. The treatment may further comprise administering a FVIII.

Another aspect of the invention is a pharmaceutical composition comprising a glycoprotein of the invention, and a pharmaceutically acceptable excipient or carrier.

Another aspect of the present invention is a pharmaceutical kit comprising (i) a glycoprotein as defined hereinabove and (ii) a Factor VIII. Preferably, the glycoprotein and the FVIII are contained in separate compositions.

Another aspect of the present invention is a pharmaceutical kit comprising (i) a glycoprotein as defined hereinabove and (ii) a Factor VIII, for simultaneous, separate or sequential use in the treatment of a blood coagulation disorder.

Another aspect of the invention is the use of a polypeptide as defined hereinabove for increasing the terminal half-life or mean residence time (MRT) or reducing the clearance of Factor VIII. For evaluation of the pharmacokinetic data a linear pharmacokinetics model (compound elimination via the central compartment) was applied. Accordingly, any pharmacokinetic parameters used herein are based on a linear pharmacokinetics model (compound elimination via the central compartment), unless indicated otherwise.

The "half-life" T½(t) at a certain time t is the time it takes to halve the plasma concentration C(t) that is present at time t, i.e. C [t+T½(t)]=C(t)/2. The "terminal half-life" is the limit of T½(t) when t tends to infinity. The area under the curve (AUC) can be determined to assess clearance effects. A reduction in clearance leads to higher AUC values, and to an increase in half-life.

The term "MRT", as used herein, means the average time a drug molecule resides in the body. In a linear pharmacokinetic system with constant clearance MRT can be calculated as area under the first moment curve (AUMC) divided by AUC. The first moment curve is time multiplied by plasma concentration at that time.

The MRT of administered FVIII is increased by at least 25%, preferably by at least 50%, more preferably by at least 75%, more preferably by at least 100%, most preferably by at least 125%, if an effective amount of the glycoprotein of the present invention is co-administered, i) relative to administration of the FVIII alone or ii) relative to administration of a reference protein which has the same protein sequence as the glycoprotein of the invention but a completely desialylated N-glycan structure or iii) relative to administration of a reference protein which has the same protein sequence as the glycoprotein of the invention but more than 35% of its N-glycans comprise two or more terminal and non-sialylated N-glycans and more than 6% of its N-glycans comprise three or more terminal and non-sialylated galactose residue.

The MRT of the glycoprotein prepared according to the method of the present invention comprising culturing at a reduced temperature is greater than that of a reference glycoprotein having the same amino acid sequence which was cultured at 37° C. The increase in MRT of the glycoprotein prepared according to the method of the present invention (or of any glycoprotein of the present invention) relative to the reference glycoprotein is preferably at least 25%, more preferably at least 50%, most preferably at least 100%.

The term "clearance", as used herein, refers to the rate at which plasma is cleared of drug. Specifically, it is the current elimination rate of a drug divided by its current plasma concentration. In a linear pharmacokinetic system after a single intravenous administration the clearance can be calculated as the ratio of dose over the area under the plasma concentration-time curve (AUC), provided the clearance is constant. The lower the clearance the longer it takes until the plasma is cleared of the drug.

The clearance of administered FVIII is reduced by at least 10%, preferably by at least 25%, more preferably by at least 40%, more preferably by at least 50%, most preferably by at least 60%, if an effective amount of the glycoprotein of the present invention is co-administered, i) relative to administration of the FVIII alone or ii) relative to administration of a reference protein which has the same protein sequence as the glycoprotein of the invention but a completely desialylated N-glycan structure or iii) relative to administration of a reference protein which has the same protein sequence as the glycoprotein of the invention but more than 35% of its N-glycans comprise two or more terminal and non-sialylated N-glycans and more than 6% of its N-glycans comprise three or more terminal and non-sialylated galactose residue.

The clearance of the glycoprotein prepared according to the method of the present invention comprising culturing at a reduced temperature is lower than that of a reference glycoprotein having the same amino acid sequence which was cultured at 37° C. The reduction in clearance of the glycoprotein prepared according to the method of the present invention (or of any glycoprotein of the present invention) relative to the reference glycoprotein is preferably at least 40%, more preferably at least 50%, most preferably at least 60%.

The invention further relates to a method of increasing the MRT or half-life, or to a method of reducing the clearance of Factor VIII in vivo, comprising administering to a subject an effective amount of a glycoprotein as defined hereinabove.

A further aspect of this invention is a method of treating a blood coagulation disorder, comprising administering to a patient in need thereof an effective amount of a glycoprotein as defined hereinabove.

A further aspect is the use of a glycoprotein as defined hereinabove for reducing the frequency of administration of FVIII in a treatment of hemophilia A. The frequency of intravenous or subcutaneous administration of FVIII may be reduced to twice per week. Alternatively, the frequency of intravenous or subcutaneous administration of FVIII may be reduced to once per week, or even lower, e.g. to once per 10 days or once per 14 days. The FVIII may be administered twice weekly, every 5 days, once weekly, every 10 days, every two weeks, every three weeks, every four weeks or once a month, or in any range between any two of the foregoing values, for example from every four days to every month, from every 10 days to every two weeks, or from two to three times a week, etc.

Another aspect is the use of a glycoprotein as defined hereinabove for reducing the dose of FVIII to be administered in a treatment of hemophilia A.

Treatment of Coagulation Disorder

The glycoproteins of the invention are useful for treating coagulation disorders including hemophilia A. The term "hemophilia A" refers to a deficiency in functional coagulation FVIII, which is usually inherited.

Treatment of a disease encompasses the treatment of patients already diagnosed as having any form of the disease at any clinical stage or manifestation; the delay of the onset or evolution or aggravation or deterioration of the symptoms or signs of the disease; and/or preventing and/or reducing the severity of the disease.

A "subject" or "patient" to whom a glycoprotein of the invention is administered preferably is a human. In certain aspects, the human is a pediatric patient. In other aspects, the human is an adult patient.

Compositions comprising a glycoprotein of the invention and, optionally one or more additional therapeutic agents, such as the second therapeutic agents described below, are described herein. The compositions typically are supplied as part of a sterile, pharmaceutical composition that includes a pharmaceutically acceptable carrier. This composition can be in any suitable form (depending upon the desired method of administering it to a patient).

The glycoproteins of the invention can be administered to a patient by a variety of routes such as orally, transdermally, subcutaneously, intranasally, intravenously, intraperitoneally, intramuscularly, intrathecally, topically or locally. The most suitable route for administration in any given case will depend on the particular glycoprotein, the subject, and the nature and severity of the disease and the physical condition of the subject. Typically, a glycoprotein of the invention will be administered intravenously.

The glycoprotein and the FVIII are preferably administered intravenously or subcutaneously.

In a first embodiment, both the glycoprotein and the FVIII are administered intravenously. In a second embodiment, both the glycoprotein and the FVIII are administered subcutaneously.

In another embodiment, the FVIII is administered intravenously, and the glycoprotein is administered via a different route. In further embodiments, the glycoprotein is administered subcutaneously, and the FVIII is administered via a different route. For example, the glycoprotein may be administered subcutaneously, and the FVIII may be administered intravenously.

In further embodiments, the FVIII is administered subcutaneously, and the glycoprotein is administered via a different route. In further embodiments, the glycoprotein is administered intravenously, and the FVIII is administered via a different route. For example, the glycoprotein may be administered intravenously, and the FVIII may be administered subcutaneously.

The term "Factor VIII" and "FVIII" are used interchangeably herein and encompass both plasma derived FVIII and recombinant FVIII. Recombinant FVIII encompasses without limitation full-length FVIII as well as two-chain B-domain deleted or truncated variants as well as single-chain B-domain deleted or truncated variants for example those described in WO 2004/067566 and other FVIII variants with mutations outside the B-domain but having the biological activity of FVIII.

Determination of the effective dosage, total number of doses, and length of treatment with a glycoprotein of the invention is well within the capabilities of those skilled in the art, and can be determined using a standard dose escalation study.

Pharmaceutical Compositions

Therapeutic formulations of the glycoproteins of the invention suitable in the methods described herein can be prepared for storage as lyophilized formulations or aqueous solutions by mixing the glycoprotein having the desired degree of purity with optional pharmaceutically-acceptable carriers, excipients or stabilizers typically employed in the art (all of which are referred to herein as "carriers"), i.e., buffering agents, stabilizing agents, preservatives, isotonifiers, non-ionic detergents, antioxidants, and other miscellaneous additives. See, Remington's Pharmaceutical Sciences, 16th edition (Osol, ed. 1980). Such additives must be nontoxic to the recipients at the dosages and concentrations employed.

Buffering agents help to maintain the pH in the range which approximates physiological conditions. They can present at concentration ranging from about 2 mM to about 50 mM. Suitable buffering agents include both organic and inorganic acids and salts thereof such as citrate buffers (e.g., monosodium citrate-disodium citrate mixture, citric acid-trisodium citrate mixture, citric acid-monosodium citrate mixture, etc.), succinate buffers (e.g., succinic acid-monosodium succinate mixture, succinic acid-sodium hydroxide mixture, succinic acid-disodium succinate mixture, etc.), tartrate buffers (e.g., tartaric acid-sodium tartrate mixture, tartaric acid-potassium tartrate mixture, tartaric acid-sodium hydroxide mixture, etc.), fumarate buffers (e.g., fumaric acid-monosodium fumarate mixture, fumaric acid-disodium fumarate mixture, monosodium fumarate-disodium fumarate mixture, etc.), gluconate buffers (e.g., gluconic acid-sodium glyconate mixture, gluconic acid-sodium hydroxide mixture, gluconic acid-potassium glyuconate mixture, etc.), oxalate buffer (e.g., oxalic acid-sodium oxalate mixture, oxalic acid-sodium hydroxide mixture, oxalic acid-potassium oxalate mixture, etc), lactate buffers (e.g., lactic acid-sodium lactate mixture, lactic acid-sodium hydroxide mixture, lactic acid-potassium lactate mixture, etc.) and acetate buffers (e.g., acetic acid-sodium acetate mixture, acetic acid-sodium hydroxide mixture, etc.). Additionally, phosphate buffers, histidine buffers and trimethylamine salts such as Tris can be used.

Preservatives can be added to retard microbial growth, and can be added in amounts ranging from 0.2%-1% (w/v). Suitable preservatives include phenol, benzyl alcohol, meta-cresol, methyl paraben, propyl paraben, octadecyldimethylbenzyl ammonium chloride, benzalconium halides (e.g., chloride, bromide, and iodide), hexamethonium chloride, and alkyl parabens such as methyl or propyl paraben, catechol, resorcinol, cyclohexanol, and 3-pentanol. Isotonicifiers sometimes known as "stabilizers" can be added to ensure isotonicity of liquid compositions and include polyhydric sugar alcohols, preferably trihydric or higher sugar alcohols, such as glycerin, erythritol, arabitol, xylitol, sorbitol and mannitol. Stabilizers refer to a broad category of excipients which can range in function from a bulking agent to an additive which solubilizes the therapeutic agent or helps to prevent denaturation or adherence to the container wall. Typical stabilizers can be polyhydric sugar alcohols (enumerated above); amino acids such as arginine, lysine, glycine, glutamine, asparagine, histidine, alanine, ornithine, L-leucine, 2-phenylalanine, glutamic acid, threonine, etc., organic sugars or sugar alcohols, such as lactose, trehalose, stachyose, mannitol, sorbitol, xylitol, ribitol, myoinisitol, galactitol, glycerol and the like, including cyclitols such as inositol; polyethylene glycol; amino acid polymers; sulfur containing reducing agents, such as urea, glutathione, thioctic acid, sodium thioglycolate, thioglycerol, α-monothioglycerol and sodium thio sulfate; low molecular weight polypeptides (e.g., peptides of 10 residues or fewer); proteins such as human serum albumin, bovine serum albumin, gelatin or immunoglobulins; hydrophylic polymers, such as polyvinylpyrrolidone monosaccharides, such as xylose, mannose, fructose, glucose; disaccharides such as lactose, maltose, sucrose and trisaccacharides such as raffinose; and polysaccharides such as dextran. Stabilizers can be present in the range from 0.1 to 10,000 weights per part of weight active protein.

Non-ionic surfactants or detergents (also known as "wetting agents") can be added to help solubilize the therapeutic agent as well as to protect the therapeutic protein against agitation-induced aggregation, which also permits the formulation to be exposed to shear surface stressed without causing denaturation of the protein. Suitable non-ionic surfactants include polysorbates (20, 80, etc.), polyoxamers (184, 188 etc.), Pluronic polyols, polyoxyethylene sorbitan monoethers (TWEEN®-20, TWEEN®-80, etc.). Non-ionic surfactants can be present in a range of about 0.05 mg/ml to about 1.0 mg/ml, or in a range of about 0.07 mg/ml to about 0.2 mg/ml.

Additional miscellaneous excipients include bulking agents (e.g., starch), chelating agents (e.g., EDTA), antioxidants (e.g., ascorbic acid, methionine, vitamin E), and cosolvents.

The formulation herein can also contain a second therapeutic agent in addition to a glycoprotein of the invention. Examples of suitable second therapeutic agents are provided below.

The dosing schedule can vary from once a month to daily depending on a number of clinical factors, including the type of disease, severity of disease, and the patient's sensitivity to the glycoprotein of the invention. In specific embodiments, a glycoprotein of the invention is administered, twice weekly, every 5 days, once weekly, every 10 days, every two weeks, every three weeks, every four weeks or once a month, or in any range between any two of the foregoing values, for example from every four weeks to every month, from every 10 days to every two weeks, or from two to three times a week, etc.

The dosage of a glycoprotein of the invention to be administered will vary according to the particular glycoprotein, the subject, and the nature and severity of the disease, the physical condition of the subject, the therapeutic regimen (e.g., whether a second therapeutic agent is used), and the selected route of administration; the appropriate dosage can be readily determined by a person skilled in the art.

It will be recognized by one of skill in the art that the optimal quantity and spacing of individual dosages of a glycoprotein of the invention will be determined by the nature and extent of the condition being treated, the form, route and site of administration, and the age and condition of the particular subject being treated, and that a physician will ultimately determine appropriate dosages to be used. This dosage can be repeated as often as appropriate. If side effects develop the amount and/or frequency of the dosage can be altered or reduced, in accordance with normal clinical practice.

Combination Therapy

Preferably, the patient being treated with the glycoprotein of the invention is also treated with a conventional therapy of coagulation disorders. For example, a patient suffering from hemophilia is typically also being treated with Factor VIII.

In accordance with this invention, the patient being treated with the glycoprotein of the invention is also treated with Factor VIII. The glycoprotein of the invention and the Factor VIII molecule may be administered simultaneously or in a sequential fashion, both modes of administration being encompassed by the term "combination therapy" and "co-administration". The glycoprotein of the invention and the Factor VIII molecule may be administered as a mixture, i.e. within the same composition, or separately, i.e. as separate compositions.

The concentration of Factor VIII in the composition used according to the present invention is typically in the range of 10-10,000 IU/mL. In different embodiments, the concentration of FVIII in the compositions of the invention is in the range of 10-8,000 IU/mL, or 10-5,000 IU/mL, or 20-3,000 IU/mL, or 50-1,500 IU/mL, or 3,000 IU/mL, or 2,500 IU/mL, or 2,000 IU/mL, or 1,500 IU/mL, or 1,200 IU/mL, or 1,000 IU/mL, or 800 IU/mL, or 750 IU/mL, or 600 IU/mL, or 500 IU/mL, or 400 IU/mL, or 300 IU/mL, or 250 IU/mL, or 200 IU/mL, or 150 IU/mL, or 125 IU/mL, or 100 IU/mL, or 62.5 IU/mL, or 50 IU/mL.

"International Unit," or "IU," is a unit of measurement of the blood coagulation activity (potency) of FVIII as measured by a FVIII activity assay such as a one stage clotting assay or a chromogenic substrate FVIII activity assay using a standard calibrated against an international standard preparation calibrated in "IU". One stage clotting assays are known to the art, such as that described in N Lee, Martin L, et al., An Effect of Predilution on Potency Assays of FVIII Concentrates, Thrombosis Research (Pergamon Press Ltd.) 30, 511 519 (1983). Principle of the one stage assay: The test is executed as a modified version of the activated Partial Thromboplastin Time (aPTT)-assay: Incubation of plasma with phospholipids and a surface activator leads to the activation of factors of the intrinsic coagulation system. Addition of calcium ions triggers the coagulation cascade. The time to formation of a measurable fibrin clot is determined. The assay is executed in the presence of Factor VIII deficient plasma. The coagulation capability of the deficient plasma is restored by Coagulation Factor VIII included in the sample to be tested. The shortening of coagulation time is proportional to the amount of Factor VIII present in the sample. The activity of Coagulation Factor VIII is quantified by direct comparison to a standard preparation with a known activity of Factor VIII in International Units.

Another standard assay is a chromogenic substrate assay. Chromogenic substrate assays may be purchased commercially, such as the coamatic FVIII test kit (Chromogenix- Instrumentation Laboratory SpA V. le Monza 338-20128 Milano, Italy). Principle of the chromogenic assay: In the presence of calcium and phospholipid, Factor X is activated by Factor IXa to Factor Xa. This reaction is stimulated by Factor VIIIa as cofactor. FVIIIa is formed by low amounts of thrombin in the reaction mixture from FVIII in the sample to be measured. When using the optimum concentrations of Ca2+, phospholipid and Factor IXa and an excess quantity of Factor X, activation of Factor X is proportional to the potency of Factor VIII. Activated Factor X releases the chromophore pNA from the chromogenic substrate S-2765. The release of pNA, measured at 405 nm, is therefore proportional to the amount of FXa formed, and, therefore, also to the Factor VIII activity of the sample.

The nucleotide and amino acid sequences shown in the sequence listing are summarized in the following table:

TABLE 1

| SEQ ID NO: | Remarks |
|---|---|
| 1 | DNA sequence encoding a polypeptide comprising amino acids 1 to 1242 of human VWF, a glycine/serine linker and human albumin; nucleotide positions (nt): nt 1-6: EcoRI restriction enzyme cleavage site nt 32-3757: coding sequence for VWF amino acids 1 to 1242 nt 3758-3850: coding sequence for glycine/serine linker nt 3851-5608: coding sequence for human albumin nt 5609-5616: NotI restriction enzyme cleavage site |
| 2 | Amino acid sequence encoded by SEQ ID NO: 1 (mature form): amino acid positions (aa): aa 1-479: VWF D'D3-FP region (VWF amino acids 764-1242) aa 480-510: glycine/serine linker aa 511-1195: human albumin |
| 3 | PCR primer α-2,6 sialyltransferase |
| 4 | PCR primer α-2,6 sialyltransferase |
| 5 | nested PCR primer α-2,6 sialyltransferase |
| 6 | nested PCR primer β-2,6 sialyltransferase |
| 7 | cDNA sequence encoding human α-2,6 sialyltransferase |
| 8 | DNA sequence encoding the pre-pro form of human native VWF |
| 9 | Amino acid sequence encoded by SEQ ID NO: 8 |
| 10 | Amino acid sequence of a single chain Factor VIII molecule |
| 11 | Amino acid sequence of mature human serum albumin |
| 12 | cDNA sequence encoding human α-2,3 sialyltransferase |

The following examples illustrate the invention but should not be construed as limiting the present invention to the specific embodiments described herein below.

EXAMPLE 1

Generation of D'D3 Albumin Fusion Protein (D'D3-FP)

The expression cassette for D'D3-FP consisting of cDNA encoding VWF amino acids 1 to 1242, a glycine/serine linker and the cDNA of human albumin was prepared by custom gene synthesis (Eurofins Genomics, Ebersberg, Germany). Through flanking restriction sites (EcoRI, NotI) the expression cassette was excised from the cloning vector supplied and inserted into a pIRESneo3 vector (BD Biosciences, Franklin Lakes, N.J., USA) linearized with EcoRI and NotI. The resulting expression plasmid contained nucleotide sequences encoding the VWF propeptide, D' and D3 (VWF amino acids 1 to 1242 of SEQ ID NO:9) fused to the albumin coding sequence through a short linker coding sequence under CMV promoter control. The nucleotide sequence of the coding sequence is displayed as SEQ ID NO:1, the amino acid sequence of the mature D'D3-FP is shown as SEQ ID NO:2.

EXAMPLE 2

Transfection of Plasmids and Stable Expression of D'D3-FP Dimer in Chinese Hamster Ovary (CHO) Cells The expression plasmid as described above was grown up in XL10 Gold (Agilent Technologies) and purified using standard protocols (Qiagen, Hilden, Germany).

CHO K1 cells were transfected using the Lipofectamine 2000 reagent (Invitrogen) and grown up in serum-free medium (CD-CHO, Invitrogen) in the presence of 500-1000 μg/ml Geneticin. An expression plasmid encoding PACE/furin (pFu-797) as described in WO2007/144173 was cotransfected to maximize propeptide cleavage efficacy. Single cell derived clones were grown up and selected according to their D'D3-FP expression yield as quantified by an albumin specific enzyme immunoassay (see below). The cell line finally selected for D'D3-FP fermentation was called T2050-CL3.

EXAMPLE 3

Coexpression of an α-2,6 Sialyl Transferase

During a cell line generation process as described in example 2 a plasmid carrying an expression unit encoding an α-2,6 sialyl transferase to support the attachment of non-rodent sialic acids can be cotransfected.

The coding sequence for human α-2,6 sialyl transferase is amplified from a human liver cDNA library (Ambion) using primers We2556 (SEQ-ID NO. 3) and We 2558 (SEQ-ID NO. 4) for a first and primers We2553 (SEQ-ID NO. 5) and We 2559 (SEQ-ID NO. 6) for a second PCR in a nested PCR setup. For the first PCR 2 μL of the Ambion human liver cDNA library are mixed with 34.5 μL of water, 10 μl 5× PCR buffer Phusion GC (New England Biolabs), 1 μl of 10 mM dNTPs, 1 μL of We2556 (10 pmol), 1 μl of We2558 (10 pmol) and 0.5 μL of Phusion DNA polymerase (New England Biolabs) and amplified using a touchdown protocol of initial 60 seconds at 98° C., 15 cycles of a) 15 seconds of denaturation at 98° C., b) 30 seconds of annealing at 64° C. and c) 2 minutes of elongation at 72° C., wherein the temperature of the annealing step is reduced by 0.3° C. per cycle, followed by 25 cycles of a) 25 seconds of denaturation at 98° C., b) 30 seconds of annealing at 62° C. and c) 2 minutes of elongation at 72° C., followed by a final extension step for 10 minutes at 72° C., after which the reaction is stopped by cooling down and holding at 4° C. For the nested PCR 2 μL of the first PCR reaction are mixed with 34.5 μL of water, 10 μl 5× PCR buffer Phusion GC, 1 μl of 10 mM dNTPs, 1 μL of We2553 (10 pmol), 1 μl of We2559 (10 pmol) and 0.5 μL of Phusion DNA polymerase and amplified using the touchdown protocol as described for the first PCR. The nested PCR adds an NheI restriction enzyme cutting site to the 5'-end and a BamH1 site to the 3'-end of the PCR fragment. This fragment is cut by NheI and BamH1 and ligated into expression vector pIRESneo3 which had been opened by the same enzymes. The resulting expression vector then can be used for cotransfection.

EXAMPLE 4

Production of D'D3-FP in Bioreactors

The fermentation process for the production of D'D3-FP started with the thaw of cell line T2050-CL3 followed by cell expansion in shake flasks and finally a fermentation process in perfusion mode using the Sartorius BioStat B-DCU 5 L bioreactor and the BioStat STR 50 L single-use bioreactors. The BioSeps 10 L or 200 L (Applikon), respectively, were used as cell retention devices. Cell culture media were either PowerCHO3 (Lonza BESP1204) with 8 mM L-glutamine and 1 µM $CuSO_4$ or ProCHO5 (Lonza BESP1072) with 10 mM L-glutamine and 1 µM $CuSO_4$.

The seed trains in shake flasks were performed at 37° C., 7.5% $CO_2$ at a shaker speed of 160 rpm.

The 5 L bioreactor was inoculated with a target VCD of $2.5 \times 10^5$ cells/mL. The cells were cultivated in PowerCHO3 with 8 mM L-glutamine and 1 µM $CuSO_4$ at a temperature of +37.0° C., a pH of 7.00, and at 30% oxygen saturation. A temperature shift to +34.0° C. (evaluated range +31° C. to +35° C.) was performed after initial harvests from the bioreactor run at +37° C. had been taken. The pH was controlled using $CO_2$ sparged as acid and $NaHCO_3$ as base. The overlay air flow rate was set to 0.5 L/min. A ring sparger was used as a sparging unit. The agitation rate was 150 rpm with a 2fold pitch blade impeller in down pull mode.

The 50 L bioreactor was inoculated with a target VCD of $3.0 \times 10^5$ cells/mL. The cells were cultivated in ProCHO5 medium with 10 mM L-glutamine and 1 µM $CuSO_4$ at a temperature of +37.0° C., a pH of 6.90, and at 30% oxygen saturation. A temperature shift to +34.0° C. was performed after the initial one or two harvests. PH control as above, the overlay air flow rate was set to 2 L/min. A micro sparger was used as a sparging unit. The agitation rate was 90 rpm with a 2fold pitch blade impeller in down pull mode.

The perfusion was initiated when the VCD in the bioreactor was $\geq 1.0 \times 10^6$ cells/mL. The perfusion rate was set to 1.0 volume/volume/day. The BioSep was operated in back flush mode with 5 (10) minutes runtime and 10 seconds back flush at a power input of 7 (30) W (numbers in brackets refer to the 50 L bioreactor). The perfusate and the bleed were filtered inline and collected in bags over 48 hours at +2 to +8° C. The VCD was controlled by active bleeding using a turbidity probe using glucose consumption as parameter with a target of 2 g/L glucose. Harvest and bleed were filtered inline, the harvest system consisting of a disposable filter and disposable bag was changed every second day.

To prepare material for the PK analyses described below harvests taken before and after the respective temperature shifts were purified by affinity and size exclusion chromatography.

EXAMPLE 5

Purification of D'D3-FP Dimer using Affinity Chromatography and Size Exclusion Chromatography The cell-free harvest from the bioreactor was concentrated 30-fold using a TFF system (e.g. Pall Centramate 500 S) with a 30 kD membrane (e.g Pall Centramate OS030T12). That concentrate was spiked with NaCl and EDTA to a final concentration of 0.75 M NaCl and 5 mM EDTA and loaded overnight on a CaptureSelect Human Albumin column (Life Technologies) which was pre-equilibrated with 20 mM Tris buffer pH 7.4. After washing the column with equilibration buffer D'D3-FP was eluted with elution buffer (20 mM Tris, 2 M $MgCl_2$, pH 7.4). The eluate was then 10-fold concentrated and dialyzed against 50 mM Tris, 150 mM NaCl, pH 7.4 using Ultra Centrifugal Filters with a 30 kD cut-off (e.g. Amicon. UFC903024). To separate the D'D3-FP dimer from the monomer portion that material was loaded on a Superdex 200 pg column (GE Healthcare Code: 17-1069-01) pre-equilibrated with 50 mM Tris, 150 mM NaCl, pH 7.4 and the peak fractions containing the D'D3-FP dimer were pooled. The area under the curve for the dimer and monomer peak fractions were used to calculate dimer to monomer ratio.

EXAMPLE 6

Total Sialylation Assay

Materials and Methods:

Acetic acid was from Sigma-Aldrich (Prod. 338826). Acetonitrile was from Burdick and Jackson (Prod. LC015). 2-aminobenzamide (2-AB) was from Aldrich (Prod. A89804). Ammonium hydroxide was from Sigma-Aldrich (Prod. 338818). Ammonium bicarbonate was from Fluka (Prod. 09830). Dimethyl sulfoxide was from Sigma Prod. (D2650). Dithiothreitol (DTT) was from Sigma (Prod. 646563). Formic acid was from Thermo (Prod. 28905). N-Glycosidase F (PNGase 250U) was from Roche (Prod. 11 365 193 00). Sodium cyanoborohydride was from Aldrich (Prod. 156159). Oasis HLB 3cc 60 mg SPE cartridges were from Waters (Part No: WAT094226). 50 KDa Amicon Ultra 4 centrifugal ultrafilters were from Millipore (Cat. No. UFC805008). Zeba Spin 7K MWCO columns 2 mL were from Thermo (No. 89889)

PNGase F Enzymatic Glycan Release:

About 700 µg of D'D3-FP was reduced with DTT in approximately 70 mM ammonium bicarbonate, pH 8.5 at 60° C. for 30 min. The reduced sample was cooled to room temperature and alkylated with iodoacetamide at RT in the dark for 30 min. The alkylated sample was buffer exchanged into 50 mM ammonium bicarbonate pH 8.6 using a 2 mL Zeba Spin 7K MWCO column. To the buffer exchanged sample, 40 U of PNGase was added and the sample incubated at 37° C. for 14 hours. An additional 40 U of PNGase was added and the sample incubated for a further 6 hours at 37° C. The PNGase digested sample was centrifuged through a 50 KDa Amicon Ultra 4 ultrafilter. The filtrate was dried in a CentriVap.

2-AB Labelling of Released N-Glycans:

To prepare the 2-AB labelling reagent, 23 mg of 2-aminobenzamide was dissolved in 350 µL of DMSO and 150 µL glacial acetic acid was added. The resulting solution was added to 32 mg of sodium cyanoborohydride and mixed thoroughly until dissolved.

50 µL of the 2-AB reagent was added to the dried sample and incubated in the dark at 65° C. for 3.5 hours.

A Waters Oasis HLB 3cc 60 mg SPE cartridge was conditioned with 3 mL 95% acetonitrile the 3 mL 35% acetonitrile then 3 mL 95% acetonitrile. The 2-AB labelled sample was diluted by adding 1.95 mL of 95% v/v acetonitrile and immediately loaded onto the HLB cartridge and allowed to drain under gravity. Sample was washed under gravity with 3×3 mL of 95% v/v acetonitrile and the eluted with 3 mL of 35% v/v acetonitrile. The eluate was dried in a Centrivap. The dried 2-AB derivatised sample was dissolved by the addition of 35 µL of Milli Q water and vortex mixing. After dissolution, 85 µL of Acetonitrile was added and mixed briefly. Sample was transferred to a HPLC vial for analysis.

2-AB Glycan Analysis:

High performance liquid chromatography was performed on a Thermo Dionex Ultimate 3000 system consisting of an RS Binary Pump, Autosampler, RS Column Compartment and RS Fluorescence detector. The separation of 2-AB glycan derivatives was achieved using a Dionex GlycanPac AXH-1, 1.9 µm, 2.1×150 mm column (P/N 082472). Mobile phase A consisted of 100% acetonitrile, Mobile phase B consisted of 50 mM Formic acid adjusted to pH 4.0 with 5M ammonium hydroxide solution. The column was maintained at 50° C. and the flow rate was 0.200 mL/min. The column was equilibrated with 15% B. After injection of 6 µL of sample, the mobile phase composition was changed linearly to 40% B over 50 minutes, then to 80% B over 10 minutes, then to 95% B over 0.1 minutes, then maintained at 95% B for 4.9 minutes, and then back to 15% B over 0.1 minutes. The column was requilibrated at 15% B for 14.9 minutes. Fluorescence detection was performed with an excitation wavelength of 320 nm and an emission wavelength of 420 nm.

Results:

TABLE 2

Lots of D'D3-FP provided for PK analysis:

| Lot # | Asialo [%] | Mono-sialo [%] | Di-sialo [%] | Tri-sialo [%] | Tetra-sialo [%] | Sialylation [%] |
|---|---|---|---|---|---|---|
| B-140526 (no temperature shift) | 59.4 | 29.0 | 9.7 | 1.9 | n.d. | 40.6 |
| B-140616KS | 16.4 | 34.6 | 28.1 | 15.3 | 5.6 | 83.6 |
| B-140825 | 12.7 | 42.9 | 32.0 | 9.9 | 2.6 | 87.3 |
| B-140623KS | 10.2 | 38.7 | 33.8 | 14.2 | 3.0 | 89.8 |

D'D3-FP protein purified from harvests taken after the temperature shift from 37° C. to 33° C. (e.g. Lot B-140825) or to 34° C. (e.g. Lot B-140623KS) showed an improved sialylation pattern in that a reduced amount of asialo and monosialo structures was detected while in particular the Di-sialo and Tri-sialo structures increased. The reduced content of asialo structures had a positive effect on the half-life of the D'D3-FP protein itself as well as on a co-administered FVIII (see example 8).

A further beneficial effect was found as a result of the temperature shift in that the ratio of D'D3-FP dimers increased over the monomer at lower temperatures, wherein the dimer is the preferred structure due to its increased binding to FVIII.

TABLE 3

Effect of Temperature on Dimer Content

| Bioreactor temperature before harvest | % Dimer | % Monomer | Ratio Dimer:Monomer |
|---|---|---|---|
| 37 | 52.3 | 47.7 | 1.1 |
| 35 | 71.0 | 29.0 | 2.45 |
| 33 | 71.2 | 28.8 | 2.5 |
| 32 | 74.6 | 25.4 | 2.94 |
| 31 | 77.5 | 22.5 | 3.44 |

As shown in Table 4 the beneficial effect of a temperature shift on the degree of sialylation was not observed with respect to full length VWF. Specifically, the content of asialostructures could not be reduced when full length wild-type VWF albumin fusion ("rVWF-FP") was expressed under similar bioreactor conditions to those described in example 4 and when the temperature was reduced to 33.5° C. compared to the expression at the standard temperature of 37° C. Purification had been performed as described in US 2014/0072561 A1.

TABLE 4

Sialylation of full length VWF

| Lot # | Sialylation |
|---|---|
| rVWF-FP only expressed at 37° C. | 100 |
| rVWF-FP first expressed at 37° C. then at 33.5° C. | 91% of the sialylation degree of rVWF-FP above which was only expressed at 37° C. |

The degree of sialylation of the Lot harvested at 37° C. was normalised to a nominal value of 100. The degree of sialylation determined for the Lot harvested at 33.5° C. was lower than that of the Lot harvested at 37° C.

EXAMPLE 7

Determination of D'D3-FP Antigen Concentration

Human albumin was determined by an ELISA whose performance is known to those skilled in the art. Briefly, microplates were incubated with 100 µL per well of the capture antibody (goat anti-human-albumin-IgG, Cat. No. A80-129A, Bethyl Laboratories, Inc.), diluted to 2 µg/mL in Buffer A [Sigma C3041] for 16 hours at ambient temperature. After washing plates three times with buffer B (Sigma P3563), microplates were blocked with 200 µL per well of blocking solution (Cat. No. 110500, Candor Biosience GmbH), for 1.5 hours at ambient temperature. After washing plates again three times with buffer B (Sigma P3563), serial dilutions of the test sample in LowCross Buffer (Cat. No. 100500, Candor Biosience GmbH,) as well as serial dilutions of N Protein Standard SL (OQIM13, Siemens Healthcare 50-0.78 ng/mL) in LowCross Buffer (volumes per well: 100 µL) were incubated for one hour at +37° C. After four wash steps with buffer B, 100 µL of a 1:40,000 dilution in blocking solution of the detection antibody (goat-anti-Human Albumin-IgG peroxidase labelled, Cat. No. A80-129P, Bethyl Laboratories, Inc.)-D, were added to each well and incubated for 45 min. at +37° C. After three wash steps with buffer B, 100 µL of substrate solution (1:10 (v/v) TMB OUVF:TMB Buffer OUVG, Siemens Healthcare) were added per well and incubated for 20 minutes at ambient temperature in the dark. Addition of 100 µL stop solution (OSFA, Siemens Healthcare) prepared the samples for reading in a suitable microplate reader at 450 nm wavelength. Concentrations of test samples were then calculated using the standard curve with the N Protein Standard SL as reference.

EXAMPLE 8

PK Analysis

Aim

We aimed at characterizing the impact of sialylation on pharmacokinetics (PK) of the half-life extended von Willebrand Factor (VWF) fragment D'D3-FP dimer and FVIII. One aim of these studies was to determine the influence of sialylation of the D'D3-FP dimer on its PK and additionally on the PK of co-administered FVIII in rats (example 8.1). A second example covers the effect on a full-length FVIII product Advate® in rats (example 8.2). The lot # (see Table 2 above) and the degree of D'D3-FP dimer sialylation in % are indicated for each preparation.

EXAMPLE 8.1

Prolongation of Pharmacokinetics of FVIII by Co-Administration of Highly Sialylated D'D3-FP Dimer in Rats Material and Methods Animals: Female Crl:CD (Sprague Dawley) rats in a weight range of 230-300 g were breed at Charles River Laboratories (Sulzfeld, Germany). In house, the animals were kept at standard housing conditions, i.e. at 21-22° C. under a 12 h/12 h light-darkness cycle. Animals were fed ad libitum with standard rat diet (Ssniff-Versuchsdiäten, Soest, Germany). Tap water was supplied ad libitum. Animal husbandry and study procedures complied with the German Animal Welfare law and European Union regulations.

Laboratory evaluations: The test articles were administered i.v. by a single injection into the lateral tail vein at a volume of 3 mL/kg. All D'D3-FP dimer preparations were administered at a dose level of 1000 µg/kg based on human albumin values, and co-administered with 200 IU/kg rVIII-SingleChain (rVIII-SC, chromogenic activity) after incubating for approximately 30 minutes at +37° C. Animals receiving only rVIII-SC served as control (Table 5).

Blood samples were taken retro-orbitally under short term anaesthesia at 5 min, 2, 4, 8, 24, 32, 48 and 72 h after intravenous bolus injection using an alternating sampling scheme. The PK profile was taken from two cohorts of rats per group (n=3 per time-point, n=6 per group). Blood samples were anticoagulated using sodium citrate (2 parts sodium citrate 3.13%+8 parts blood), processed to plasma and stored at −20° C. for the determination of FVIII antigen and/or albumin.

D'D3-FP dimer exposure was determined by measurement of the albumin part of the protein using an immunoassay specific for human albumin (example 7), and FVIII:Ag plasma levels were detected with the FVIII Asserachrom ELISA test kit from Stago, S.A.S., France.

TABLE 5

Treatment groups

| Treatment* | Sialylation [%] of D'D3-FP | D'D3-FP dimer dose [mg albumin/kg] | FVIII dose [IU FVIII: C/kg] |
|---|---|---|---|
| rVIII-SC | — | — | 200 |
| D'D3-FP dimer (B-140526) & rVIII-SC | 40.6 | 1 | 200 |
| D'D3-FP dimer (B-140616KS) & rVIII-SC | 83.6 | 1 | 200 |
| D'D3-FP dimer (B-140623KS) & rVIII-SC | 89.8 | 1 | 200 |

FVIII: C = chromogenic FVIII activity
*Lot # given in brackets

Results

D'D3-FP dimer was quantified via its albumin component, and measurements were performed up to 72 h p.a., and all measured data were well above the detection limit of the assay. Mean residence time (MRT) and clearance (CL) were estimated by non-compartmental methods and the data are presented in FIG. 1. rVIII-SC co-administered with the D'D3-FP dimer with 40.6% sialylation (B-140526) had a shorter MRT and higher clearance as when co-administered with the D'D3-FP dimer preparations with 83.6% and 89.8% sialylation (B-140616KS and B-140623KS, respectively).

Figure 2:
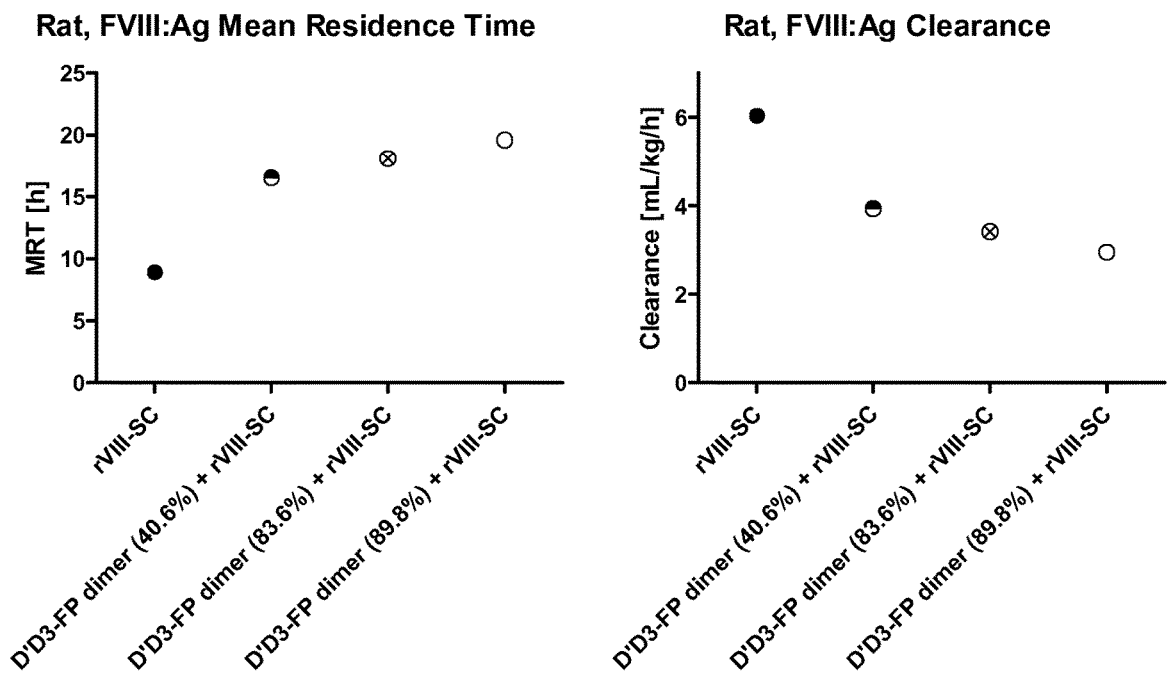
FIG. 2: Mean residence time and clearance (mean) of rVIII-SC quantified as FVIII antigen in rats, as determined in Example 8.1.

In line with this observation, the pharmacokinetic profile of the co-administered FVIII (200 IU/kg chromogenic FVIII activity), quantified as FVIII:Ag via ELISA, was modified accordingly. It shall be mentioned that not all plasma levels at 48 h and 72 h could be measured, some values were below the detection limit of 57 mIU/mL. Clearly, rVIII-SC alone had the shortest MRT and highest clearance, which was generally prolonged when D'D3-FP dimer was co-administered (FIG. 2). Those D'D3-FP dimers, which had a longer exposure by themselves, also prolonged the FVIII PK profile. Thus, MRT of the D'D3-FP dimer with 40.6% sialylation (B-140526) was shorter and clearance was higher compared to D'D3-FP dimer with sialylation >80%.

Thus, the pharmacokinetic profile of FVIII:Ag was dependent on the sialylation of D'D3-FP dimer, i.e., shortest PK was observed with 40.6% sialylation and longest PK with those of >80% sialylation.

Evaluation of PK characteristics of D'D3-FP dimer was done in more detail, i.e. additionally calculating maximal concentrations ($C_{max}$) and terminal half-life (t½) in a non-compartmental model, as well as calculating the x-fold increases (Table 6).

Sialylation between 89.8% and 40.6% influenced clearance of D'D3-FP dimer by more than 2-fold (0.91 mL/kg/h for the 89.8% D'D3-FP dimer and 2.06 mL/kg/h for the 40.6% D'D3-FP dimer as determined by measuring the albumin concentration over time). This relates to more than 40% increase in mean residence time (MRT, i.e. 56.9 h to 81.5 h) and more than 30% increase in terminal half-life (i.e. 44.0 h to 58.6 h).

As depicted in the graphs for MRT and clearance, this translates to the PK characteristics of the co-administered FVIII, even though not as obvious as for D'D3-FP dimer (Table 6, FVIII:Ag): clearance is decreased by more than 30% (3.93 mL/kg/h to 2.95 mL/kg/h), MRT is increased by 19% (16.5 h to 19.6 h) and terminal half-life by 15% (11.4 h to 13.1 h).

Therewith, the increase in exposure over time is given by D'D3-FP dimer depending on the percentage of sialylation, as may also be seen by the fold increase of PK characteristics of rVIII-SC given alone. While 40.6% sialylation prolong FVIII PK 1.5-1.9fold, an optimized D'D3-FP dimer with 89.8% sialylation prolongs FVIII PK 2.0-2.2fold, and 83.6% sialylation leads to intermediate values. Thus, this effect correlates with the degree of sialylation within the investigated range from 40.6% to 89.8%.

TABLE 6

Pharmacokinetic parameters of D'D3-FP dimer and FVIII: Ag after co-administration of rVIII-SC and D'D3-FP dimer in rats (non-compartmental analysis)
Dose D'D3-FP dimer 1 mg/kg, dose rVIII-SC 200 IU/kg

| Treatment* | $C_{max}$, extrap. IU/mL | Clearance mL/kg/h | MRT h | Half-life, terminal h |
|---|---|---|---|---|
| Albumin | | | | |
| D'D3-FP dimer (40.6%) & rVIII-SC | 18.1 | 2.06 | 56.9 | 44.0 |
| D'D3-FP dimer (83.6%) & rVIII-SC | 18.8 | 1.07 | 82.4 | 61.4 |
| D'D3-FP dimer (89.8%) & rVIII-SC | 21.3 | 0.91 | 81.5 | 58.6 |
| FVII: Ag | | | | |
| rVIII-SC | 4.26 | 6.04 | 8.9 | 6.4 |
| D'D3-FP dimer | 3.05 | 3.93 | 16.5 | 11.4 |

TABLE 6-continued

Pharmacokinetic parameters of D'D3-FP dimer and
FVIII: Ag after co-administration of rVIII-SC and
D'D3-FP dimer in rats (non-compartmental analysis)
Dose D'D3-FP dimer 1 mg/kg, dose rVIII-SC 200 IU/kg

| Treatment* | $C_{max}$, extrap. IU/mL | Clearance mL/kg/h | MRT h | Half-life, terminal h |
|---|---|---|---|---|
| (40.6%) & rVIII-SC | | 1.5fold | 1.9fold | 1.8fold |
| D'D3-FP dimer (83.6%) & rVIII-SC | 3.41 | 3.41 1.8fold | 18.1 2.0fold | 12.8 2.0fold |
| D'D3-FP dimer (89.8%) & rVIII-SC | 3.97 | 2.95 2.0fold | 19.6 2.2fold | 13.1 2.0fold |

*degree of D'D3-FP dimer sialylation given in brackets

EXAMPLE 8.2

Prolongation of Pharmacokinetics of Full-Length FVIII by Co-Administration of Highly Sialylated D'D3-FP Dimer in Rats Material and Methods Animals: Female Crl:CD (Sprague Dawley) rats in a weight range of 220-300 g were breed at Charles River Laboratories (Sulzfeld, Germany). In house, the animals were kept at standard housing conditions, i.e. at 21-22° C. under a 12 h/12 h light-darkness cycle. Animals were fed ad libitum with standard rat diet (Ssniff-Versuchsdiäten, Soest, Germany). Tap water was supplied ad libitum. Animal husbandry and study procedures complied with the German Animal Welfare law and European Union regulations.

Laboratory evaluations: The test articles were administered i.v. by a single injection into the lateral tail vein at a volume of 3 mL/kg. All D'D3-FP dimer preparations were administered at a dose level of 1000 µg/kg based on human albumin values, and co-administered with 200 IU/kg Advate® (nominal chromogenic activity) after incubating for approximately 30 minutes at +37° C. Animals receiving only Advate® served as control (Table 7).

Blood samples were taken retro-orbitally under short term anaesthesia at 5 min, 2, 4, 8, 24, 32, 48 and 72 h after intravenous bolus injection using an alternating sampling scheme. The PK profile was taken from two cohorts of rats per group (n=3 per time-point, n=6 per group). Blood samples were anticoagulated using sodium citrate (2 parts sodium citrate 3.13%+8 parts blood), processed to plasma and stored at −20° C. for the determination of FVIII antigen and/or albumin.

D'D3-FP dimer exposure was determined by measurement of the albumin part of the protein using an immunoassay specific for human albumin (example 7), and FVIII: Ag plasma levels were detected with the FVIII Asserachrom ELISA testkit from Stago, S.A.S., France.

TABLE 7

Treatment groups (experiment-wise)

| Treatment* | Sialylation [%] | D'D3-FP dimer dose [mg albumin/kg] | FVIII dose [IU FVIII: C/kg] |
|---|---|---|---|
| Advate ® | — | | 200 |
| D'D3-FP dimer (B-140526) & Advate ® | 40.6% | 1 | 200 |
| D'D3-FP dimer (B-140825) & Advate ® | 87.3% | 1 | 200 |

FVIII: C = chromogenic FVIII activity
*Lot # given in brackets

Results

Figure 3:
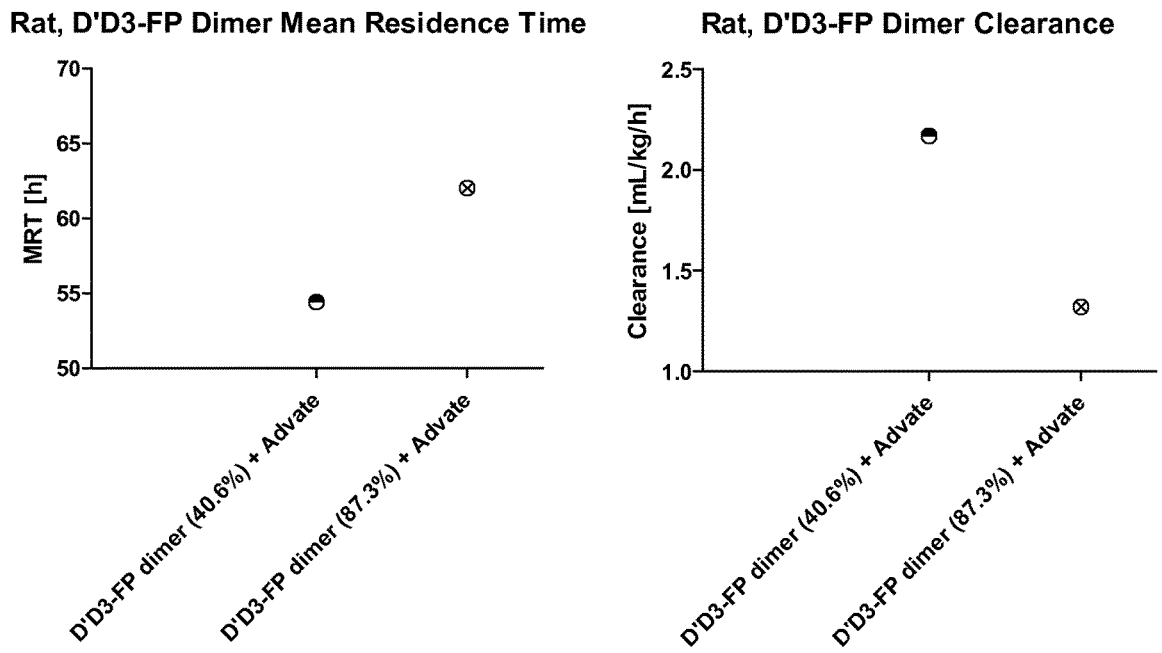
FIG. 3: Mean residence time and clearance (mean) of D'D3-FP dimer quantified as albumin in rats, as determined in Example 8.2.

D'D3-FP dimer was quantified via its albumin component, and measurements were performed up to 72 h p.a., and measured data were well above the detection limit over the whole observation period. Mean residence time (MRT) and clearance (CL) were estimated by non-compartmental methods and the data are presented in FIG. 3. PK characteristics of D'D3-FP dimer in the group of Advate® co-administered with the D'D3-FP dimer with 40.6% sialylation had a shorter MRT and higher clearance as when co-administered with the D'D3-FP dimer preparation with 87.3% sialylation.

Figure 4:
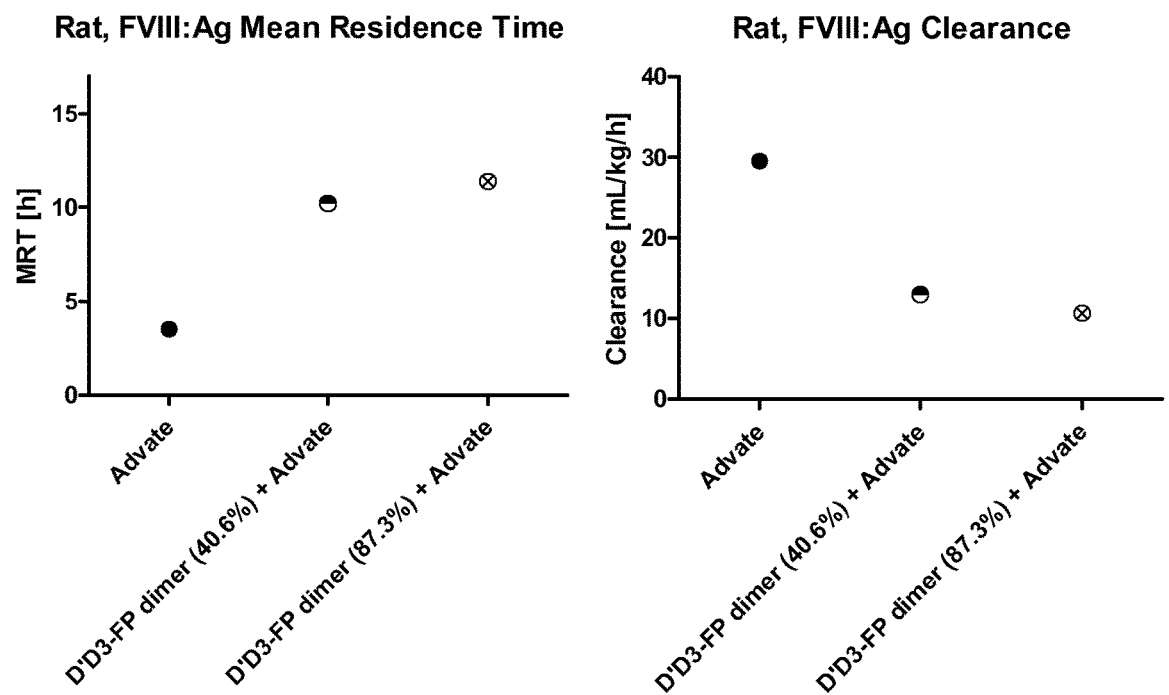
FIG. 4: Mean residence time and clearance (mean) of full length Factor VIII quantified as FVIII antigen in rats, as determined in Example 8.2.
Figure 6:
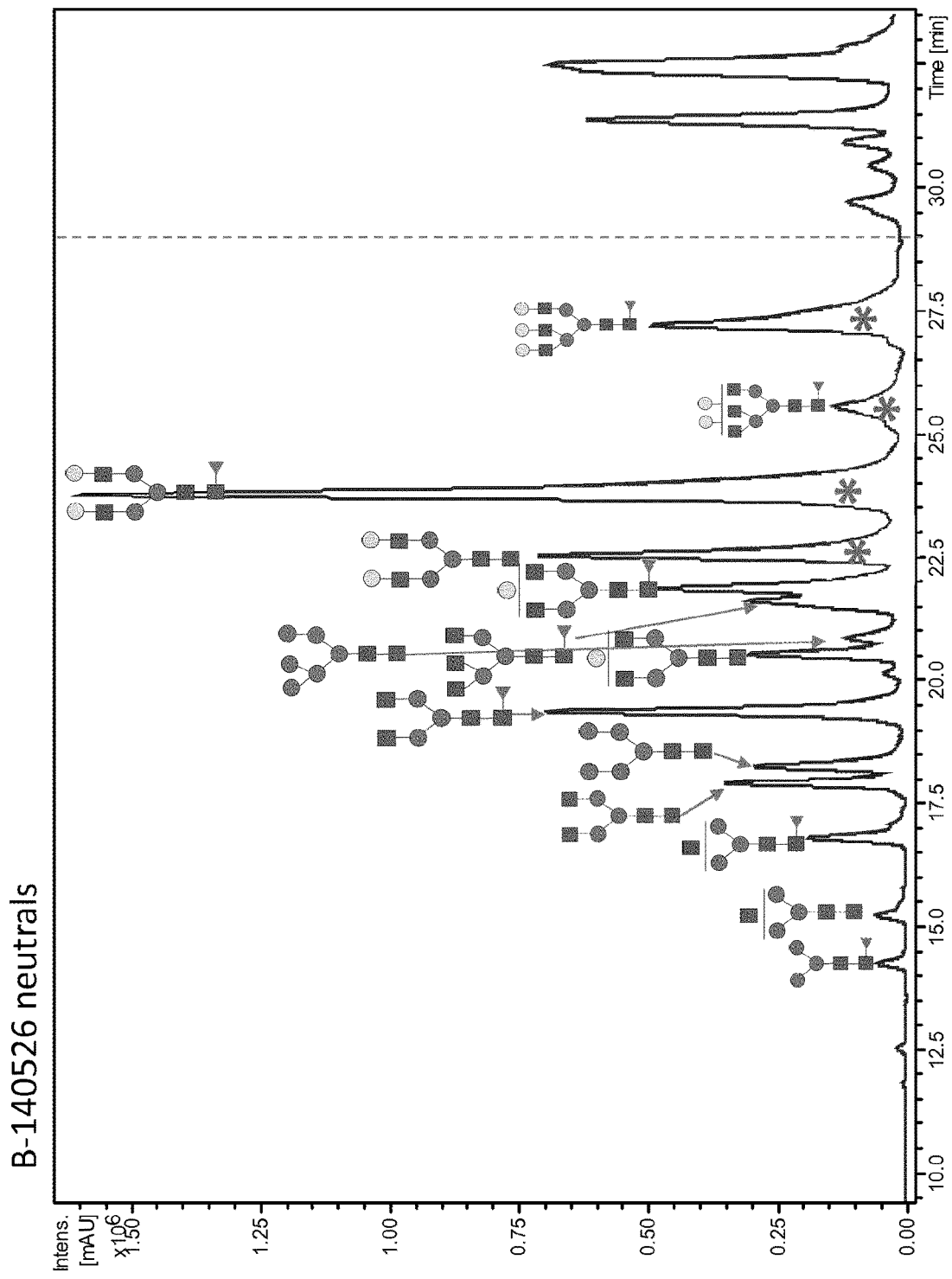
FIG. 6: Profil of lot B-140526 showing the neutral N-glycans
Figure 7:
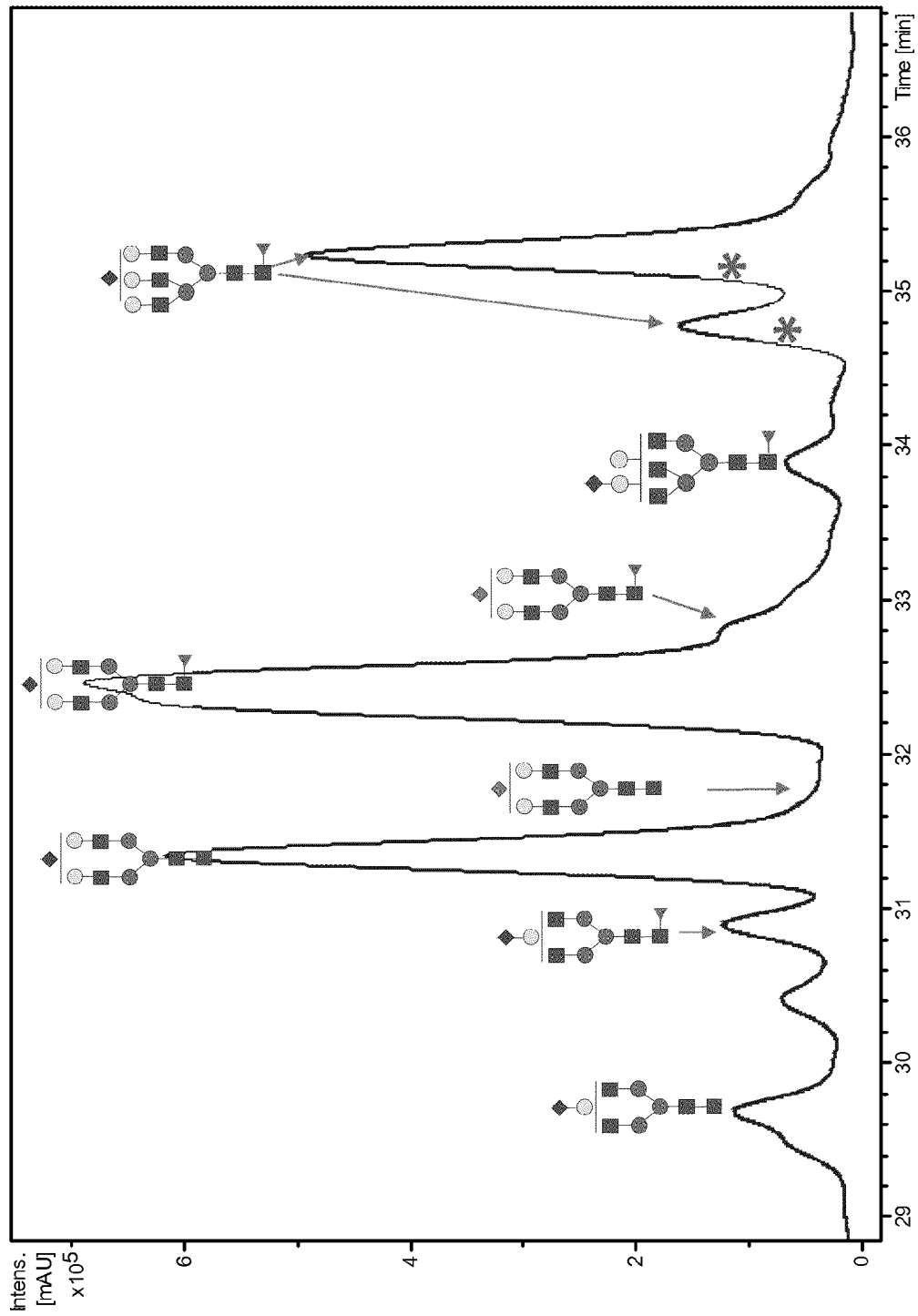
FIG. 7: Profil of lot B-140526 showing the mono-sialo N-glycans
Figure 8:
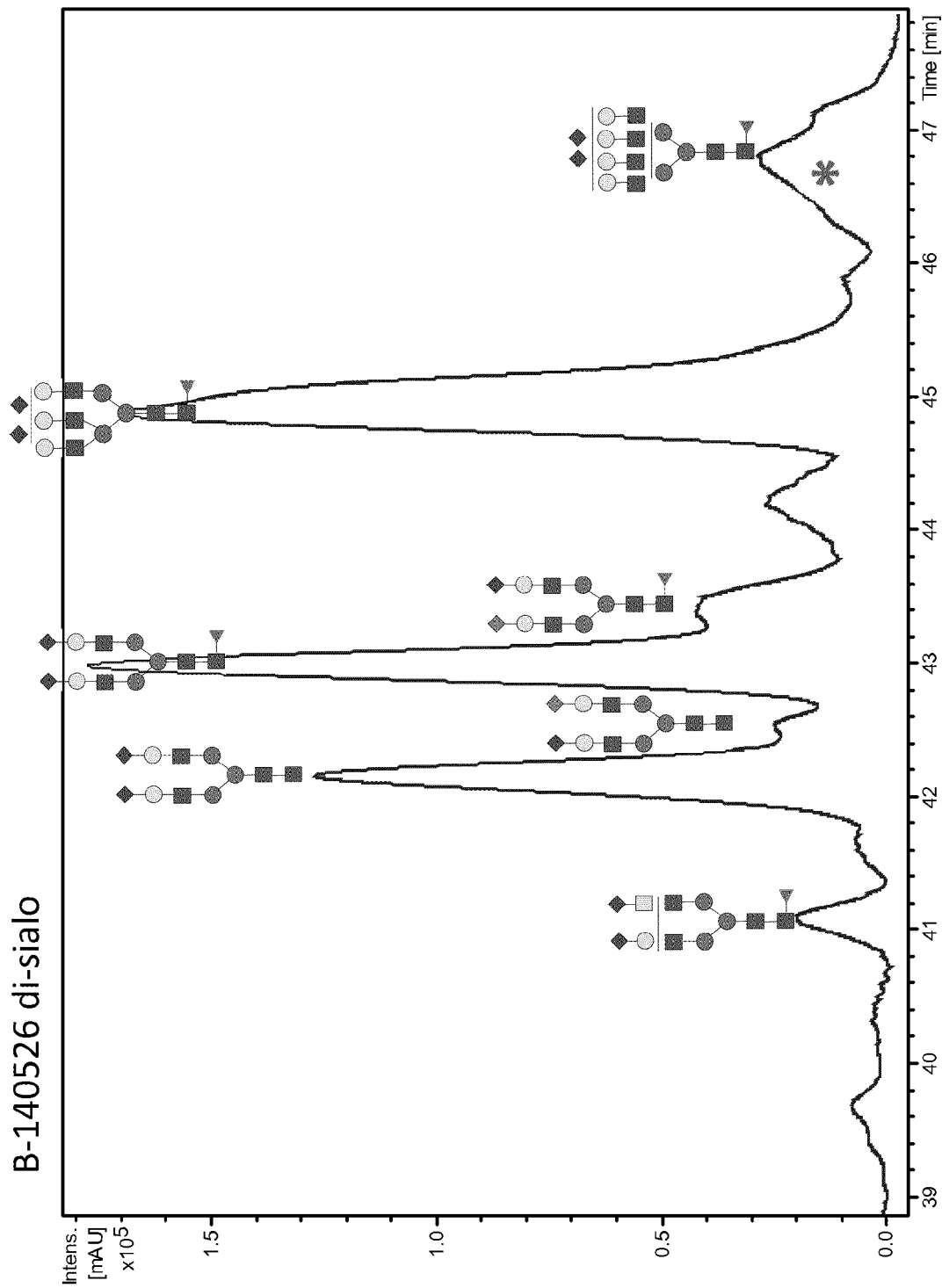
FIG. 8: Profil of lot B-140526 showing the di-sialo N-glycans
Figure 9:
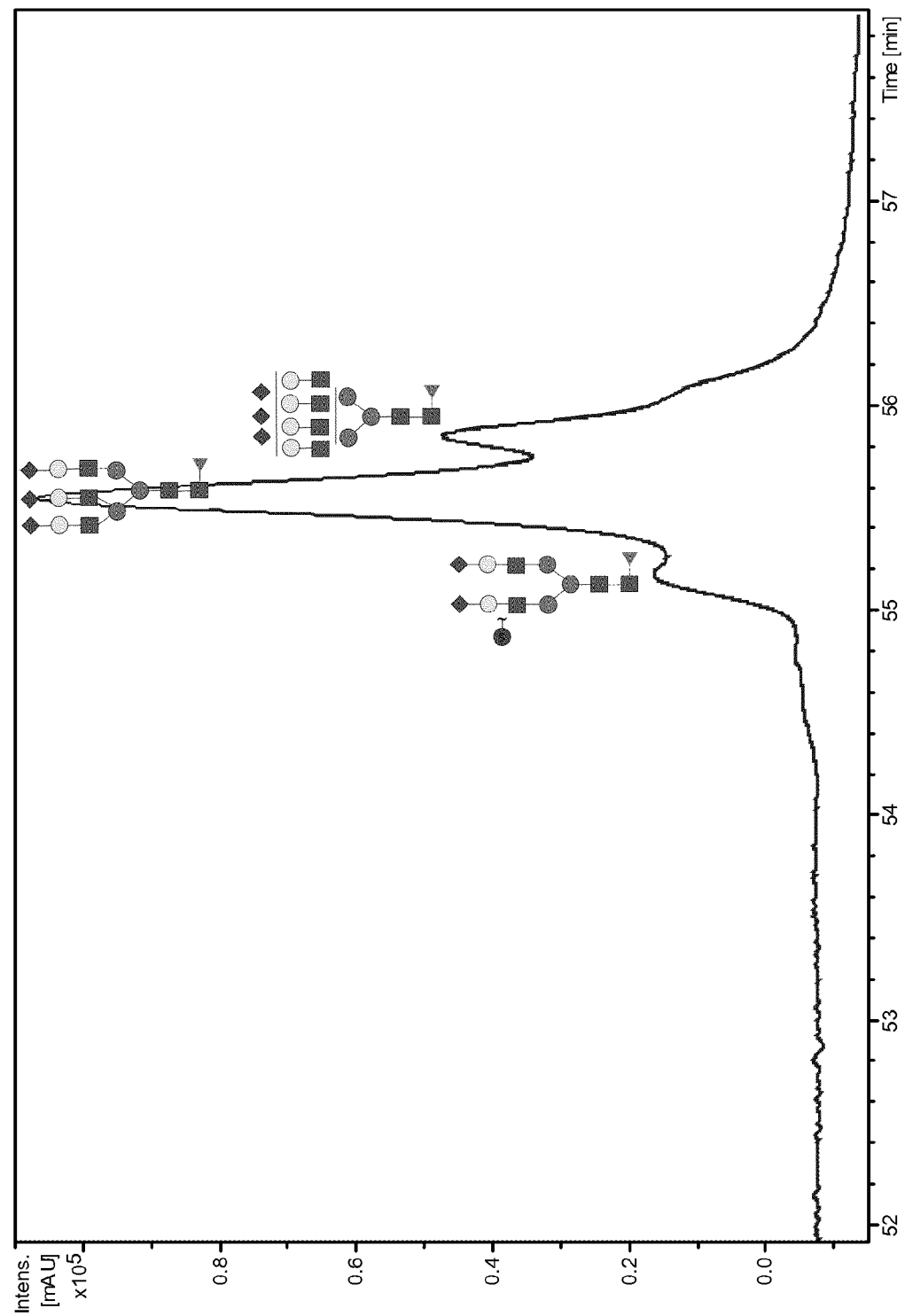
FIG. 9: Profil of lot B-140526 showing the tri-sialo N-glycans
Figure 10:
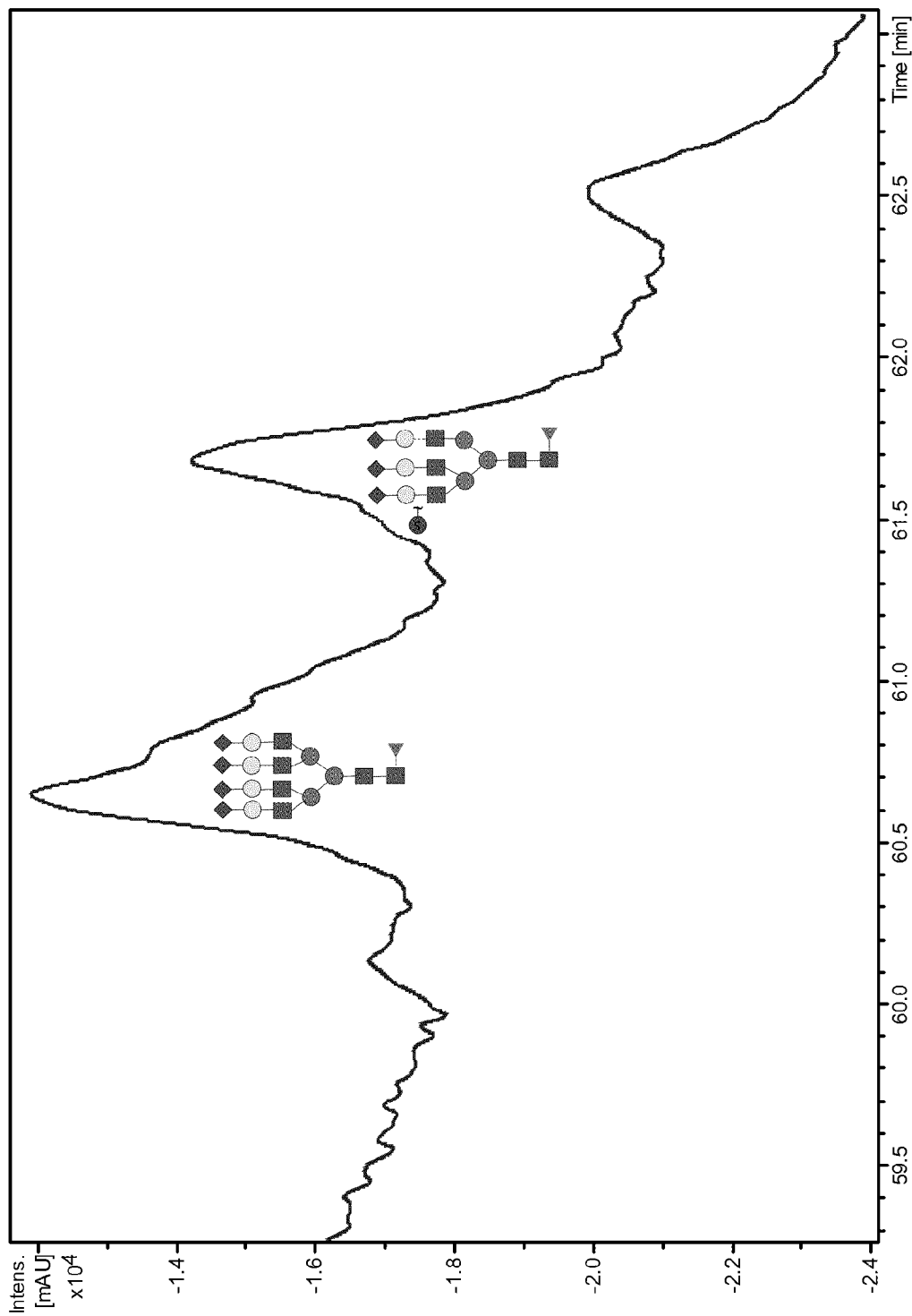
FIG. 10: Profil of lot B-140526 showing the tetra-sialo N-glycans
Figure 11:
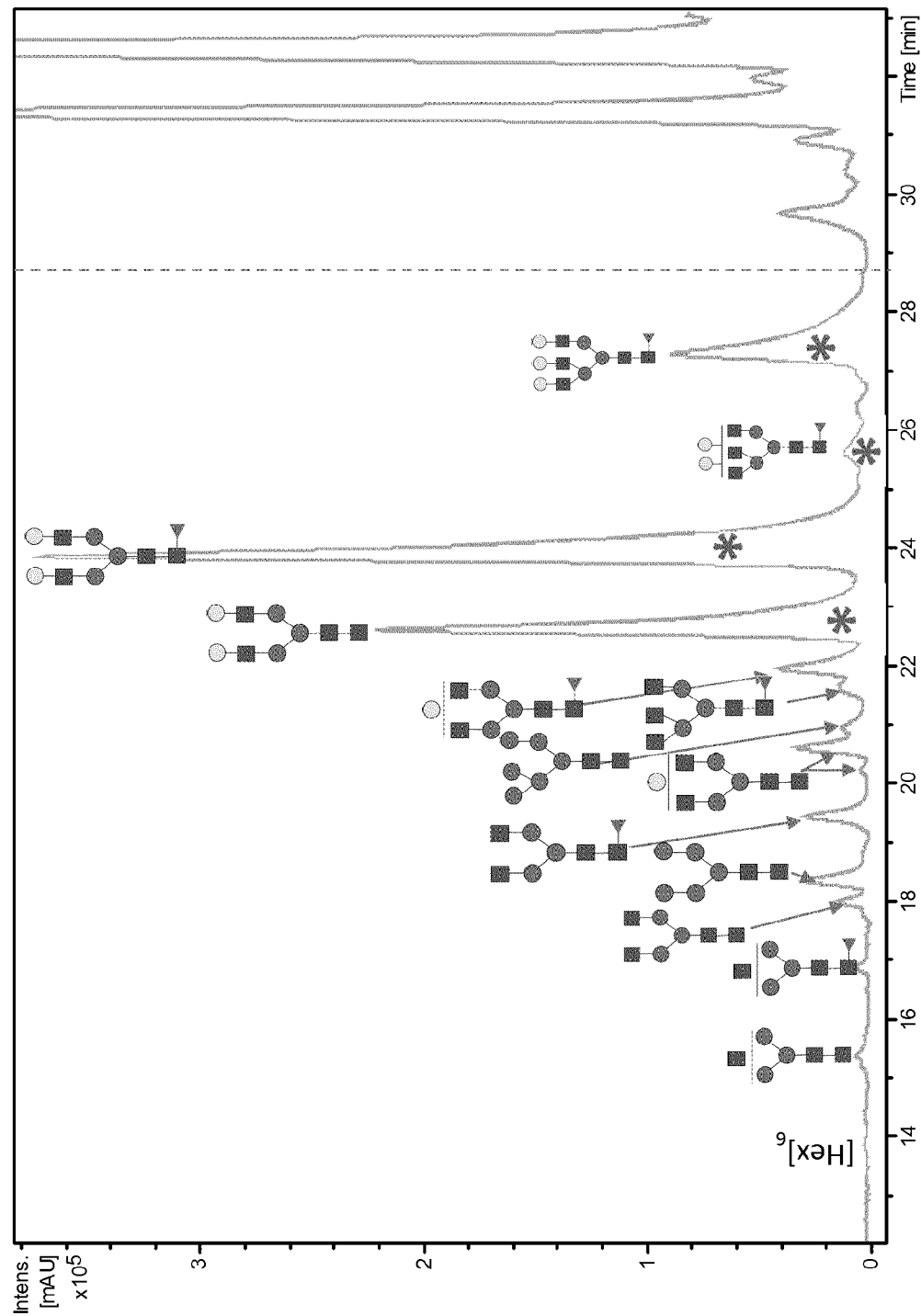
FIG. 11: Profil of lot B-140616KS showing the neutral N-glycans
Figure 12:
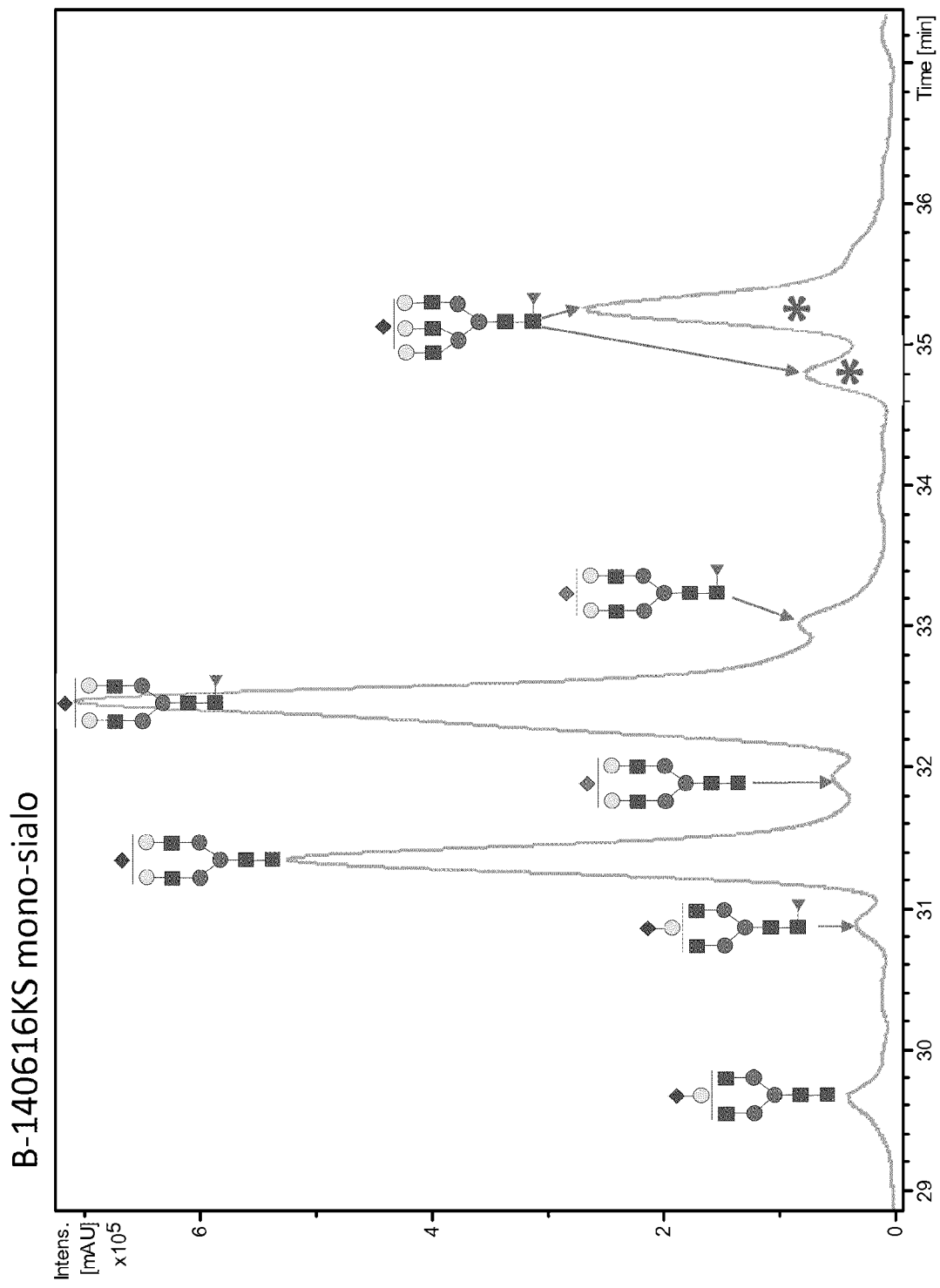
FIG. 12: Profil of lot B-140616KS showing the mono-sialo N-glycans
Figure 13:
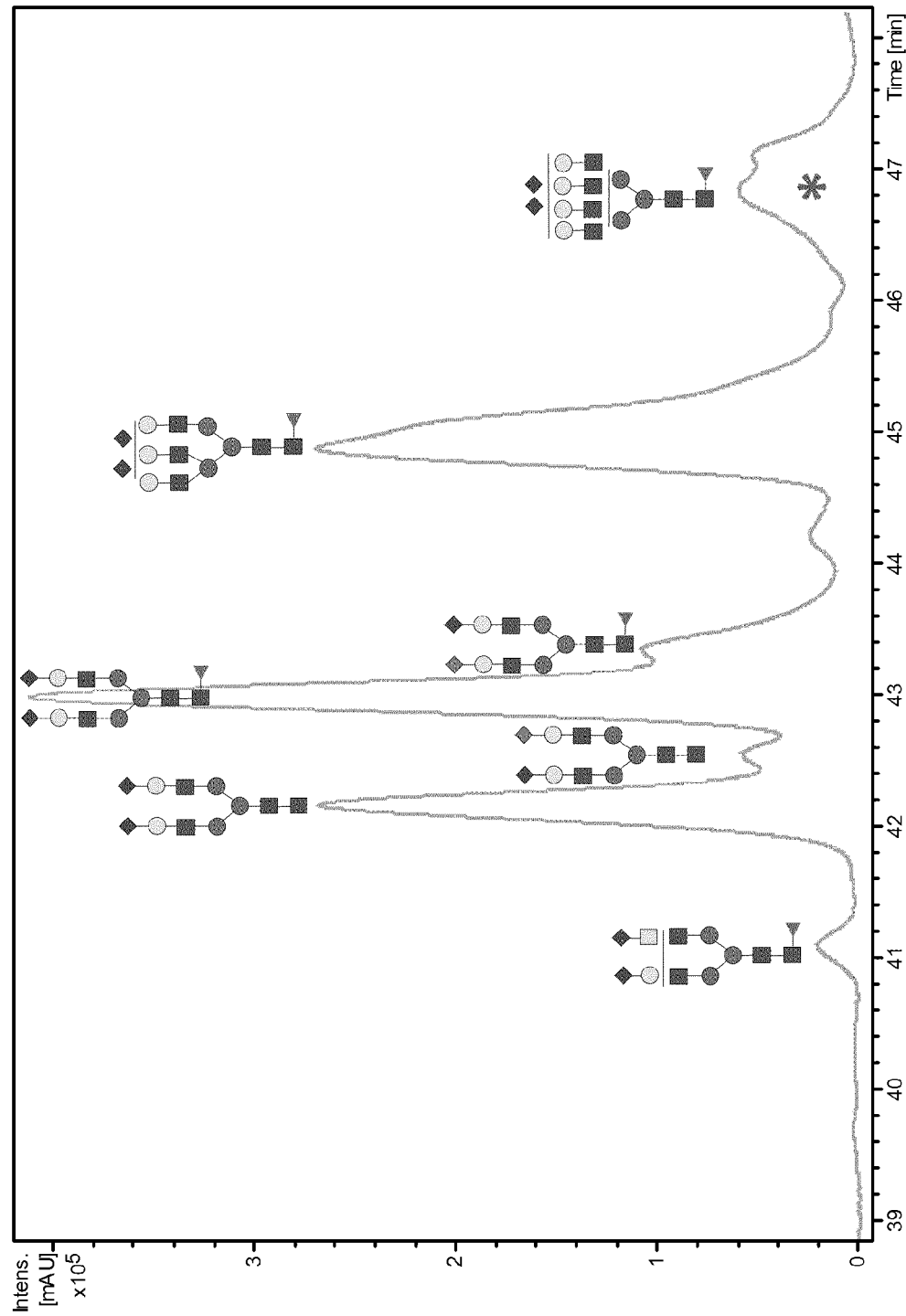
FIG. 13: Profil of lot B-140616KS showing the di-sialo N-glycans
Figure 14:
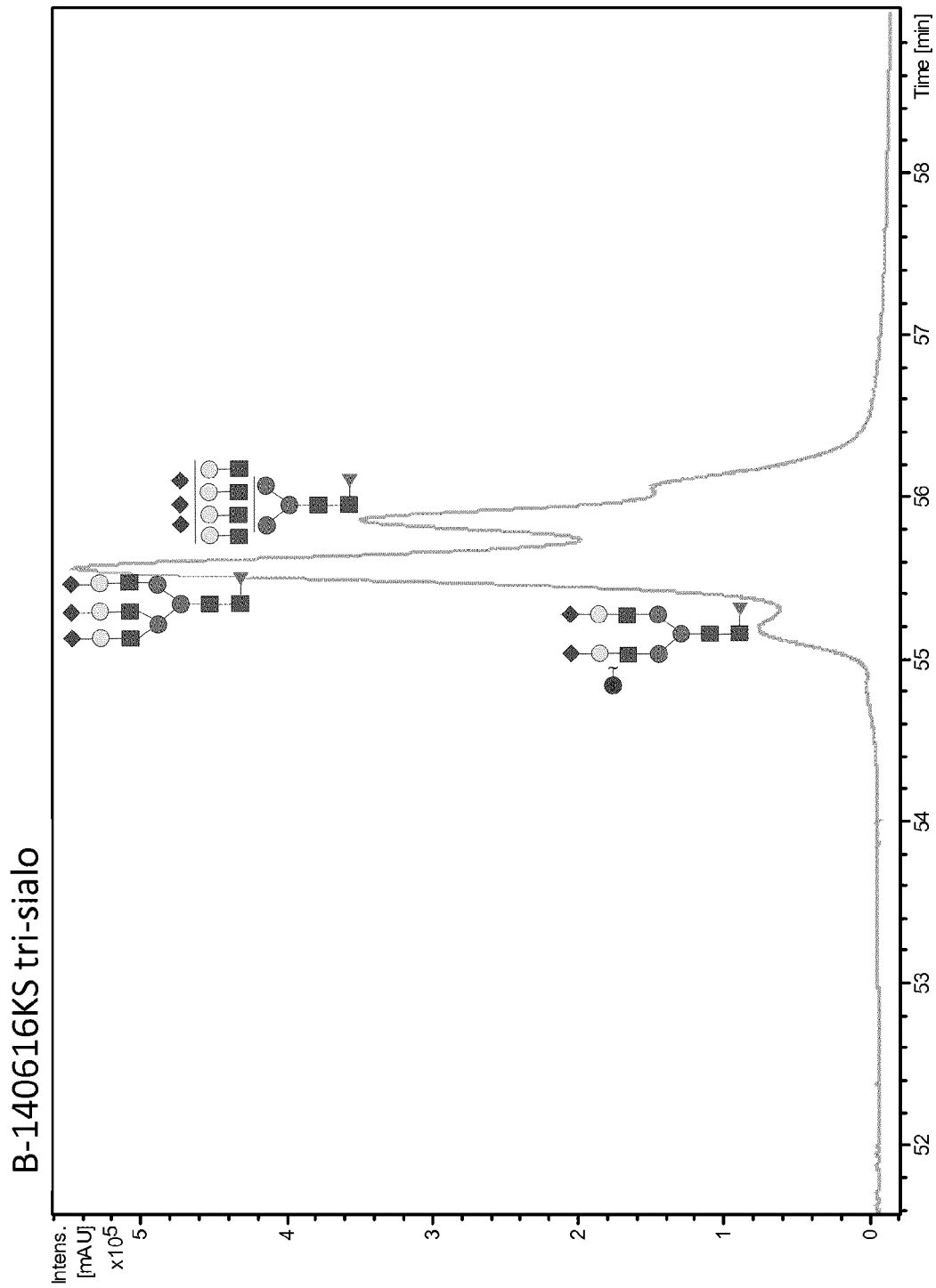
FIG. 14: Profil of lot B-140616KS showing the tri-sialo N-glycans
Figure 15:
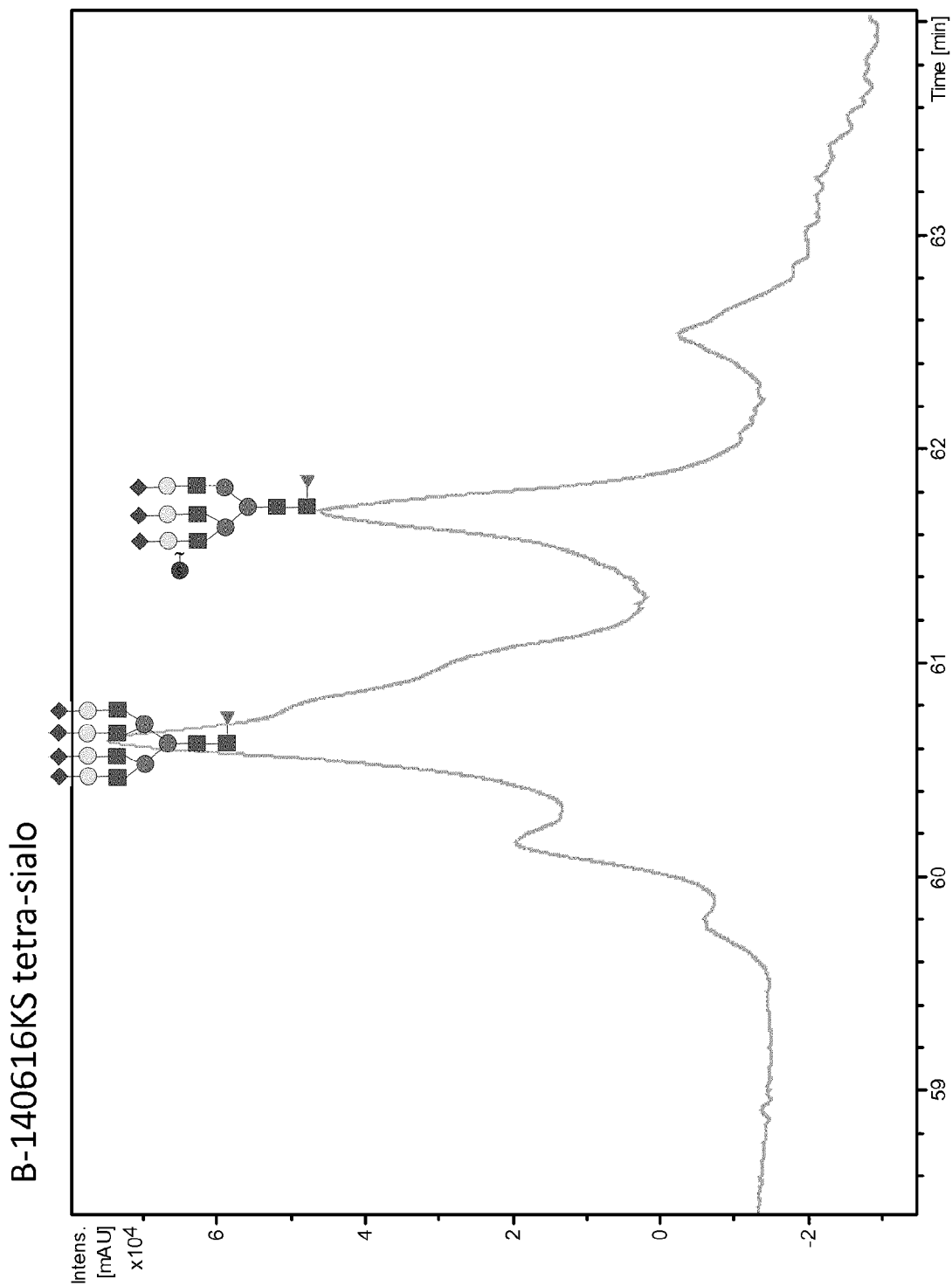
FIG. 15: Profil of lot B-140616KS showing the tetra-sialo N-glycans
Figure 16:
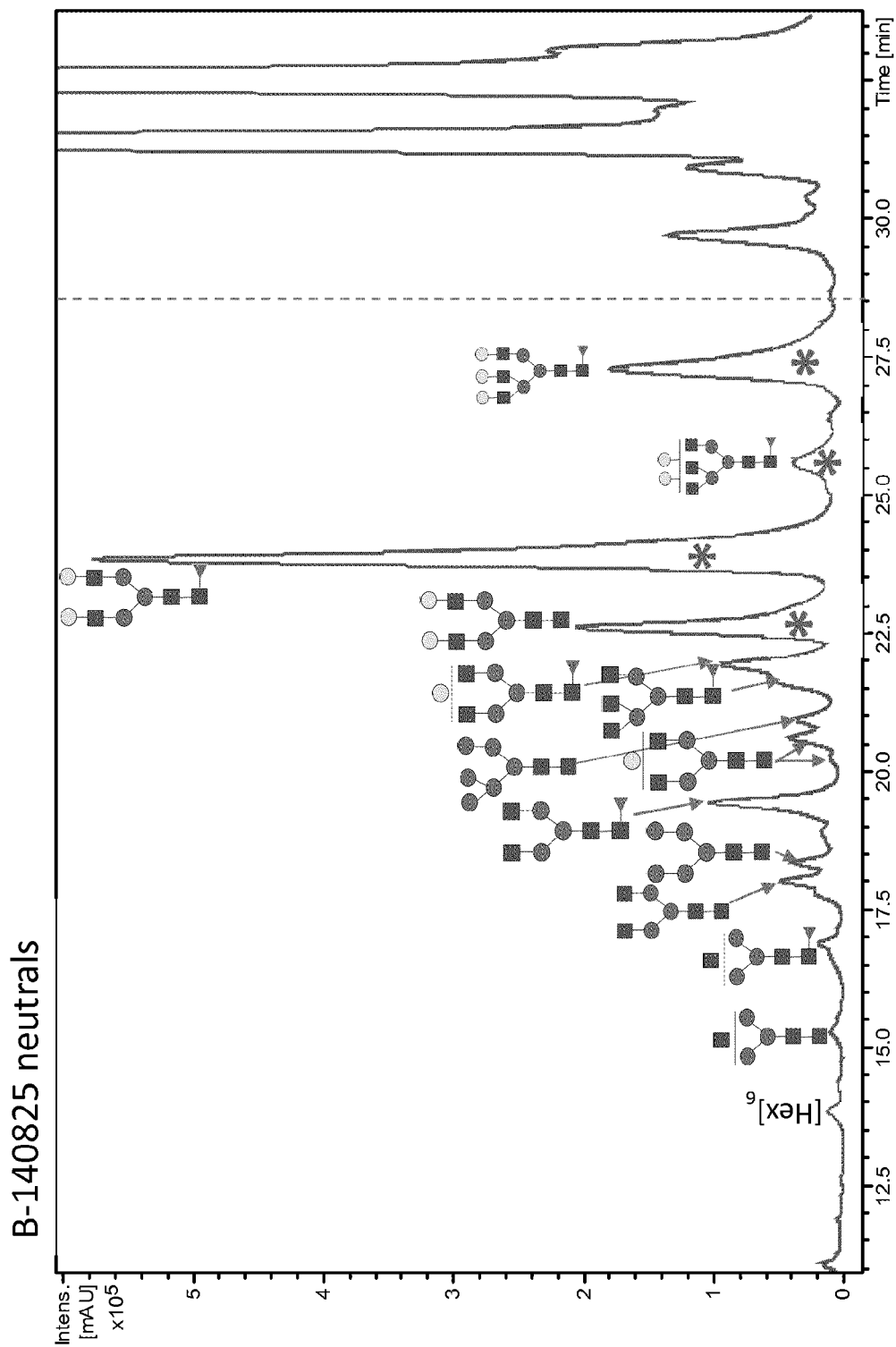
FIG. 16: Profil of lot B-140825 showing the neutral N-glycans
Figure 17:
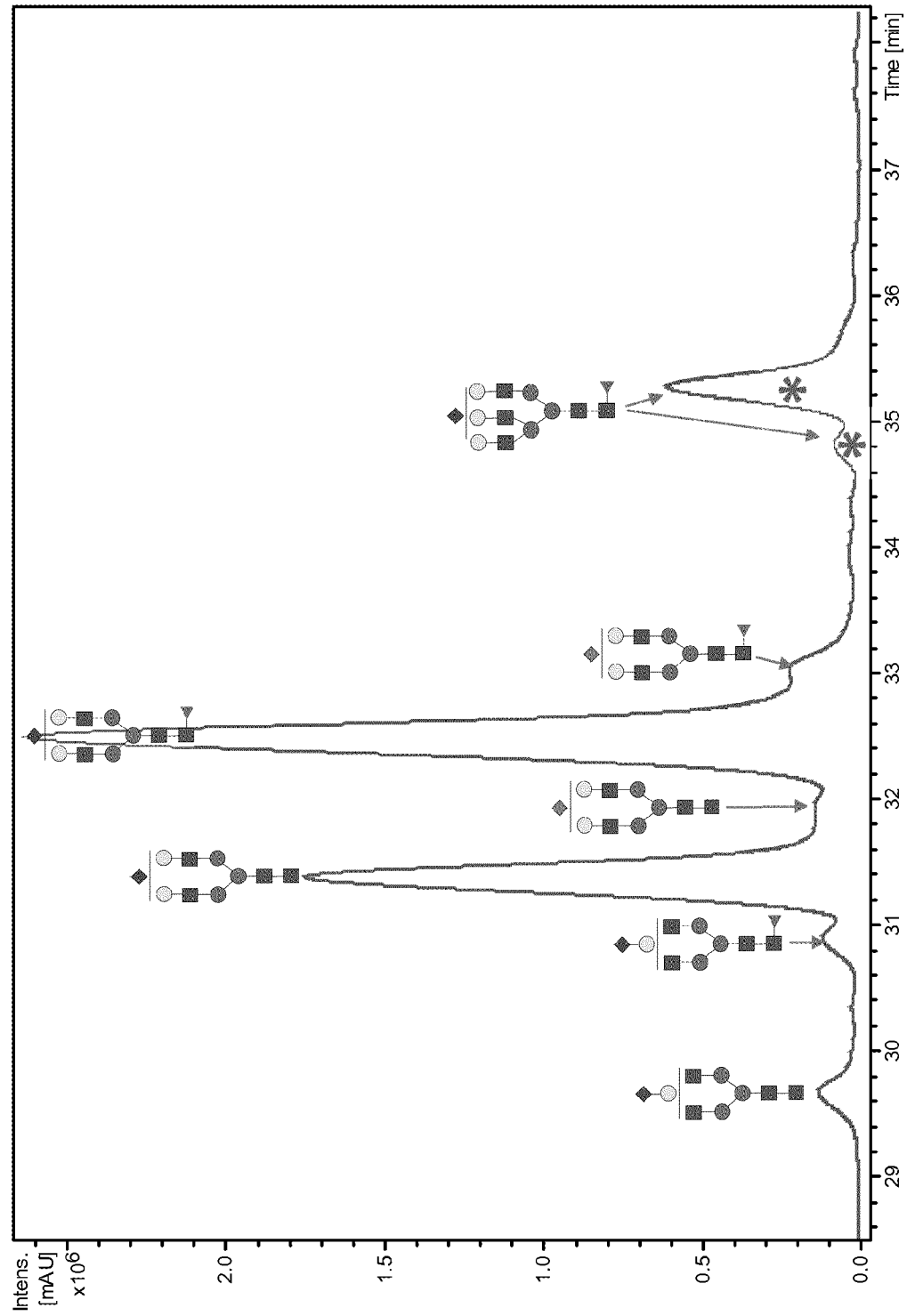
FIG. 17: Profil of lot B-140825 showing the mono-sialo N-glycans
Figure 18:
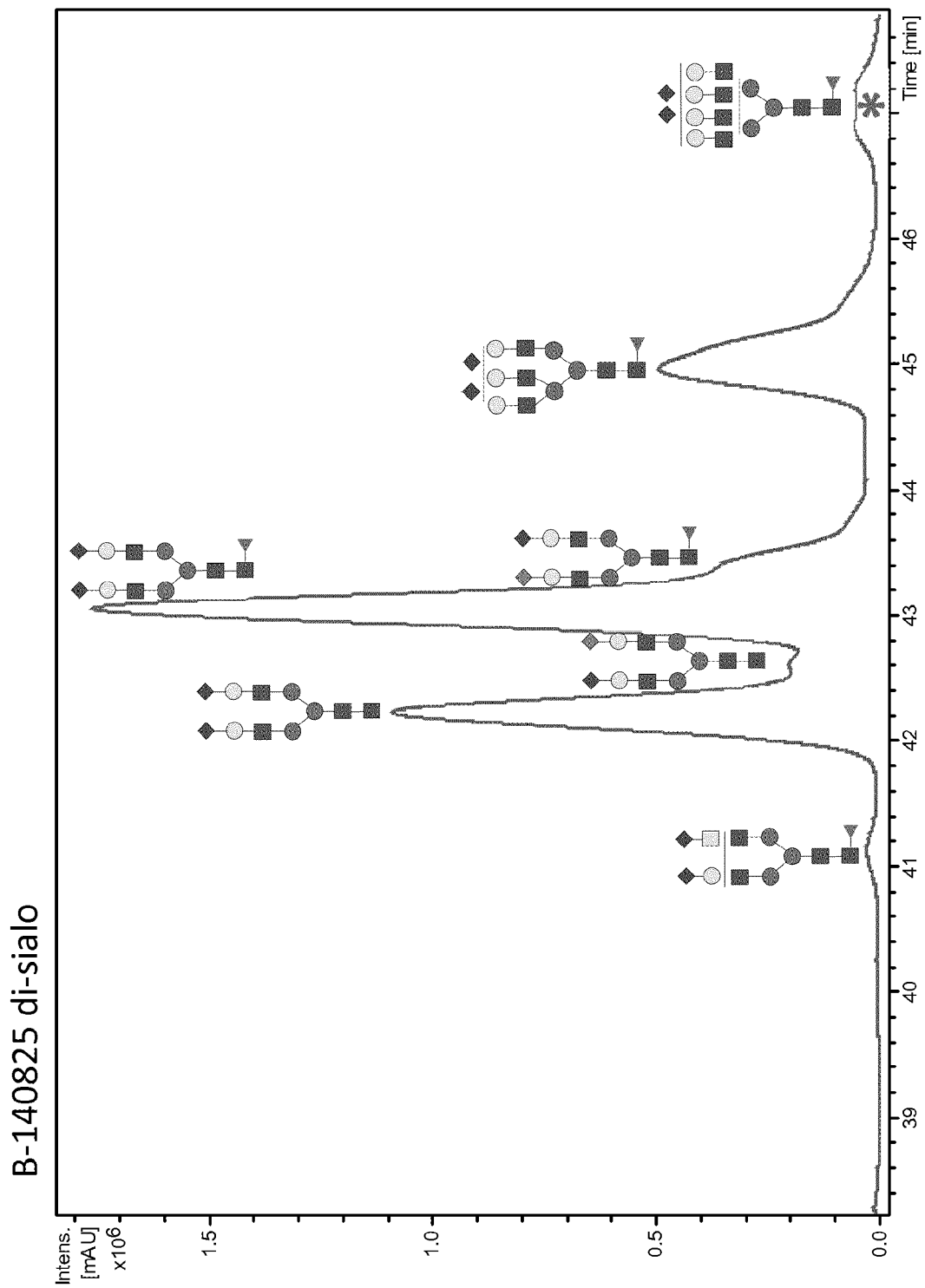
FIG. 18: Profil of lot B-140825 showing the di-sialo N-glycans
Figure 19:
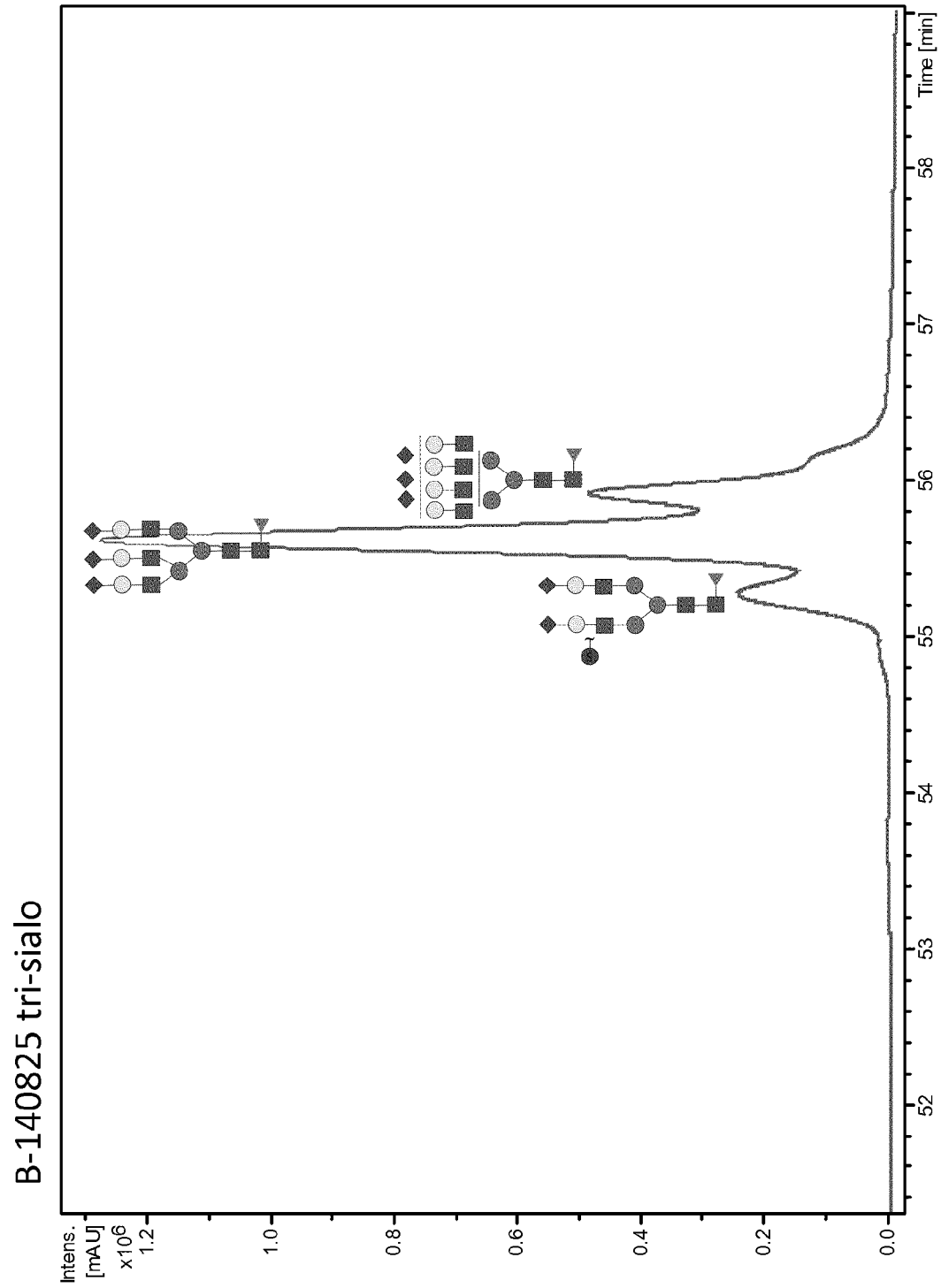
FIG. 19: Profil of lot B-140825 showing the tri-sialo N-glycans
Figure 20:
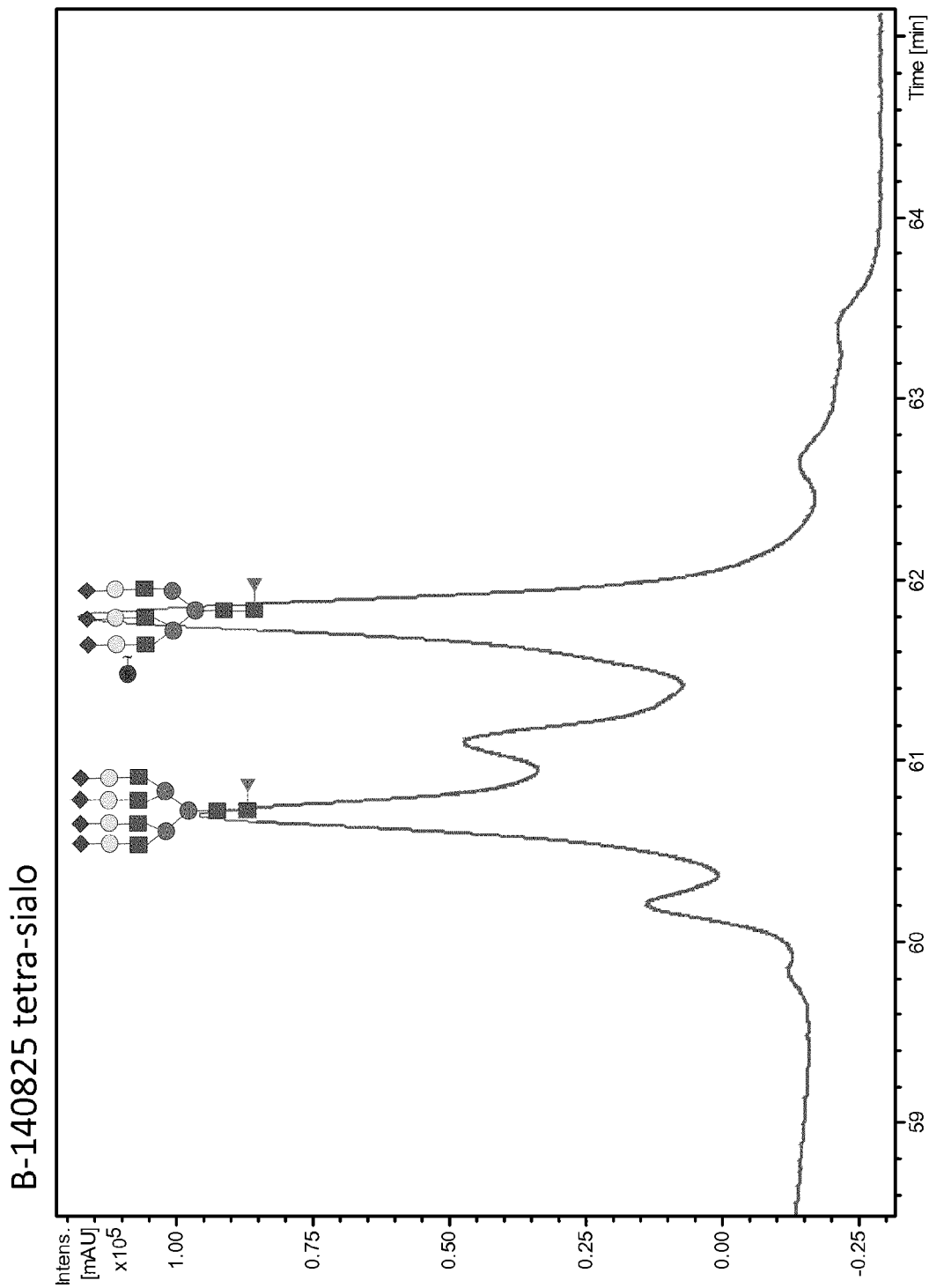
FIG. 20: Profil of lot B-140825 showing the tetra-sialo N-glycans
Figure 21:
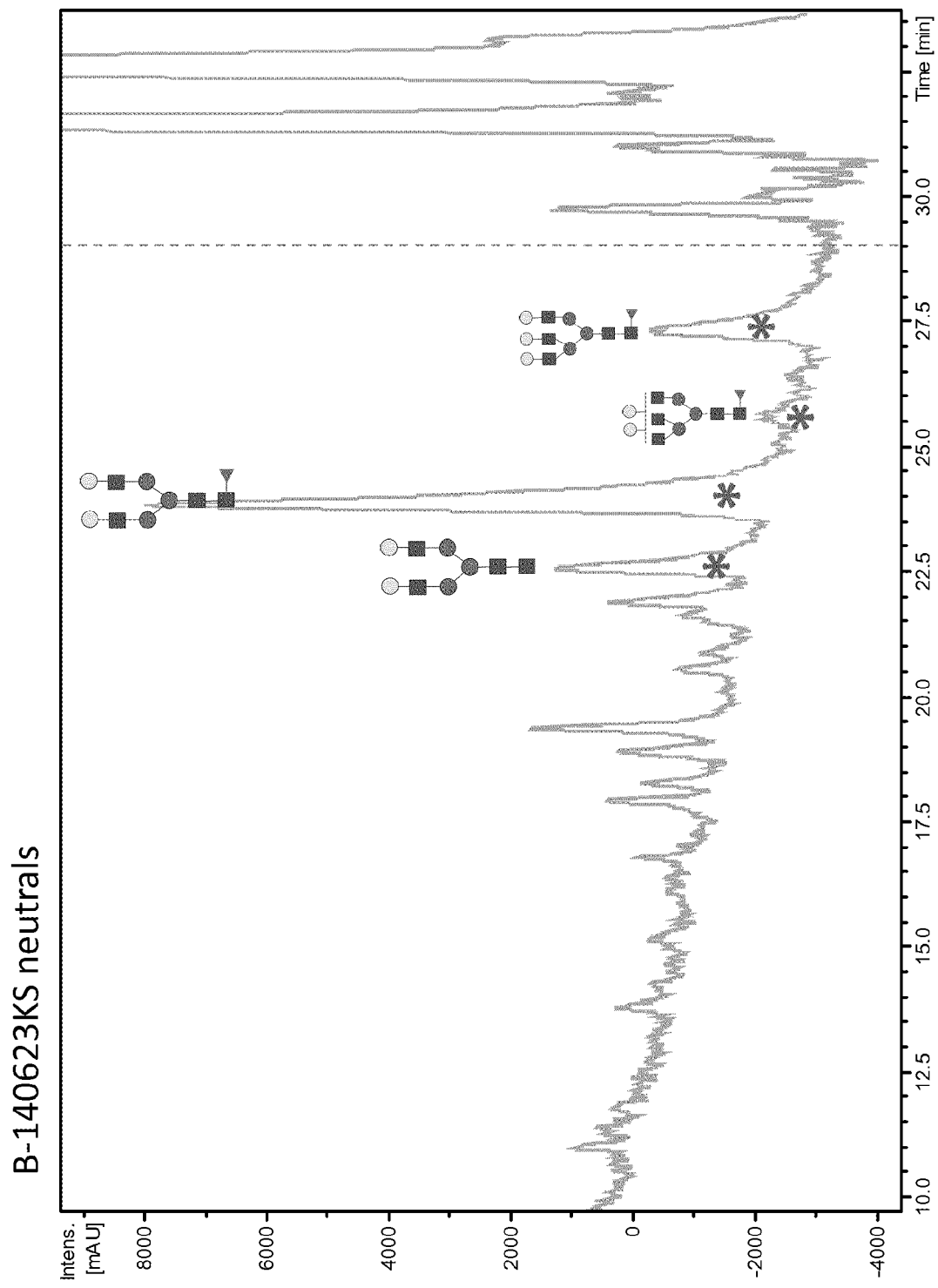
FIG. 21: Profil of lot B-140623KS showing the neutral N-glycans
Figure 22:
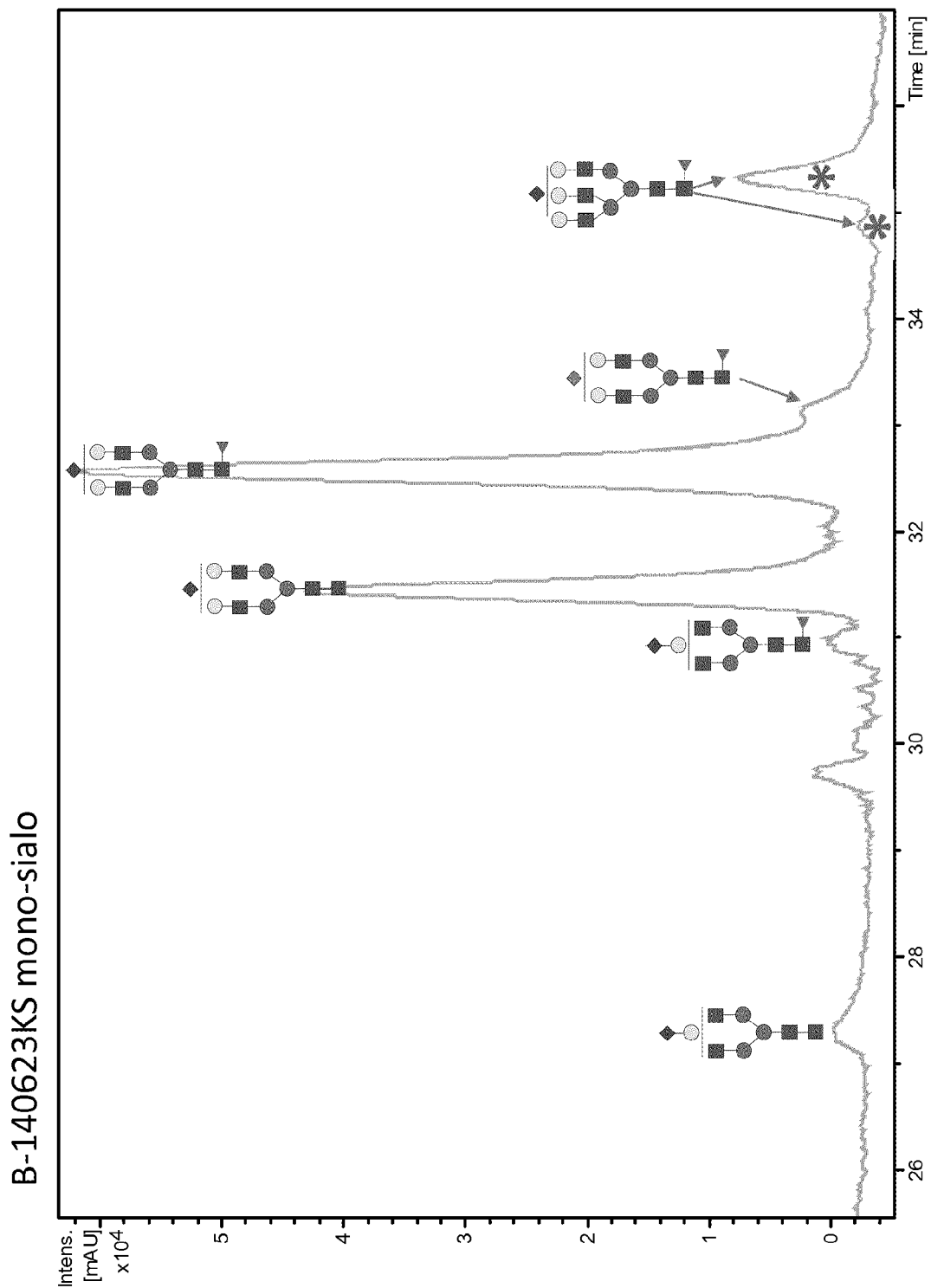
FIG. 22: Profil of lot B-140623KS showing the mono-sialo N-glycans
Figure 23:
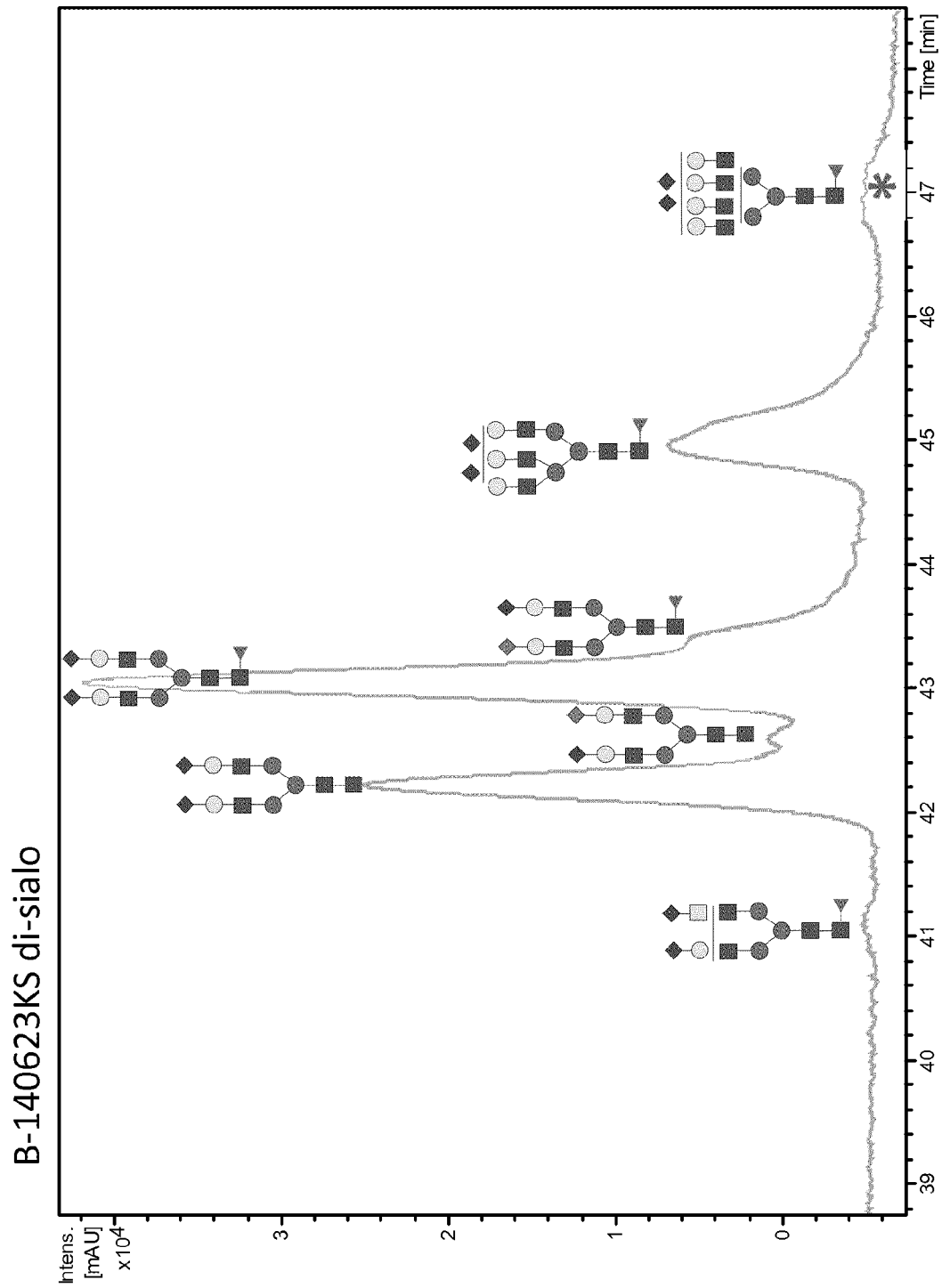
FIG. 23: Profil of lot B-140623KS showing the di-sialo N-glycans
Figure 24:
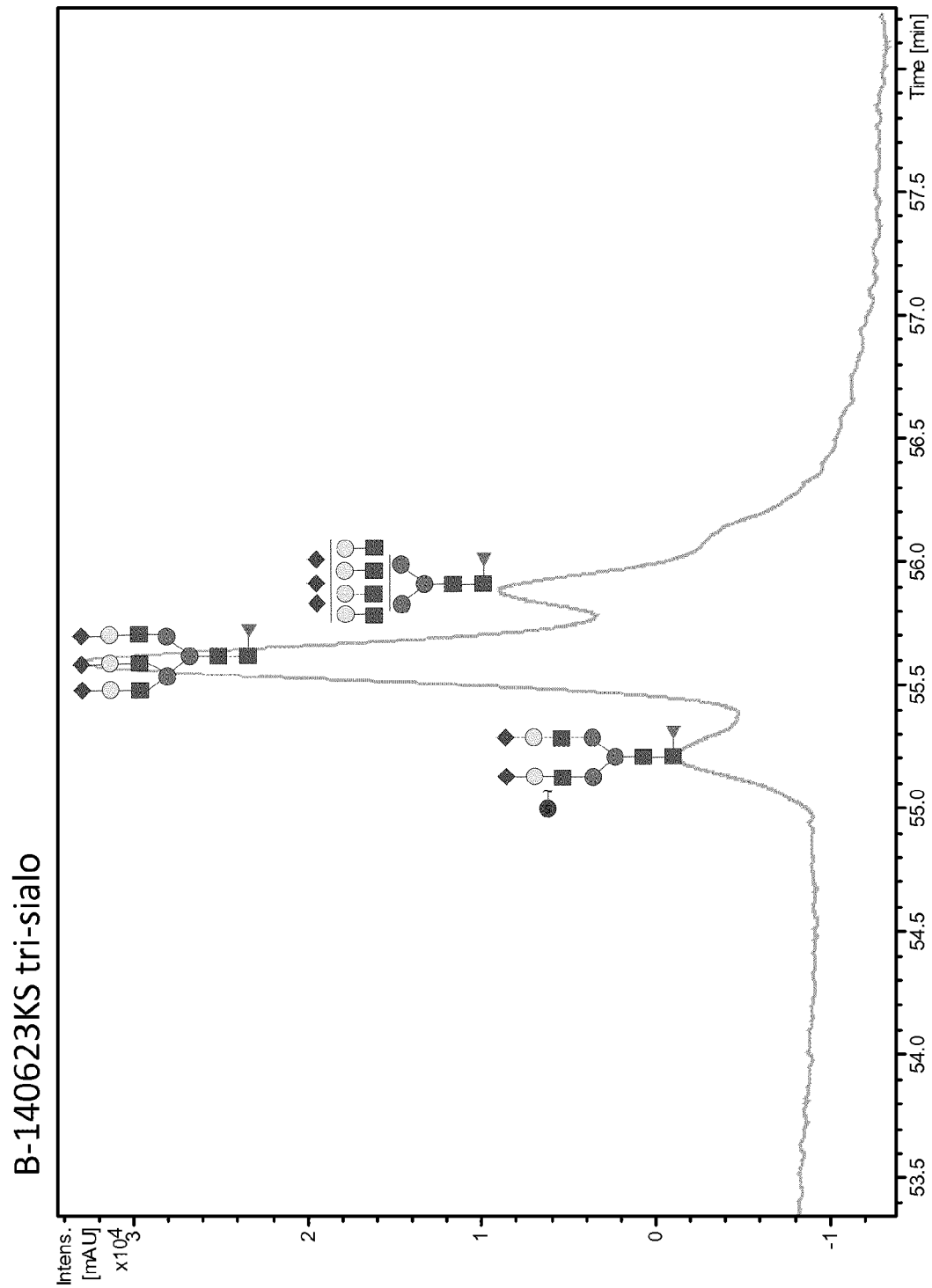
FIG. 24: Profil of lot B-140623KS showing the tri-sialo N-glycans
Figure 25:
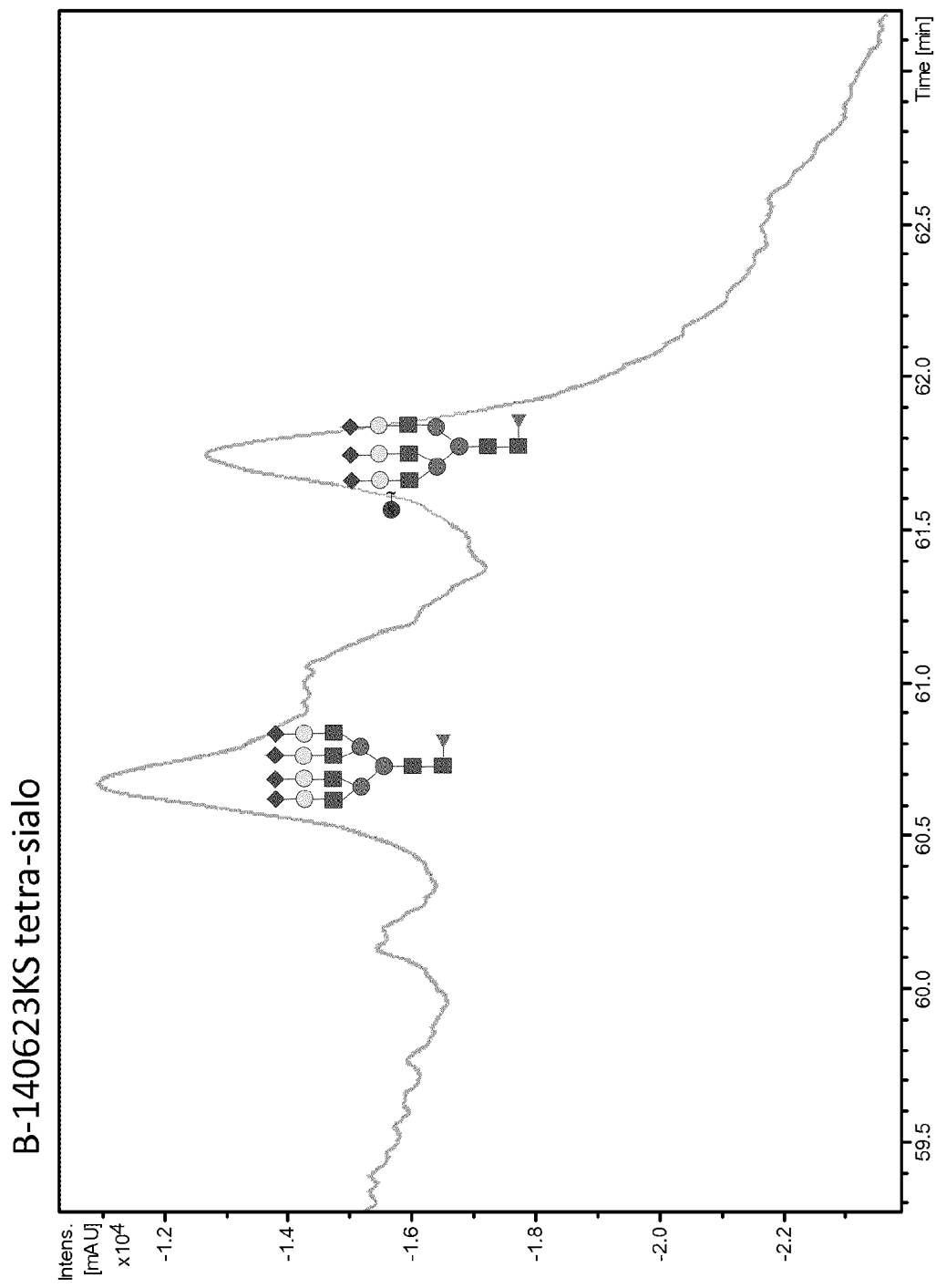
FIG. 25: Profil of lot B-140623KS showing the tetra-sialo N-glycans
Figure 26:
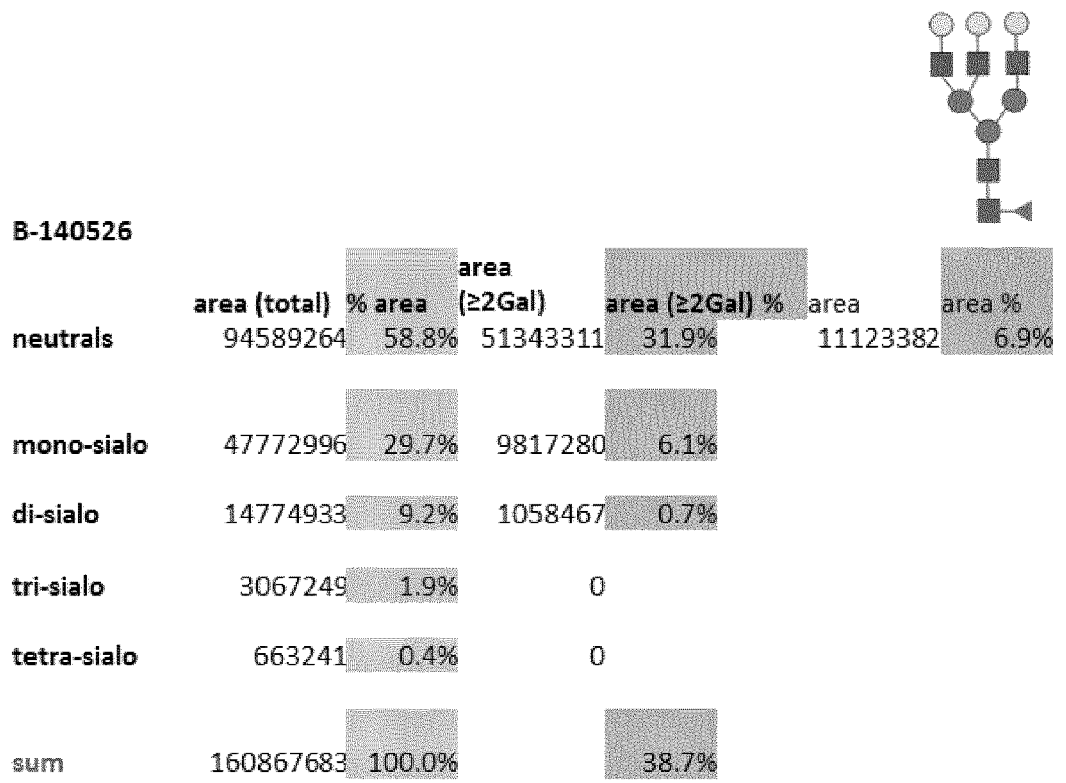
FIG. 26: Quantitative determination of N-glycans with two or more terminal and non-sialylated galactose residues of the comparative sample B140526. The first column shows the quantitative distribution of all N-glycans for neutral, mono-sialo, di-sialo, tri-sialo and tetra-sialo N-glycans adding up to 100%. The second column shows the percentage (relating to the 100% of all N-glycans) of N-glycans with two or more terminal and non-sialylated galactose residues. In the present sample only neutral, mono-sialo and di-sialo N-glycans having two or more terminal and non-sialylated galactose residues were detected. The third column shows the percentage (relating to the 100% of all N-glycans) of N-glycans with three or more terminal and non-sialylated galactose residues. In the present sample only neutral N-glycans having three or more terminal and non-sialylated galactose residues were detected.
Figure 27:
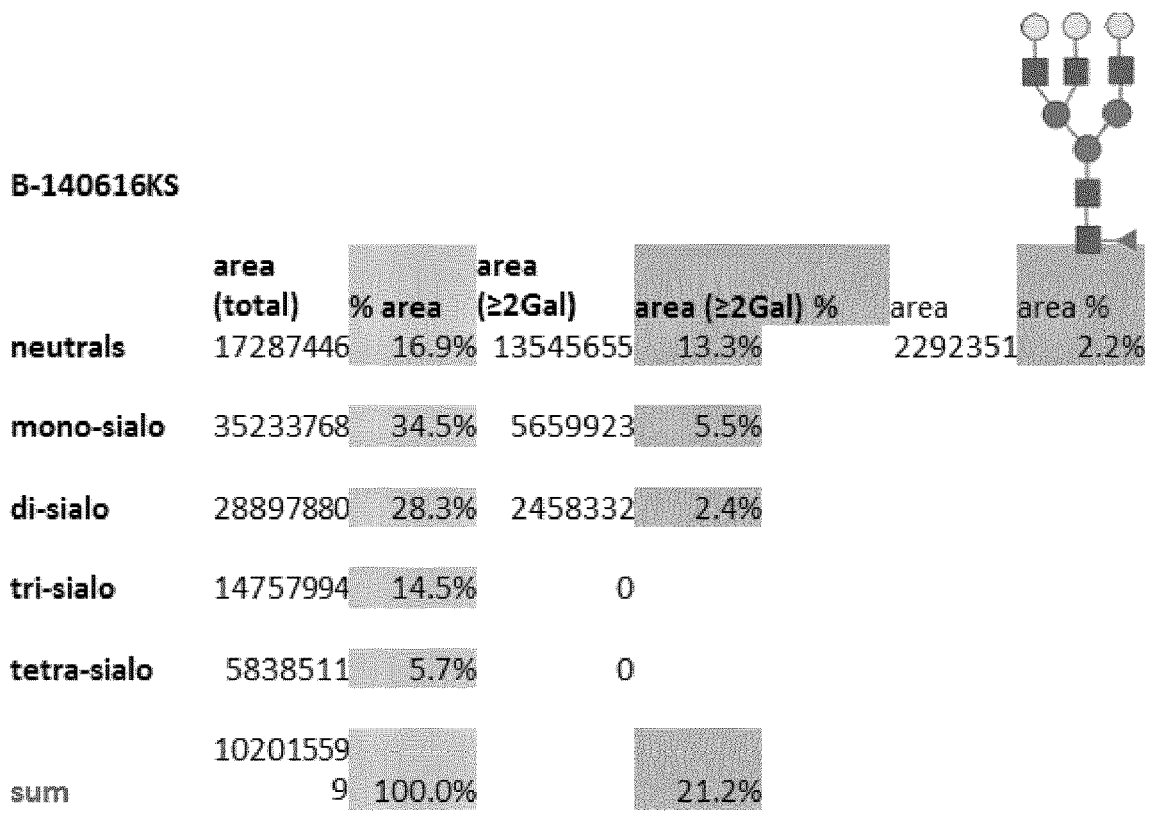
FIG. 27: Quantitative determination of N-glycans with two or more terminal and non-sialylated galactose residues of sample B140616KS according to the invention. The first column shows the quantitative distribution of all N-glycans for neutral, mono-sialo, di-sialo, tri-sialo and tetra-sialo N-glycans adding up to 100%. The second column shows the percentage (relating to the 100% of all N-glycans) of N-glycans with two or more terminal and non-sialylated galactose residues. In the present sample only neutral, mono-sialo and di-sialo N-glycans having two or more terminal and non-sialylated galactose residues were detected. The third column shows the percentage (relating to the 100% of all N-glycans) of N-glycans with three or more terminal and non-sialylated galactose residues. In the present sample only neutral N-glycans having three or more terminal and non-sialylated galactose residues were detected.
Figure 28:
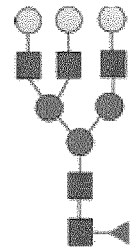
FIG. 28: Quantitative determination of N-glycans with two or more terminal and non-sialylated galactose residues of sample B140825 according to the invention. The first column shows the quantitative distribution of all N-glycans for neutral, mono-sialo, di-sialo, tri-sialo and tetra-sialo N-glycans adding up to 100%. The second column shows the percentage (relating to the 100% of all N-glycans) of N-glycans with two or more terminal and non-sialylated galactose residues. In the present sample only neutral, mono-sialo and di-sialo N-glycans having two or more terminal and non-sialylated galactose residues were detected. The third column shows the percentage (relating to the 100% of all N-glycans) of N-glycans with three or more terminal and non-sialylated galactose residues. In the present sample only neutral N-glycans having three or more terminal and non-sialylated galactose residues were detected.
Figure 29:
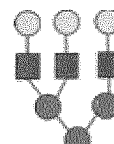
FIG. 29: Quantitative determination of N-glycans with two or more terminal and non-sialylated galactose residues of sample B140623KS according to the invention. The first column shows the quantitative distribution of all N-glycans for neutral, mono-sialo, di-sialo, tri-sialo and tetra-sialo N-glycans adding up to 100%. The second column shows the percentage (relating to the 100% of all N-glycans) of N-glycans with two or more terminal and non-sialylated galactose residues. In the present sample only neutral, mono-sialo and di-sialo N-glycans having two or more terminal and non-sialylated galactose residues were detected. The third column shows the percentage (relating to the 100% of all N-glycans) of N-glycans with three or more terminal and non-sialylated galactose residues. In the present sample only neutral N-glycans having three or more terminal and non-sialylated galactose residues were detected.

In line with this observation, the pharmacokinetic profile of the co-administered FVIII (200 IU/kg nominal chromogenic FVIII activity), quantified as FVIII:Ag via ELISA, was modified accordingly. It shall be mentioned that samples could be measured until 4-8 h p.a. with the Advate®-treated group and until 24-32 h p.a. with the D'D3-FP dimer co-treated groups, thereafter the values were below the limit of detection of the assay of 117 mIU/mL. Clearly, Advate® alone had the shortest MRT and highest clearance, which was generally prolonged when D'D3-FP dimer was co-administered (FIG. 4). Those D'D3-FP dimers, which had a longer exposure by themselves, also prolonged the FVIII PK profile. Thus, MRT of the D'D3-FP dimer with 40.6% sialylation was shorter and clearance was higher compared to D'D3-FP dimer with sialylation >85%. Thus, the pharmacokinetic profile of FVIII:Ag was dependent on the sialylation of D'D3-FP dimer, i.e., shortest PK was observed with 40.6% sialylation and longest PK with those of >85% sialylation.

Evaluation of PK characteristics of D'D3-FP dimer was done in more detail, i.e. additionally calculating maximal concentrations ($C_{max}$) and terminal half-life (t½) in a non-compartmental model, as well as calculating the x-fold increases over Advate® given alone (Table 8).

Sialylation between 87.3% and 40.6% influenced clearance of D'D3-FP dimer by more than 1.5-fold (1.32 mL/kg/h for the 87.3% D'D3-FP dimer and 2.17 mL/kg/h for the 40.6% D'D3-FP dimer as determined by measuring the albumin concentration over time). This relates to slight effects on mean residence time (MRT, +14%, i.e. 54.4 h to 62.0 h) and terminal half-life (t½, +4%, i.e. 42.2 h to 44.0 h).

As depicted in the graphs for MRT and clearance, this translates to the PK characteristics of the co-administered FVIII, even though mostly not as obvious as for D'D3-FP dimer (Table 8, FVIII:Ag): clearance is decreased by more than 20% (12.99 mL/kg/h to 10.66 mL/kg/h), MRT is increased by 12% (10.2 h to 11.4 h) and terminal half-life by 11% (8.9 h to 9.9 h).

Therewith, also for the full-length FVIII product Advate®, the increase in exposure over time is given by D'D3-FP dimer depending on the percentage of sialylation, as may also be seen by the fold increase of PK characteristics of Advate® given alone. While 40.6% sialylation prolong FVIII PK 2.3-2.9fold, an optimized D'D3-FP dimer with 87.3% sialylation prolongs FVIII PK 2.8-3.2fold.

TABLE 8

Pharmacokinetic parameters of D'D3-FP dimer and FVIII: Ag after coadministration of Advate ® and D'D3-FP dimer in rats (non-compartmental analysis)
Dose D'D3-FP dimer 1 mg/kg, dose Advate ® 200 IU/kg

| Treatment* | $C_{max}$, extrap. IU/mL | Clearance mL/kg/h | MRT h | Half-life, terminal h |
|---|---|---|---|---|
| Albumin | | | | |
| D'D3-FP dimer (40.6%) & Advate ® | 18.8 | 2.17 | 54.4 | 42.2 |
| D'D3-FP dimer (87.3%) & Advate ® | 17.2 | 1.32 | 62.0 | 44.0 |
| FVIII: Ag | | | | |
| Advate ® | 3.29 | 29.55 | 3.5 | 3.1 |
| D'D3-FP dimer (40.6%) & Advate ® | 3.19 | 12.99 2.3fold | 10.2 2.9fold | 8.9 2.9fold |
| D'D3-FP dimer (87.3%) & Advate ® | 3.38 | 10.66 2.8fold | 11.4 3.3fold | 9.9 3.2fold |

*degree of D'D3-FP dimer sialylation given in brackets

Conclusion from PK Study Results

These studies demonstrate that co-administration of D'D3-FP dimer and FVIII prolongs FVIII:Ag plasma exposure using different FVIII products. This prolongation is dependent on the status of sialylation of D'D3-FP dimer: generally, a better sialylation further optimizes FVIII plasma exposure. In detail, D'D3-FP dimer with a sialylation of 40.9% was inferior with regard to FVIII:Ag plasma exposure to D'D3-FP with sialylation in the range of 83.6-89.8%.

Since in the rat (in contrast to human haemophilia A patients), human and endogenous FVIII compete with D'D3-FP dimer binding sites, it may be expected that the effect on FVIII in the human haemophilia patient is even stronger.

EXAMPLE 9

In Vitro Sialylation of D'D3-FP

D'D3-FP dimer was dialyzed against 35 mM sodium acetate/35 mM Tris buffer at pH 7.0. To about 600 µg of the protein in 110 µl, 0.75 mg CMP-NANA (Roche Cat. No 05974003103) dissolved in 100 µl water as donor substrate and 10.5 µl ST6GAL-1 (60 µg, Roche Cat. No 07012250103, in water) were added. The mixture was incubated at 37° C. for 6 hours and the reaction was stopped by freezing at −15° C. to −25° C. This procedure was according to the manufacturer's recommendation. D'D3-FP dimer was then purified from the reagents by chromatography using SEC Superdex 200 pg (GE Healthcare, Code 90-1002-10). Sialylation was determined as described above and the results are given in Table 9.

TABLE 9 results of an in vitro sialylation study

| Lot # | Sialylation |
|---|---|
| starting material | 100 |
| after in vitro sialylation | 137% of the sialylation degree as compared to the starting material |

The degree of sialylation of the starting material was normalised to a nominal value of 100. The degree of sialylation after in vitro sialylation was substantially higher than that of the starting material.

EXAMPLE 10

Anion-Exchange Chromatography to Enrich for Highly Sialylated VWF Fragments

D'D3-FP prepared according to example 5 is further purified using anion exchange chromatography to reduce the content of asialo N-glycan structures. Therefore, the D'D3-FP solution is diluted using 20 mM Tris×HCl pH 7.4 buffer to a conductivity low enough to allow complete binding of D'D3-FP to the column (in general below 5 mS/cm) and loaded on a chromatography column (fill height approximately 20 cm) filled with Poros XQ resin that was equilibrated using equilibration buffer containing 20 mM Tris× HCl, 20 mM NaCl pH 7.4. After washing the column with equilibration buffer, D'D3-FP is eluted using a flat linear gradient from equilibration buffer to elution buffer (20 mM Tris×HCl, 500 mM NaCl pH 7.4). The elution peak containing D'D3-FP is fractionated into approximately 10 fractions of similar volumes and the early peak fractions that contain D'D3-FP with increased amounts of asialo N-glycan structures are discarded and the later peak fractions containing asialo N-glycan structures below the desired level (e.g. 20% or lower) are pooled.

Alternatively the purification run of D'D3-FP is performed with the difference that pooling of D'D3-FP eluate peak fractions is only done for those fractions containing D'D3-FP with an asialo N-glycan structure content of below 15% (or below 10%).

As described, by pooling of corresponding fractions suitable D'D3-FP preparations can be manufactured with a desired maximum content of asialo N-glycan structures.

Based on the results obtained with a linear gradient used for elution, step gradients with buffers containing different concentrations of NaCl can be derived that also allow removal of first fractions with higher amounts of asialo N-glycan structures thus resulting in D'D3-FP eluates with content of below 15% of asialo N-glycan structures.

EXAMPLE 11

Determination of FVIII Affinity to VWF Fragment Dimer and Monomer

D'D3-FP monomer and dimer were isolated as described above, and the affinity of FVIII to these preparations was assessed through surface plasmon resonance via a Biacore instrument (T200, GE Healthcare).

An anti-albumin antibody (MA1-20124, Thermo Scientific) was covalently coupled via its N-terminus to an activated CM 3 chip by NHS (N-Hydroxysuccinimide) and EDC (Ethanolamine hydrochloride), both contained in the amine coupling kit (BR1000-50) from GE Healthcare. For immobilization 3 µg/mL of the antibody were diluted in sodium acetate buffer (10 mM, pH 5.0) and the antibody solution was flown over the chip for 7 min. at a flow rate of 10 µL/min. After the immobilization procedure non-coupled dextran filaments were saturated by flowing ethanolamine solution (1 M, pH 8.3) over the chip for 5 min (at a flow rate of 10 µL/min). The aim of saturating the flow cell was to minimize unspecific binding of the analytes to the chip. A reference flow cell was set up by saturating an empty flow cell with ethanolamine by using the same procedure as above.

Dimeric and monomeric D'D3-FP proteins, respectively, were immobilized to the covalently coupled anti-albumin antibody by a flow of the D'D3-FP proteins (5 µg/mL) over the chip for 3 min (flow rate of 10 µL/min). The captured mass of dimeric D'D3-FP was 335 RU and for monomeric D'D3-FP 147 RU, assuming one binding site both on the monomer and on the dimer D'D3-FP for FVIII.

To create binding curves for FVIII, each D'D3-FP protein preparation was diluted in running buffer (HBS-P+: 0.1 M HEPES, 1.5 M NaCl and 0.5% v/v Surfactant P20, pH 7.4; product code BR100671, GE Healthcare) to concentrations of 0.25 nM, 0.5 nM, 1 nM, 3 nM and 4 nM. By performing a single cycle kinetic, samples with ascending concentrations of each dilution were flown over the chip for 2 min (flow rate 30 µL/min.), followed by a dissociation time of 10 min. with running buffer HBS-P+. All measurements were performed twice. The temperature for the measuring procedure was adjusted to +25° C.

Binding parameters were calculated using BiaEvaluation Software. The curve fitting methods were based on Langmuir equations. The input data for calculations were the molar mass of the analyte FVIII (rVIII-SingleChain) of 170 kDa, other parameters like max. RU and slopes were automatically extracted out of the fitted association and dissociation curves. The outputs of BiaEvaluation Software are the association rate constants and the dissociation rate constants, from which the affinity constants were calculated. The results are shown in Table 10.

TABLE 10

FVIII affinity data for D'D3-FP dimer and monomer

| D'D3-FP preparation | ka [1/Ms] | kd [1/s] | KD [M] |
| --- | --- | --- | --- |
| D'D3-FP Dimer | 2.33E+07 | 1.37E−03 | 5.90E−11 |
| D'D3-FP Monomer | 4.41E+07 | 3.96E−03 | 8.99E−11 |

The association rate constant was slightly increased for rVIII-SingleChain to the monomeric D'D3-FP, while the dissociation rate constant of rVIII-SingleChain to D'D3-FP dimer was three times slower than to the monomer. The quotient of the dissociation rate constant and the association rate constant indicates the affinity of rVIII-SingleChain to D'D3-FP. The dimeric D'D3-FP hence shows an increased affinity to FVIII compared to the D'D3-FP monomer.

EXAMPLE 12

Quantitative Determination of Individual N-Glycan Species

| Lot # | Percentage of all N-glycans with two or more terminal and non-sialylated galactose residues [% of total N-glycans] | Percentage of all N-glycans with three or more terminal and non-sialylated galactose residues [% of total N-glycans] |
| --- | --- | --- |
| B-140526 (no temperature shift) | 38.7 | 6.9 |
| B-140616KS | 21.2 | 2.2 |
| B-140825 | 17.8 | 1.9 |
| B-140623KS | 9.5 | 1.1 |

The N-Glycans released by PNGase F were labelled with a fluorophore 2-aminobenzamide (AB) and purified prior analysis using in-line LC-fluorescence—high resolution MS detection allowing simultaneous quantitative determination and identification of the labelled N-Glycans using accurate mass and retention time information. Using a mixed mode HILIC/RP LC-column allowed the separation of the released and AB labelled N-Glycans based on charge and structure which enabled a quantitative determination of different structures according to the number of terminal galactose and non-sialylated residues. The standard deviation of the fluorescence quantitation using the area under curve was found to be on average less than 0.5% using a reference sample (n=5). The presence of terminal and non-sialylated galactose residues in the separated AB labelled N-glycans was confirmed by treating the released AB-labelled N-glycans with β1-4-Galactosidase and re-injecting them using the same LC-FLD-MS methods and analysing the shifted peaks.

The following methods were applied:

PNGase F Enzymatic Glycan Release:

About 700 µg of the purified protein was reduced with DTT in ammonium bicarbonate, pH 8.5 at 60° C. for 30 min. The reduced sample was cooled to room temperature and alkylated with iodoacetamide at RT in the dark for 30 min. The alkylated sample was buffer exchanged into 50 mM ammonium bicarbonate pH 8.6 using a 2 mL Zeba Spin 7K MWCO column. To the buffer exchanged sample, 40 U of PNGase was added and the sample incubated at 37° C. for 14 hours. An additional 40 U of PNGase was added and the sample incubated for a further 6 hours at 37° C. The PNGase digested sample was centrifuged through a 50 KDa Amicon Ultra 4 ultrafilter. The filtrate was dried in a CentriVap.

2-AB Labelling of Released N-Glycans:

The 2-AB labelling reagent was prepared following the manufacture instructions. 50 µL of the 2-AB reagent was added to the dried sample and incubated in the dark at 65° C. for 3.5 hours.

A Waters Oasis HLB 3cc 60 mg SPE cartridge was conditioned with 3 mL 95% acetonitrile the 3 mL 35% acetonitrile then 3 mL 95% acetonitrile. The 2-AB labelled sample was diluted by adding 1.95 mL of 95% v/v acetonitrile and immediately loaded onto the HLB cartridge and allowed to drain under gravity. Sample was washed under gravity with 3×3 mL of 95% v/v acetonitrile and the eluted with 3 mL of 35% v/v acetonitrile. The dried 2-AB derivatised sample was dissolved by the addition of 35 µL of Milli Q water and vortex mixing. After dissolution, 85 µL of acetonitrile was added and mixed briefly. The sample was transferred to a HPLC vial for analysis.

2-AB Glycan Analysis:

High performance liquid chromatography was performed on a Thermo Dionex Ultimate 3000 system consisting of an RS Binary Pump, Autosampler, RS Column Compartment and RS Fluorescence detector. The separation of 2-AB glycan derivatives was achieved using a Dionex GlycanPac AXH-1, 1.9 µm, 2.1×150 mm column (P/N 082472). Mobile phase A consisted of 100% acetonitrile, Mobile phase B consisted of 50 mM formic acid adjusted to pH 4.0 with 5M ammonium hydroxide solution. The column was maintained at 50° C. and the flow rate was 0.200 mL/min. Fluorescence detection was performed with an excitation wavelength of 320 nm and an emission wavelength of 420 nm.

The LC-FLD system was coupled to a high resolution orthogonal TOF-MS (MaXis, Bruker-Daltonik, Bremen, Germany). The transfer capillary was kept at a voltage of −4500 V (positive ion polarity mode). The nebulizer was set to 0.8 bar using the standard ESI sprayer (Bruker, Bremen, Germany), the dry gas temperature to 180° C. and the dry gas flow-rate to 7 L/min. The ion transfer was optimized in the range m/z 200-3000 for highest sensitivity while keeping the resolution R>50,000 across the whole mass range. The TOF-MS mass calibration was carried out prior the LC-MS experiment by direct infusion of a 100 fold dilution of ES Tuning Mix (Agilent Technologies, Waldbronn, Germany) at 4 ul/min.

The invention claimed is:

1. A method of producing a glycoprotein comprising N-glycans that have increased sialylation, wherein the method comprises (i) providing cells comprising a nucleic acid sequence encoding a polypeptide comprising a truncated von Willebrand Factor (VWF), and (ii) culturing the cells at a temperature of less than 36.0° C.; wherein
the truncated VWF comprises an amino acid sequence having at least 90% sequence identity to amino acids 764 to 1242 of SEQ ID NO:9; and
the glycoprotein is the polypeptide comprising the truncated VWF.

2. The method of claim 1, wherein the method produces a dimer of the glycoprotein VWF, or wherein the method increases dimerization of the glycoprotein.

3. The method of claim 1, wherein the cells further comprise a recombinant nucleic acid sequence encoding a sialyltransferase.

4. The method of claim 1, wherein prior to (ii) the cells are cultured at a temperature of 37.0° C.±1.0° C., and during (ii) the cells are cultured at a temperature of 34.0° C.±2.0° C.

5. A method of producing a glycoprotein comprising N-glycans that have increased sialylation, wherein the method comprises (i) providing cells comprising (a) a nucleic acid sequence encoding a polypeptide comprising a truncated von Willebrand Factor (VWF) and (b) a recombinant nucleic acid sequence encoding an α-2,6-sialyltransferase, and (ii) culturing the cells under conditions that allow expression of the glycoprotein and the α-2,6-sialyltransferase; wherein
the truncated VWF comprises an amino acid sequence having at least 90% sequence identity to amino acids 764 to 1242 of SEQ ID NO:9; and
the glycoprotein is the polypeptide comprising the truncated VWF.

6. The method of claim 1, further comprising (i) subjecting the glycoprotein to ion exchange chromatography, whereby fractions of glycoprotein with high sialylation are separated from fractions of glycoprotein with low sialylation; and collecting the fractions-having high sialylation; or (ii) contacting the glycoprotein with a sialyltransferase and a sialic acid donor in vitro.

7. The method of claim 1, wherein at least 75% of the N-glycans on the glycoprotein comprise at least one sialic acid moiety.

8. The method of claim 1, wherein at least 50% of the glycoprotein is a dimer.

9. The method of claim 3, wherein the sialyltransferase is an α-2,6-sialyltransferase, an α-2,3-sialyltransferase, or a combination thereof.

10. The method of claim 1, wherein the truncated VWF comprises amino acids 764 to 1242 of SEQ ID NO:9.

11. The method of claim 1, wherein the truncated VWF consists of an amino acid sequence having at least 90% sequence identity to amino acids 764 to 1242 of SEQ ID NO:9.

12. The method of claim 5, wherein the truncated VWF comprises amino acids 764 to 1242 of SEQ ID NO:9.

13. The method of claim 5, wherein the truncated VWF consists of amino acids 764 to 1242 of SEQ ID NO:9.

* * * * *

UNITED STATES PATENT AND TRADEMARK OFFICE
CERTIFICATE OF CORRECTION

PATENT NO. : 10,772,936 B2
APPLICATION NO. : 15/576061
DATED : September 15, 2020
INVENTOR(S) : Stefan Schulte et al.

Page 1 of 1

It is certified that error appears in the above-identified patent and that said Letters Patent is hereby corrected as shown below:

In the Claims

In Claim 6, Column 104, Line 36, "fractions-having" should read --fractions having--.

Signed and Sealed this
First Day of December, 2020

Andrei Iancu
*Director of the United States Patent and Trademark Office*